United States Patent
O'Hear et al.

(10) Patent No.: US 12,291,575 B2
(45) Date of Patent: May 6, 2025

(54) METHODS FOR TREATMENT OF CD20-POSITIVE PROLIFERATIVE DISORDER WITH MOSUNETUZUMAB AND POLATUZUMAB VEDOTIN

(71) Applicant: Genentech, Inc., South San Francisco, CA (US)

(72) Inventors: Carol Elaine O'Hear, South San Francisco, CA (US); Yasuhiro Oki, South San Francisco, CA (US); Iris Tranthuyngan To, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 113 days.

(21) Appl. No.: 17/744,262

(22) Filed: May 13, 2022

(65) Prior Publication Data

US 2022/0411528 A1 Dec. 29, 2022

Related U.S. Application Data

(60) Provisional application No. 63/292,887, filed on Dec. 22, 2021, provisional application No. 63/188,695, filed on May 14, 2021.

(51) Int. Cl.
*A61P 35/00* (2006.01)
*C07K 16/28* (2006.01)
*A61K 39/00* (2006.01)

(52) U.S. Cl.
CPC .......... *C07K 16/2887* (2013.01); *A61P 35/00* (2018.01); *C07K 16/2866* (2013.01); *C07K 16/2896* (2013.01); *A61K 2039/507* (2013.01); *A61K 2039/545* (2013.01)

(58) Field of Classification Search
CPC ................................................. C07K 16/2887
USPC ...................................................... 424/144.1
See application file for complete search history.

(56) References Cited

U.S. PATENT DOCUMENTS

| | | | |
|---|---|---|---|
| 5,500,362 A | 3/1996 | Robinson et al. | |
| 5,624,821 A | 4/1997 | Winter et al. | |
| 5,648,260 A | 7/1997 | Winter et al. | |
| 5,677,171 A | 10/1997 | Hudziak et al. | |
| 5,731,168 A | 3/1998 | Carter et al. | |
| 5,821,337 A | 10/1998 | Carter et al. | |
| 5,869,046 A | 2/1999 | Presta et al. | |
| 6,194,551 B1 | 2/2001 | Idusogie et al. | |
| 6,248,516 B1 | 6/2001 | Winter et al. | |
| 6,455,043 B1 | 9/2002 | Grillo-Lopez | |
| 6,602,684 B1 | 8/2003 | Umana et al. | |
| 6,737,056 B1 | 5/2004 | Presta | |
| 7,332,581 B2 | 2/2008 | Presta | |
| 7,371,826 B2 | 5/2008 | Presta | |
| 7,435,797 B2 | 10/2008 | Lowman et al. | |
| 7,612,181 B2 | 11/2009 | Wu et al. | |
| 7,682,612 B1 | 3/2010 | White et al. | |
| 7,695,936 B2 | 4/2010 | Carter et al. | |
| 7,799,900 B2 | 9/2010 | Adams et al. | |
| 7,951,546 B2 | 5/2011 | Frantz et al. | |
| 8,219,149 B2 | 7/2012 | Lafata et al. | |
| 8,258,268 B2 | 9/2012 | Wu et al. | |
| 8,562,992 B2 | 10/2013 | Adams et al. | |
| 8,709,421 B2 | 4/2014 | Heiss et al. | |
| 8,722,859 B2 | 5/2014 | Miller et al. | |
| 8,895,702 B2 | 11/2014 | Williams et al. | |
| 8,969,526 B2 | 3/2015 | Baehner et al. | |
| 9,011,864 B2 | 4/2015 | Schulz et al. | |
| 9,017,676 B2 | 4/2015 | Lindhofer | |
| 9,308,257 B2 | 4/2016 | Sharma, Sr. et al. | |
| 9,315,567 B2 | 4/2016 | Chang et al. | |
| 9,493,563 B2 | 11/2016 | Blein et al. | |
| 9,587,021 B2 | 3/2017 | Huang et al. | |
| 9,657,102 B2 | 5/2017 | Smith et al. | |
| 9,714,294 B2 | 7/2017 | De Goeij et al. | |
| 10,000,576 B1 | 6/2018 | Weisser et al. | |
| 10,105,391 B2 | 10/2018 | Wu et al. | |
| 10,357,571 B2 | 7/2019 | Williams et al. | |
| 10,561,686 B2 | 2/2020 | Xiao et al. | |
| 11,466,094 B2 * | 10/2022 | Chu .................. | C07K 16/2809 |
| 2002/0164328 A1 | 11/2002 | Shinkawa et al. | |
| 2003/0115614 A1 | 6/2003 | Kanda et al. | |
| 2003/0157108 A1 | 8/2003 | Presta | |
| 2004/0093621 A1 | 5/2004 | Shitara et al. | |
| 2004/0109865 A1 | 6/2004 | Niwa et al. | |
| 2004/0110282 A1 | 6/2004 | Kanda et al. | |
| 2004/0110704 A1 | 6/2004 | Yamane et al. | |

(Continued)

FOREIGN PATENT DOCUMENTS

| | | |
|---|---|---|
| CN | 102281902 A | 12/2011 |
| CN | 102369218 A | 3/2012 |

(Continued)

OTHER PUBLICATIONS

Wolska-Washer et al (Drug Safety, 2019, 42: 295-314).*
Trněný et al.(Haematologica, 2018, 103(8): 1351-1358).*
WHO Drug Information (vol. 31, No. 2, 2017).*
"Purified Mouse Anti-Human CD3-epsilon Clone SP34," BD Biosciences,<https://www.bdbiosciences.com/us/reagents/research/antibodies-buffers/immunology-reagents/anti-non-human-primate-antibodies/cell-surface-antigens/purified-mouse-anti-human-cd3-sp34/p/556610>, retrieved on Jan. 4, 2021 (4 pages).
Anderson et al., "G19.4(alpha CD3) x B43(alpha CD19) monoclonal antibody heteroconjugate triggers CD19 antigen-specific lysis of t(4;11) acute lymphoblastic leukemia cells by activated CD3 antigen-positive cytotoxic T cells," Blood. 80(11):2826-34 (1992) (10 pages).

(Continued)

*Primary Examiner* — Sean E Aeder
(74) *Attorney, Agent, or Firm* — Clark & Elbing LLP; Karen L. Elbing

(57) ABSTRACT

The present invention relates to the treatment of subjects having a CD20-positive cell proliferative disorder. More specifically, the invention pertains to the treatment of subjects having a CD20-positive cell proliferative disorder by administering a combination of mosunetuzumab and polatuzumab vedotin.

43 Claims, 2 Drawing Sheets

Specification includes a Sequence Listing.

(56) References Cited

U.S. PATENT DOCUMENTS

| | | | |
|---|---|---|---|
| 2004/0132140 A1 | 7/2004 | Satoh et al. |
| 2005/0014934 A1 | 1/2005 | Hinton et al. |
| 2005/0095243 A1 | 5/2005 | Chan et al. |
| 2005/0123546 A1 | 6/2005 | Umana et al. |
| 2009/0075279 A1 | 3/2009 | Frantz et al. |
| 2009/0252683 A1 | 10/2009 | Kischel et al. |
| 2009/0304719 A1 | 12/2009 | Daugherty et al. |
| 2010/0015133 A1 | 1/2010 | Igawa et al. |
| 2010/0150918 A1 | 6/2010 | Kufer et al. |
| 2010/0331527 A1 | 12/2010 | Davis et al. |
| 2011/0020322 A1 | 1/2011 | Wilkins et al. |
| 2011/0123532 A1 | 5/2011 | Gurney et al. |
| 2011/0178279 A1 | 7/2011 | Williams et al. |
| 2012/0244577 A1 | 9/2012 | Dixit et al. |
| 2012/0251531 A1 | 10/2012 | Baehner et al. |
| 2013/0129723 A1 | 5/2013 | Blankenship et al. |
| 2013/0165638 A1 | 6/2013 | Hsu et al. |
| 2013/0171095 A1 | 7/2013 | Bernett et al. |
| 2013/0266568 A1 | 10/2013 | Brinkmann et al. |
| 2013/0287774 A1 | 10/2013 | Zugmaier et al. |
| 2014/0079689 A1 | 3/2014 | Elliott et al. |
| 2014/0088295 A1 | 3/2014 | Smith et al. |
| 2014/0112914 A1 | 4/2014 | Nezu et al. |
| 2014/0170148 A1 | 6/2014 | De Goeij et al. |
| 2014/0170149 A1 | 6/2014 | Neijssen et al. |
| 2014/0187753 A1 | 7/2014 | Blein et al. |
| 2014/0302064 A1 | 10/2014 | Moore |
| 2014/0377270 A1 | 12/2014 | Moore et al. |
| 2015/0079093 A1 | 3/2015 | Stuhler |
| 2015/0098900 A1 | 4/2015 | Ebens et al. |
| 2015/0133640 A1 | 5/2015 | Blein et al. |
| 2015/0166661 A1 | 6/2015 | Chen et al. |
| 2015/0266966 A1 | 9/2015 | Smith et al. |
| 2015/0284475 A1 | 10/2015 | Zhou et al. |
| 2016/0000916 A1 | 1/2016 | Crotts et al. |
| 2016/0017058 A1 | 1/2016 | Kim et al. |
| 2016/0075785 A1 | 3/2016 | Ast et al. |
| 2016/0082120 A1* | 3/2016 | Polson ............. A61K 39/39558 424/133.1 |
| 2016/0090416 A1 | 3/2016 | Gunde et al. |
| 2016/0145339 A1 | 5/2016 | Zhou et al. |
| 2016/0152711 A1 | 6/2016 | Williams et al. |
| 2016/0159906 A1 | 6/2016 | Sun et al. |
| 2016/0194399 A1 | 7/2016 | Irving et al. |
| 2016/0368985 A1 | 12/2016 | Hotzel et al. |
| 2016/0368994 A1 | 12/2016 | Kelley et al. |
| 2017/0008971 A1 | 1/2017 | Dennis et al. |
| 2017/0022274 A1 | 1/2017 | Chang et al. |
| 2017/0158773 A1 | 6/2017 | Adams et al. |
| 2017/0204194 A1 | 7/2017 | Chen et al. |
| 2017/0209573 A1 | 7/2017 | Bacac et al. |
| 2017/0218074 A1 | 8/2017 | Williams et al. |
| 2017/0224818 A1 | 8/2017 | Lindhofer et al. |
| 2017/0267783 A1 | 9/2017 | Nezu et al. |
| 2018/0057593 A1 | 3/2018 | Dennis |
| 2018/0134798 A1 | 5/2018 | Chu et al. |
| 2018/0148508 A1 | 5/2018 | Wang et al. |
| 2018/0193479 A1 | 7/2018 | Williams et al. |
| 2020/0129617 A1 | 4/2020 | Brownstein et al. |
| 2020/0164077 A1 | 5/2020 | Williams et al. |
| 2020/0199578 A1 | 6/2020 | Short et al. |
| 2020/0339686 A1 | 10/2020 | Sato et al. |
| 2022/0153842 A1 | 5/2022 | Li et al. |

FOREIGN PATENT DOCUMENTS

| | | |
|---|---|---|
| CN | 102471380 A | 5/2012 |
| CN | 103025759 A | 4/2013 |
| CN | 101675077 B | 9/2013 |
| CN | 104321081 A | 1/2015 |
| CN | 106029696 A | 10/2016 |
| EP | 1870459 A1 | 12/2007 |
| EP | 1923072 A1 | 5/2008 |
| EP | 1870459 A4 | 9/2010 |
| EP | 2482212 A1 | 8/2012 |
| EP | 2578230 A1 | 4/2013 |
| EP | 2647707 A1 | 10/2013 |
| EP | 2647707 A4 | 4/2014 |
| EP | 2769989 A1 | 8/2014 |
| EP | 2789630 A1 | 10/2014 |
| EP | 2840091 A1 | 2/2015 |
| EP | 1870459 B1 | 6/2016 |
| JP | 2008-291036 A | 12/2008 |
| JP | 2009-539413 A | 11/2009 |
| JP | 2010-524435 A | 7/2010 |
| JP | 2013-515509 A | 5/2013 |
| JP | 2013-528569 A | 7/2013 |
| JP | 2013-529084 A | 7/2013 |
| JP | 2015-509951 A | 4/2015 |
| JP | 2015-509952 A | 4/2015 |
| JP | 2018-527887 A | 9/2018 |
| KR | 10-2016-0098464 A | 8/2016 |
| RU | 2539112 C2 | 1/2015 |
| TW | 201508008 A | 3/2015 |
| TW | 201827075 A | 8/2018 |
| WO | WO-91/03493 A1 | 3/1991 |
| WO | WO-92/22653 A1 | 12/1992 |
| WO | WO-94/04679 A1 | 3/1994 |
| WO | WO-94/29351 A2 | 12/1994 |
| WO | WO-96/01126 A1 | 1/1996 |
| WO | WO-96/27011 A1 | 9/1996 |
| WO | WO-97/30087 A1 | 8/1997 |
| WO | WO-98/50431 A2 | 11/1998 |
| WO | WO-98/58964 A1 | 12/1998 |
| WO | WO-98/50431 A3 | 1/1999 |
| WO | WO-99/22764 A1 | 5/1999 |
| WO | WO-99/51642 A1 | 10/1999 |
| WO | WO-00/61739 A1 | 10/2000 |
| WO | WO-01/29246 A1 | 4/2001 |
| WO | WO-02/31140 A1 | 4/2002 |
| WO | WO-03/011878 A2 | 2/2003 |
| WO | WO-03/084570 A1 | 10/2003 |
| WO | WO-03/085107 A1 | 10/2003 |
| WO | WO-03/085119 A1 | 10/2003 |
| WO | WO-03/087131 A2 | 10/2003 |
| WO | WO-2004/056312 A2 | 7/2004 |
| WO | WO-2004/106380 A2 | 12/2004 |
| WO | WO-2005/035586 A1 | 4/2005 |
| WO | WO-2005/035778 A1 | 4/2005 |
| WO | WO-2005/053742 A1 | 6/2005 |
| WO | WO-2005/083431 A2 | 9/2005 |
| WO | WO-2005/100402 A1 | 10/2005 |
| WO | WO-2006/029879 A2 | 3/2006 |
| WO | WO-2007/005874 A2 | 1/2007 |
| WO | WO-2007/042261 A2 | 4/2007 |
| WO | WO-2007/110205 A2 | 10/2007 |
| WO | WO-2007/146968 A2 | 12/2007 |
| WO | WO-2008/077546 A1 | 7/2008 |
| WO | WO-2008/119566 A2 | 10/2008 |
| WO | WO-2008/119567 A2 | 10/2008 |
| WO | WO-2009/070642 A1 | 6/2009 |
| WO | WO-2009/106321 A1 | 9/2009 |
| WO | WO-2010/057109 A1 | 5/2010 |
| WO | WO-2010/077643 A1 | 7/2010 |
| WO | WO-2010/114940 A1 | 10/2010 |
| WO | WO-2010/120561 A1 | 10/2010 |
| WO | WO-2011/028945 A1 | 3/2011 |
| WO | WO-2011/028952 A1 | 3/2011 |
| WO | WO-2011/090754 A1 | 7/2011 |
| WO | WO-2011/090762 A1 | 7/2011 |
| WO | WO-2011/121110 A1 | 10/2011 |
| WO | WO-2011/131746 A2 | 10/2011 |
| WO | WO-2011/143545 A1 | 11/2011 |
| WO | WO-2012/025525 A1 | 3/2012 |
| WO | WO-2012/058768 A1 | 5/2012 |
| WO | WO-2012/058768 A8 | 6/2012 |
| WO | WO-2012/073985 A1 | 6/2012 |
| WO | WO-2012/075581 A1 | 6/2012 |
| WO | WO-2012/123949 A1 | 9/2012 |
| WO | WO-2012/143524 A2 | 10/2012 |
| WO | WO-2012/158818 A2 | 11/2012 |
| WO | WO-2012/162067 A2 | 11/2012 |
| WO | WO-2013/026831 A1 | 2/2013 |

(56) References Cited

FOREIGN PATENT DOCUMENTS

| | | |
|---|---|---|
| WO | WO-2013/128027 A1 | 9/2013 |
| WO | WO-2013/128194 A1 | 9/2013 |
| WO | WO-2014/012085 A2 | 1/2014 |
| WO | WO-2014/022540 A1 | 2/2014 |
| WO | WO-2014/028560 A2 | 2/2014 |
| WO | WO-2014/047231 A1 | 3/2014 |
| WO | WO-2014/028560 A3 | 5/2014 |
| WO | WO-2014/081955 A1 | 5/2014 |
| WO | WO-2014/082179 A1 | 6/2014 |
| WO | WO-2014/083178 A1 | 6/2014 |
| WO | WO-2014/108483 A1 | 7/2014 |
| WO | WO-2014/122251 A2 | 8/2014 |
| WO | WO-2014/141152 A2 | 9/2014 |
| WO | WO-2014/144722 A2 | 9/2014 |
| WO | WO-2014/153002 A1 | 9/2014 |
| WO | WO-2014/122251 A3 | 10/2014 |
| WO | WO-2014/170063 A1 | 10/2014 |
| WO | WO-2014/141152 A3 | 12/2014 |
| WO | WO-2014/191113 A1 | 12/2014 |
| WO | WO-2014/193973 A2 | 12/2014 |
| WO | WO-2014/210064 A1 | 12/2014 |
| WO | WO-2015/006749 A2 | 1/2015 |
| WO | WO-2015/013671 A1 | 1/2015 |
| WO | WO-2014/191113 A8 | 2/2015 |
| WO | WO-2015/018527 A1 | 2/2015 |
| WO | WO-2015/095392 A1 | 6/2015 |
| WO | WO-2015/143079 A1 | 9/2015 |
| WO | WO-2015/184203 A1 | 12/2015 |
| WO | WO-2015/184207 A1 | 12/2015 |
| WO | WO-2016/014942 A1 | 1/2016 |
| WO | WO-2016/019969 A1 | 2/2016 |
| WO | WO-2016/020065 A1 | 2/2016 |
| WO | WO-2016/036678 A1 | 3/2016 |
| WO | WO-2016/049214 A1 | 3/2016 |
| WO | WO-2016/081490 A1 | 5/2016 |
| WO | WO-2016/090210 A1 | 6/2016 |
| WO | WO-2016/110576 A1 | 7/2016 |
| WO | WO-2016/135239 A1 | 9/2016 |
| WO | WO-2016/179003 A1 | 11/2016 |
| WO | WO-2016/191750 A1 | 12/2016 |
| WO | WO-2016/201300 A1 | 12/2016 |
| WO | WO-2016/204966 A1 | 12/2016 |
| WO | WO-2016/205520 A1 | 12/2016 |
| WO | WO-2016/205531 A2 | 12/2016 |
| WO | WO-2017/132279 A1 | 8/2017 |
| WO | WO-2018/093821 A1 | 5/2018 |
| WO | WO-2020/232169 A1 | 11/2020 |
| WO | WO-2022/098648 A2 | 5/2022 |

OTHER PUBLICATIONS

Atwell et al., "Stable Heterodimers from Remodeling the Domain Interface of a Homodimer using a Phage Display Library," J Mol Biol. 270(1):26-35 (1997).

Baeuerle et al., "Bispecific T-cell engaging antibodies for cancer therapy," Cancer Res. 69(12):4941-4 (2009).

Bortoletto et al., "Optimizing anti-CD3 affinity for effective T cell targeting against tumor cells," Eur J Immunol. 32(11):3102-7 (2002).

Brack et al., "A Bispecific HER2-Targeting FynomAb with Superior Antitumor Activity and Novel Mode of Action," Mol Cancer Ther. 13(8):2030-39 (2014) (11 pages).

Brekke et al., "Human IgG isotype-specific amino acid residues affecting complement-mediated cell lysis and phagocytosis," Eur J Immunol. 24(10):2542-7 (1994).

Brinkmann et al., "The making of bispecific antibodies," mAbs. 9(2):182-212 (Nov. 2017).

Brown et al., "Tolerance of single, but not multiple, amino acid replacements in antibody VH CDR2: a means of minimizing B cell wastage from somatic hypermutation?" J Immunol. 156(9):3285-91 (1996).

Brüggemann et al., "Comparison of the Effector Functions of Human Immunoglobulins Using a Matched set of Chimeric Antibodies," J Exp Med. 166(5):1351-61 (1987).

Budde et al., "Mosunetuzumab, a Full-Length Bispecific CD20/CD3 Antibody, Displays Clinical Activity in Relapsed/Refractory B-Cell Non-Hodgkin Lymphoma (NHL): Interim Safety and Efficacy Results from a Phase 1 Study," Blood. 132(Supplement 1):399 (2018) (6 pages).

Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplant. 43(5):383-97 (2009).

Buhmann et al., "Immunotherapy with FBTA05 (Bi20), a trifunctional bispecific anti-CD3 x anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, dose-escalating Phase I/II-trial," J Transl Med. 11:160 (2013) (9 pages).

Carter, "Bispecific human IgG by design," J Immunol Methods. 248(1-2):7-15 (2001).

Choi et al., "Bispecific antibodies engage T cells for antitumor immunotherapy," Expert Opin Biol Ther. 11(7):843-53 (2011).

Chu et al., "Immunotherapy with long-lived anti-CD20 x anti-CD3 bispecific antibodies stimulates potent T cell-mediated killing of human B cell lines and of circulating and lymphoid B cells in monkeys: a potential therapy for B cell lymphomas and leukemias," Blood. 124(21):3111 (2014) (1 page).

Clark et al., "Affinity enhancement of an in vivo matured therapeutic antibody using structure-based computational design," Protein Sci. 15(5):949-60 (2006).

Clynes et al., "Fc receptors are required in passive and active immunity to melanoma," Proc Natl Acad Sci U S A. 95(2):652-6 (1998).

Cragg et al., "Antibody specificity controls in vivo effector mechanisms of anti-CD20 reagents," Blood. 103(7):2738-43 (2004).

Cragg et al., "Complement-mediated lysis by anti-CD20 mAb correlates with segregation into lipid rafts," Blood. 101(3):1045-52 (2003).

Desnoyers et al., "Tumor-Specific Activation of an EGFR-Targeting Probody Enhances Therapeutic Index," Sci Transl Med. 5(207):207ra144 (2013) (10 pages).

Desnoyers et al., "Tumor-specific activation of an EGFR-targeting probody enhances therapeutic index," Sci Transl Med. 5(207):207ra144 (2013) (2 pages) (Abstract only).

Diefenbach et al., "An individualized risk mitigation approach for safety: experience from the mosunetuzumab (CD20/CD3 bispecific antibody) development program in relation to neurotoxicity risk," 61st ASH Annual Meeting & Exposition, Dec. 7-10, Orlando, Florida, Poster P-4728 (2019) (1 page).

Donaldson et al., "Design and development of masked therapeutic antibodies to limit off-target effects: application to anti-EGFR antibodies," Cancer Biol Ther. 8(22): 2145-50 (2009) (6 pages).

Drent et al., "A Rational Strategy for Reducing On-Target Off-Tumor Effects of CD38-Chimeric Antigen Receptors by Affinity Optimization," Mol Ther. 25(8):1946-58 (Aug. 2017).

Duncan et al., "The binding site for C1q on IgG," Nature. 332(6166):738-40 (1988).

Edelman et al., "The covalent structure of an entire gammaG immunoglobulin molecule," Proc Natl Acad Sci U S A. 63(1):78-85 (1969).

Erster et al., "Site-specific targeting of antibody activity in vivo mediated by disease-associated proteases," J Control Release. 161(3): 804-12 (2012) (2 pages) (Abstract only).

Gaston et al., "Intracellular delivery of therapeutic antibodies into specific cells using antibody-peptide fusions," Sci Rep. 9(1):18688 (2019) (12 pages).

Gazzano-Santoro et al., "A non-radioactive complement-dependent cytotoxicity assay for anti-CD20 monoclonal antibody," J Immunol Methods. 202(2):163-71 (1997).

Genentech, "A Phase I Study of BTRC4017A in Participants With Locally Advanced or Metastatic HER2-Expressing Cancers," ClinicalTrials.gov, <https://clinicaltrials.gov/ct2/show/NCT03448042?term=BTRC4017A&draw=2&rank=1>, dated Feb. 27, 2018, retrieved on Nov. 2, 2021 (7 pages).

Goebeler et al., "Bispecific T-cell Engager (BiTE) Antibody Construct Blinatumomab for the Treatment of Patients With Relapsed/

(56) References Cited

OTHER PUBLICATIONS

Refractory Non-Hodgkin Lymphoma: Final Results From a Phase I Study," J Clin Oncol. 34(10):1104-11 (Apr. 2016) (13 pages).
Gonzales et al., "Minimizing the Immunogenicity of Antibodies for Clinical Application," Tumour Biol. 26(1):31-43 (2005) (1 page) (Abstract only).
Guyer et al., "Immunoglobulin binding by mouse intestinal epithelial cell receptors," J Immunol. 117(2):587-93 (1976).
Haile et al., "Soluble CD80 Restores T Cell Activation and Overcomes Tumor Cell Programmed Death Ligand 1-Mediated Immune Suppression," J Immunol. 191(5):2829-36 (2013) (9 pages).
Han et al., "Masked Chimeric Antigen Receptor for Tumor-Specific Activation," Mol Ther. 25(1):274-84 (Jan. 2017).
Hellström et al., "Antitumor effects of L6, an IgG2a antibody that reacts with most human carcinomas," Proc Natl Acad Sci U S A. 83(18):7059-63 (1986).
Hellström et al., "Strong antitumor activities of IgG3 antibodies to a human melanoma-associated ganglioside," Proc Natl Acad Sci U S A. 82(5):1499-502 (1985).
Hernandez et al., "Pharmacodynamic Effects and Immune Correlates of Response to the CD20/CD3 Bispecific Antibody Mosunetuzumab in Relapsed or Refractory Non-Hodgkin Lymphoma," Blood. 134(Supplement 1):1585 (2019) (4 pages).
Holliger et al., "'Diabodies': small bivalent and bispecific antibody fragments," Proc Natl Acad Sci USA. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hosseini et al., "Abstract B043: Systems pharmacology modeling of anti-CD20/CD3 T-cell dependent bispecific antibody and its application to clinical trial design," Proceedings of the Second CRI-CIMT-EATI-AACR International Cancer Immunotherapy Conference: Translating Science into Survival; Sep. 25-28; New York, NY. Cancer Immunol Res. 4(11 Suppl):Abstract nr B043 (2016) (4 pages).
Hosseini et al., "Mitigating The Risk Of Cytokine Release Syndrome In A Phase I Trial Of CD20/CD3 Bispecific Antibody Mosunetuzumab In NHL: Impact Of Translational System Modeling," NPJ Syst Biol Appl. 6(1):28 (2020) (11 pages).
Hosseini et al., "Systems pharmacology modeling of anti-CD20/CD3 T-cell dependent bispecific antibody and its application to clinical trial design," American Conference on Pharmacometrics 7; Oct. 25; Bellevue, WA. (2016) (1 page).
Huang et al., "In Vivo Deamidation Characterization of Monoclonal Antibody by LC/MS/MS," Anal Chem. 77(5):1432-9 (2005).
Huang, "Structural chemistry and therapeutic intervention of protein-protein interactions in immune response, human immunodeficiency virus entry, and apoptosis," Pharmacol Ther. 86(3):201-215 (2000).
Hudson et al., "Engineered antibodies," Nat Med. 9(1):129-34 (2003).
Huehls et al., "Bispecific T-cell engagers for cancer immunotherapy," Immunol Cell Biol. 93(3):290-6 (2015).
Hutchings et al., "Dose escalation of subcutaneous epcoritamab in patients with relapsed or refractory B-cell non-Hodgkin lymphoma: an open-label, phase 1/2 study," Lancet. 398(10306):1157-69 (Sep. 2021).
Idusogie et al., "Mapping of the C1q Binding Site on Rituxan, A Chimeric Antibody with a Human IgG1 Fc," J Immunol. 164(8):4178-84 (2000).
Igawa et al., "VH/VL interface engineering to promote selective expression and inhibit conformational isomerization of thrombopoietin receptor agonist single-chain diabody," Protein Eng Des Sel. 23(8):667-77 (2010) (11 pages).
Jager et al., "The trifunctional antibody ertumaxomab destroys tumor cells that express low levels of human epidermal growth factor receptor 2," Cancer Res. 69(10):4270-6 (2009).

Junttila et al., "Antitumor Efficacy of a Bispecific Antibody That Targets HER2 and Activates T Cells," Cancer Res. 74(19):5561-71 (2014).
Kanda et al., "Comparison of cell lines for stable production of fucose-negative antibodies with enhanced ADCC," Biotechnol Bioeng. 94(4):680-8 (2006).
Kegg Drug Database Accession No. D03257, "Drug: Trastuzumab," <https://www.genome.jp/dbget-bin/www_bget?dr:D03257>, retrieved on Jan. 8, 2019 (2 pages).
Kelley et al., "Thermodynamic Analysis of an Antibody Functional Epitope," Biochemistry. 32(27):6828-35 (1993).
Kiewe et al., "Phase I trial of the trifunctional anti-HER2 x anti-CD3 antibody ertumaxomab in metastatic breast cancer," 2005 ASCO Annual Meeting Proceedings. J Clin Oncol. 23(16S):Abstract 2530 (2005) (1 page).
Kiewe et al., "Phase I trial of the trifunctional anti-HER2 x anti-CD3 antibody ertumaxomab in metastatic breast cancer," Clin Cancer Res. 12(10):3085-91 (2006).
Kim et al., "Localization of the site of the murine IgG1 molecule that is involved in binding to the murine intestinal Fc receptor," Eur J Immunol. 24(10):2429-34 (1994).
Kipriyanov et al., "Bispecific Tandem Diabody for Tumor Therapy with Improved Antigen Binding and Pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kong et al., "Characterization and function of human Ly-6/uPAR molecules," BMB Rep. 45(11):595-603 (2012).
Kontermann, "Dual targeting strategies with bispecific antibodies," MAbs. 4(2):182-97 (2012).
Kortt et al., "Dimeric and trimeric antibodies: high avidity scFvs for cancer targeting," Biomol Eng. 18(3):95-108 (2001) (15 pages).
Law et al., "Expression and characterization of recombinant soluble human CD3 molecules: presentation of antigenic epitopes defined on the native TCR-CD3 complex" Int Immunol 14(4):389-400 (2002).
Leabman et al., "Effects of altered FcγR binding on antibody pharmacokinetics in cynomolgus monkeys, " mAbs. 5(6):896-903 (2013).
Lee et al., "Current concepts in the diagnosis and management of cytokine release syndrome," Blood. 124(2):188-95 (2014) (18 pages).
Li et al., "Exposure-response analyses indicate a promising benefit/risk profile of mosunetuzumab in relapsed and refractory non-Hodgkin lymphoma," 61st Ash Annual Meeting & Exposition (2019) (1 page).
Li, "Successful QSP modeling in drug development starts with the right questions," American Conference on Pharmacometrics 8, Oct. 16, Fort Lauderdale, FL. (2017) (20 pages).
Lippow et al., "Computational Design of Antibody-Affinity Improvement Beyond in Vivo Maturation," available in PMC Jan. 7, 2010, published in final edited form as: Nat Biotechnol. 25(10):1171-6 (2007) (14 pages).
Liu et al., "Affinity-Tuned ErbB2 or EGFR Chimeric Antigen Receptor T Cells Exhibit an Increased Therapeutic Index against Tumors in Mice," Cancer Res. 75(17):3596-607 (2015) (13 pages).
Liu et al., "Heteroantibody duplexes target cells for lysis by cytotoxic T lymphocytes," Proc Natl Acad Sci U S A. 82(24):8648-52 (1985).
Liu et al., "Improvement in soluble expression levels of a diabody by exchanging expression vectors," Protein Expr Purif. 62(1): 15-20 (2008) (6 pages).
Lord et al., "Structure-based engineering to restore high affinity binding of an isoform-selective anti-TGFβ1 antibody," MAbs. 10(3):444-452 (2018) (10 pages).
Lu et al., "Tetravalent anti-CD20/CD3 bispecific antibody for the treatment of B cell lymphoma," Biochem Biophys Res Commun. 473(4):808-813 (May 2016) (Abstract only) (3 pages).
Lum et al., "Targeting T cells with bispecific antibodies for cancer therapy," available in PMC Oct. 8, 2013, published in final edited form as: BioDrugs. 25(6):365-79 (2011) (24 pages).
Mariuzza et al., "The structural basis of antigen-antibody recognition," Annu Rev Biophys Biophys Chem. 16:139-159 (1987) (2 pages) (Abstract only).

(56) References Cited

OTHER PUBLICATIONS

Merchant et al., "An efficient route to human bispecific IgG," Nat Biotechnol. 16(7):677-81 (1998).
Metz et al., "Bispecific antibody derivatives with restricted binding functionalities that are activated by proteolytic processing," Protein Eng Des Sel. 25(10):571-80 (2012).
Milne et al., "Systematic Analysis of Immune Infiltrates in High-Grade Serous Ovarian Cancer Reveals CD20, FoxP3 and TIA-1 as Positive Prognostic Factors," PLoS One. 4(7):e6412 (2009) (14 pages).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
NIH/NCI, "anti-PD-1 fusion protein AMP-224," dated Jul. 10, 2015, accessed Jul. 31, 2019 (1 page).
Nishimoto et al., "Toxicity, pharmacokinetics, and dose-finding study of repetitive treatment with the humanized anti-interleukin 6 receptor antibody MRA in rheumatoid arthritis. Phase I/II clinical study," J Rheumatol. 30(7):1426-35 (2003).
Okazaki et al., "Fucose depletion from human IgG1 oligosaccharide enhances binding enthalpy and association rate between IgG1 and FcgammaRIIIa," J Mol Biol. 336(5):1239-49 (2004).
Olszewski et al., "401 Single-agent mosunetuzumab is a promising safe and efficacious chemotherapy-free regimen for elderly/unfit patients with previously untreated diffuse large B-cell lymphoma," 62nd American Society of Hematology (ASH) Annual Meeting and Exposition, Dec. 5-8, Oral Abstract, <https://ash.confex.com/ash/2020/webprogram/Paper136255.html>, retrieved on Apr. 21, 2022 (2020) (4 pages).
Paino et al., "Reply to 'Response to 'CD20 Positive Cells Are Undetectable in the Majority of Multiple Myeloma Cell Lines and Are Not Associated With a Cancer Stem Cell Phenotype,'" Haematologica. 97(7):1110-1114 (2012) (1 page).
Pessano et al., "The T3/T cell receptor complex: antigenic distinction between the two 20-kd T3 (T3-delta and T3-epsilon) subunits," EMBO J. 4(2):337-44 (1985).
Petkova et al., "Enhanced half-life of genetically engineered human IgG1 antibodies in a humanized FcRn mouse model: potential application in humorally mediated autoimmune disease," Int Immunol. 18(12):1759-69 (2006).
Philips et al., "Therapeutic uses of anti-PD-1 and anti-PD-L1 antibodies," Int Immunol 27(1):39-46 (2014).
Polu et al., "Probody therapeutics for targeting antibodies to diseased tissue," Expert Opin Biol Ther. 14(8):1049-53 (2014).
Ravetch et al., "Fc receptors," Annu Rev Immunol. 9:457-92 (1991).
Reusch et al., "A tetravalent bispecific TandAb (CD19/CD3), AFM11, efficiently recruits T cells for the potent lysis of CD19(+) tumor cells," MAbs. 7(3):584-604 (2015) (22 pages).
Reusch et al., "Anti-CD3 x anti-epidermal growth factor receptor (EGFR) bispecific antibody redirects T-cell cytolytic activity to EGFR-positive cancers in vitro and in an animal model," Clin Cancer Res. 12(1):183-190 (2006) (9 pages).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Ripka et al., "Two Chinese hamster ovary glycosylation mutants affected in the conversion of GDP-mannose to GDP-fucose," Arch Biochem Biophys. 249(2):533-45 (1986).
Roosnek et al., "Triggering T Cells by Otherwise Inert Hybrid Anti-CD3/Antitumor Antibodies Requires Encounter with the Specific Target Cell," J Exp Med. 170(1):297-302 (1989) (6 pages).
Salmerón et al., "A conformational epitope expressed upon association of CD3-epsilon with either CD3-delta or CD3-gamma is the main target for recognition by anti-CD3 monoclonal antibodies," J Immunol. 147(9): 3047-52 (1991) (2 pages) (Abstract only).
Saphire et al., "Crystal structure of a neutralizing human IgG against HIV-1: a template for vaccine design," Science. 293(5532):1155-9 (2001).
Schuster et al., "Immunotherapy with the trifunctional anti-CD20 x anti-CD3 antibody FBTA05 (Lymphomun) in paediatric high-risk patients with recurrent CD20-positive B cell malignancies," Br J Haematol. 169:90-102 (2015) (13 pages).
Schuster et al., "Mosunetuzumab Induces Complete Remissions in Poor Prognosis Non-Hodgkin Lymphoma Patients, Including Those Who Are Resistant to or Relapsing After Chimeric Antigen Receptor T-Cell (CAR-T) Therapies, and Is Active in Treatment through Multiple Lines," Blood. 134(Supplement 1):6 (2019) (5 pages).
Seimetz et al., "Development and approval of the trifunctional antibody catumaxomab (anti-EpCAM x anti-CD3) as a targeted cancer immunotherapy," Cancer Treat Rev. 36(6):458-67 (2010).
Sen et al., "Use of Anti-CD3 x Anti-HER2/neu Bispecific Antibody for Redirecting Cytotoxicity of Activated T Cells Toward HER2/neu$^+$ Tumors," J Hematother Stem Cell Res. 10(2):247-60 (2001).
Shalaby et al., "Bispecific HER2 x CD3 antibodies enhance T-cell cytotoxicity in vitro and localize to HER2-overexpressing xenografts in nude mice," Clin Immunol Immunopathol. 74(2):185-92 (1995).
Shen et al., "Preparation and characterization for bispecific antibodies of anti-CD3 x anti-idiotype to B cell lymphocytic leukemia," J Tongji Med Univ. 19(3):166-9 (1999) (4 pages).
Shi et al., "Margin-Infiltrating CD20$^+$ B Cells Display an Atypical Memory Phenotype and Correlate with Favorable Prognosis in Hepatocellular Carcinoma," Clin Cancer Res. 19(21):5994-6005 (2013) (13 pages).
Shields et al., "High Resolution Mapping of the Binding Site on Human IgG1 for FcγRI, FcγRII, FcγRIII, and FcRn and Design of IgG1 Variants with Improved Binding to the FcγR," J Biol Chem. 276(9):6591-604 (2001).
Somasundaram et al., "Will Engineered T Cells Expressing CD20 scFv Eradicate Melanoma?" Mol Ther. 19(4):638-40 (2011).
Sondermann et al., "The 3.2-A crystal structure of the human IgG1 Fc fragment-FcγRIII complex," Nature. 406(6793):267-73 (2000).
Spiess et al., "Alternative molecular formats and therapeutic applications for bispecific antibodies," Mol Immunol. 67(2 Pt A):95-106, retrieved from <https://www.sciencedirect.com/science/article/pii/S016158901500005X?via%3Dihub> Apr. 5, 2022 (2015) (42 pages).
Spiess et al., "Bispecific antibodies with natural architecture produced by co-culture of bacteria expressing two distinct half-antibodies," Nat Biotechnol. 31(8):753-8 (2013) (7 pages).
Stanglmaier et al., "Bi20 (FBTA05), a novel trifunctional bispecific antibody (anti-CD20 x anti-CD3), mediates efficient killing of B-cell lymphoma cells even with very low CD20 expression levels," Int J Cancer. 123(5):1181-9 (2008).
Stein et al., "Novel and Emerging Drugs for Acute Myeloid Leukemia," available in PMC May 22, 2014, published in final edited form as: Curr Cancer Drug Targets. 12(5):522-530 (2012) (19 pages).
Stieglmaier et al., "Utilizing the BiTE (bispecific T-cell engager) platform for immunotherapy of cancer," Expert Opin Biol Ther. 15(8):1093-9 (2015) (8 pages).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Wakefield et al., "Addition of a C-terminal extension sequence to transforming growth factor-beta 1 interferes with biosynthetic processing and abolishes biological activity," Growth Factors. 5(3):243-53 (1991) (2 pages) (Abstract only).
Wark et al., "Latest technologies for the enhancement of antibody affinity," Adv Drug Deliv Rev. 58(5-6):657-70 (2006).
Weidle et al., "The Intriguing Options of Multispecific Antibody Formats for Treatment of Cancer," Cancer Genomics Proteomics. 10(1):1-18 (2013) (18 pages).
Wells et al., "Reaching for high-hanging fruit in drug discovery at protein-protein interfaces," Nature. 450(7172):1001-9 (2007).

(56) References Cited

OTHER PUBLICATIONS

Westin et al., "Safety and activity of PD1 blockade by pidilizumab in combination with rituximab in patients with relapsed follicular lymphoma: a single group, open-label, phase 2 trial," Lancet Oncol. 15(1):69-77 (2014).
Wright et al., "Effect of glycosylation on antibody function: implications for genetic engineering," Trends Biotechnol. 15(1):26-32 (1997).
Wu et al., "Humanization of a Murine Monoclonal Antibody by Simultaneous Optimization of Framework and CDR Residues," J Mol Biol. 294(1):151-162 (1999).
Wuellner et al., "Bispecific CD3/HER2 Targeting FynomAb Induces Redirected T Cell-Mediated Cytolysis with High Potency and Enhanced Tumor Selectivity," Antibodies. 4(4):426-440 (2015) (15 pages).
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotechnol Bioeng. 87(5):614-22 (2004).
Yan et al., "Succinimide Formation at Asn 55 in the Complementarity Determining Region of a Recombinant Monoclonal Antibody IgG1 Heavy Chain," J Pharm Sci. 98(10):3509-21 (2009).
Yang et al., "Generation and characterization of a target-selectively activated antibody against epidermal growth factor receptor with enhanced anti-tumor potency," MAbs. 7(2):440-50 (2015).
Yang et al., "Improving Trastuzumab's Stability Profile by Removing the Two Degradation Hotspots," J Pharm Sci. 104(6):1960-70 (2015).
"Small data transmission (S2-113410)," IPWireless Inc., SA WG2 Meeting #86, Jul. 11-15, Naantali, Finland, agenda item 9.4 (2011) (6 pages).
Zhu et al., "Engineering high affinity humanized anti-p185HER2/anti-CD3 bispecific F(ab')2 for efficient lysis of p185HER2 overexpressing tumor cells," Int J Cancer. 62(3):319-24 (1995).
Zhu et al., "Identification of heavy chain residues in a humanized anti-CD3 antibody important for efficient antigen binding and T cell activation," J Immunol. 155(4):1903-10 (1995).
Extended European Search Report for European Patent Application No. 20170466.5, dated Sep. 24, 2020 (14 pages).
"History of Changes for Study: NCT02500407: A Safety, Efficacy and Pharmacokinetic Study of BTCT4465A (Mosunetuzumab) as a Single Agent and Combined With Atezolizumab in Non-Hodgkin's Lymphoma (NHL) and Chronic Lymphocytic Leukemia (CLL) ," ClinicalTrials.gov, last updated Mar. 17, 2022, retrieved Jul. 17, 2023, from <https://classic.clinicaltrials.gov/ct2/history/NCT02500407?V_74=View#StudyPageTop> (10 pages).
Audino et al., "Polatuzumab Vedotin, an Antibody-Drug Conjugate Targeting CD79b, Is a Highly Active Agent Against Burkitt Lymphoma and Primary Mediastinal B-Cell Lymphoma," Blood. 134(Supplement 1):3963 (2019) (5 pages).
Auerbach et al., "Angiogenesis assays: problems and pitfalls," Cancer Metastasis Rev. 19(1-2):167-72 (2000).
Bartlett et al., "610 Mosunetuzumab Monotherapy Demonstrates Durable Efficacy with a Manageable Safety Profile in Patients with Relapsed/Refractory Follicular Lymphoma Who Received greater than or equal to 2 Prior Therapies: Updated Results from a Pivotal Phase II Study." American Society of Hematology (ASH) Annual Meeting and Exposition, Dec. 10-13, 2022 (3 pages).
Beans, Carolyn, "Targeting metastasis to halt cancer's spread," PNAS. 115(50):12539-43 (Dec. 1, 2018).
Choi et al, "Reference values of hematology, biochemistry, and blood type in cynomolgus monkeys from cambodia origin," Lab Anim Res. 32(1):46-55 (Mar. 2016).
Curigliano et al., "Safety and Tolerability of Phosphatidylinositol-3-Kinase (PI3K) Inhibitors in Oncology," Drug Safety. 42:247-62 (Jan. 16, 2019).
Dornan et al., "Therapeutic potential of an anti-CD79b antibody-drug conjugate, anti-CD79b-vc-MMAE, for the treatment of non-Hodgkin lymphoma," Blood. 114(13):2721-9 (2009).

Engelberts et al., "DuoBody-CD3xCD20 induces potent T-cell-mediated killing of malignant B cells in preclinical models and provides opportunities for subcutaneous dosing," EBioMedicine 52:102625 (Jan. 2020) (13 pages).
Falchi et al., "An Evidence-based Review of Anti-CD20 Antibody-containing Regimens for the Treatment of Patients With Relapsed or Refractory Chronic Lymphocytic Leukemia, Diffuse Large B-cell Lymphoma, or Follicular Lymphoma," Clin Lymphoma Myeloma Leuk. 18(8):508-18.e14 (May 23, 2018) (25 pages).
Forero-Torres et al., "Polatuzumab Vedotin Combined with Obinutuzumab, Cyclophosphamide, Doxorubicin, and Prednisone (G-CHP) for Patients with Previously Untreated Diffuse Large B-Cell Lymphoma (DLBCL): Preliminary Results of a Phase Ib/II Dose-Escalation Study," Blood. 128(22):1856 (2016) (2 pages).
Gravanis et al., "The changing world of cancer drug development: the regulatory bodies' perspective," Chin Clin Oncol. 3(2):22 (2014) (5 pages).
Gura, "Systems for identifying new drugs are often faulty," Science. 278(5340):1041-2 (1997).
Hait, William, "Anticancer drug development: the grand challenges," Nature Reviews/Drug Discovery. 9(4):253-4 (2010).
Harris et al., "The World Health Organization Classification of Neoplasms of the Hematopoietic and Lymphoid Tissues: Report of the Clinical Advisory Committee Meeting—Airlie House, Virginia, Nov. 1997," The Hematology Journal. 1:53-66 (2000).
Heppner et al., "Tumor heterogeneity: biological implications and therapeutic consequences," Cancer Metastasis Reviews. 2(1):5-23 (1983).
Jain, "Barriers to drug delivery in solid tumors," Sci Am. 271(1):58-65 (1994).
Olszewski et al., "Mosunetuzumab and Polatuzumab Vedotin Demonstrates Preliminary Efficacy in Elderly Unfit/Frail Patients with Previously Untreated Diffuse Large B-Cell Lymphoma," Blood, 142 (Supplement 1): 855 (2023) (3 pages) (Abstract Only).
Shao et al., "Distinguishing Hairy Cell Leukemia Variant from Hairy Cell Leukemia: Development and Validation of Diagnostic Criteria," available in PMC Aug. 30, 2017, published in final edited form as: Leuk Res. 37(4):401-9 (2013) (22 pages).
Sporn et al., "Chemoprevention of cancer," Carcinogenesis. 21(3):525-30 (2000).
Wang, et al., "Fixed Duration Mosunetuzumab Plus Polatuzumab Vedotin Has Promising Efficacy and a Manageable Safety Profile in Patients with BTKi Relapsed/Refractory Mantle Cell Lymphoma: Initial Results from a Phase Ib/II Study," Blood, 142 (Supplement 1): 734 (2023) (3 pages) (Abstract Only).
Xu et al., "Production of bispecific antibodies in 'knobs-into-holes' using a cell-free expression system," MAbs. 7(1):231-42 (Nov. 26, 2014) (13 pages).
Yuraszeck et al., "A quantitative systems pharmacology (QSP) model to assess the action of blinatumomab in NHL patients (pts)," Journal of Clinical Oncology 34(15_suppl) Abstract e14511 (May 20, 2016) (3 pages).
International Preliminary Report on Patentability for International Patent Application No. PCT/US2022/029226, mailed Nov. 23, 2023 (9 pages).
International Search Report and Written Opinion for International Application No. PCT/US2022/029226, dated Aug. 25, 2022 (21 pages).
Office Action for U.S. Appl. No. 17/744,262, dated Nov. 3, 2023 (17 pages).
Budde et al., "Single-Agent Mosunetuzumab Shows Durable Complete Responses in Patients with Relapsed or Refractory B-Cell Lymphomas: Phase I Dose-Escalation Study," J Clin Oncol 40:481-495 (Dec. 2021).
Cleveland Clinic, "Non-Hodgkin Lymphoma" https://my.clevelandclinic.org/health/diseases/15662-non-hodgkin-lymphoma; accessed online Jul. 29, 2024 (15 pages).

* cited by examiner

FIG. 1

Stratify by
- Number of prior lines of therapy (1 vs ≥2)
- Response to last therapy (relapse vs refractory)

2L+ R/R DLBCL
- DLBCL NOS
- Transformed FL
- FL Grade 3B

N=222

→ Randomize 2:1

Arm A (N=148): M + P Q3W
M: 8 cycles
P: 6 cycles

Arm B (N=74): R-GemOx Q2W
(8 cycles)

Primary endpoints: PFS
Key Secondary endpoints: OS, ORR, and CRR

One cycle is 21 days

↓ Polatuzumab vedotin 1.8mg/kg on Day 1 of each cycle up to cycle 6

↓ Mosunetuzumab on Day 1, 8, 15 of Cycle 1
Mosunetuzumab on Day 1 of Cycle 2-8

One cycle is 14 days

↓ Rituximab 375mg/m$^2$ on Day 1 of each cycle
↓ Gemcitabine 1,000mg/m$^2$ on Day 1 of each cycle
↓ Oxaliplatin 100mg/m$^2$ on Day 1 of each cycle

METHODS FOR TREATMENT OF CD20-POSITIVE PROLIFERATIVE DISORDER WITH MOSUNETUZUMAB AND POLATUZUMAB VEDOTIN

CROSS-REFERENCE TO RELATED APPLICATIONS

This application claims benefit of priority to U.S. Provisional Application No. 63/188,695, filed on May 14, 2021, and U.S. Provisional Application No. 63/292,887, filed on Dec. 22, 2021, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on May 5, 2022, is named 50474-269002_Sequence_Listing_5_5_2022_ST25.txt and is 35,336 bytes in size.

FIELD OF THE INVENTION

The present invention relates to the treatment of subjects having a CD20-positive cell proliferative disorder (e.g., a B cell proliferative disorder). More specifically, the invention pertains to combination treatment of subjects having a CD20-positive cell proliferative disorder (e.g., a B cell proliferative disorder; e.g., a non-Hodgkin's lymphoma (NHL); e.g., an aggressive NHL), who may have received at least one line of prior therapy, by subcutaneous administration of mosunetuzumab and intravenous administration of polatuzumab vedotin.

BACKGROUND

Cancers are characterized by the uncontrolled growth of cell subpopulations. Cancers are the leading cause of death in the developed world and the second leading cause of death in developing countries, with over 14 million new cancer cases diagnosed and over eight million cancer deaths occurring each year. Indolent cancers can also severely effect quality of life. Cancer care thus represents a significant and ever-increasing societal burden.

B cell proliferative disorders are a leading cause of cancer-related deaths. For example, non-Hodgkin's lymphoma (NHL) advances quickly and is fatal if untreated. In the United States, B-cell lymphomas constitute approximately 80%-85% of all cases of NHL. Aggressive NHLs include DLBCLs, transformed FLs, and Grade 3b FLs. Up to 40% of patients with DLBCL who are treated in the first-line setting will experience disease progression within 3-4 years (Friedberg J W. *Hematology Am. Soc. Hematol Educ. Program.* 2011, 2011:498-505), and more than half of the patients treated with second-line therapies do not achieve a complete remission (Gisselbrecht C et al. *J. Clin. Oncol.* 2010, 28:4184-4190). Furthermore, since the introduction of the monoclonal anti-CD20 antibody rituximab, it has become more challenging to find effective therapies for the large proportion of patients with R/R DLBCL who have prior exposure to anti-CD20 antibody.

Each year around 3% of FLs transform into higher-grade NHL, most commonly DLBCL (Lossos I S and Gascoyne R D, *Best Pract. Res. Clin. Haematol.* 2011, 24:147-163), leading to almost a third of histologic transformation in 10 years. These patients with DLBCL transformed from a previous FL histology and have been treated with the same standard therapies as high-grade lymphomas. Follicular lymphoma Grade 3b is a distinct subgroup of FL that is more in common genetically, immunophenotypically, and clinically with DLBCL than with other indolent FLs, and the coexistence with DLBCL is frequent (Harris N L and Kluin P. Follicular lymphoma grade 3B: is it a real disease? *Haematologica.* 2011, 96:1244-1246). The clinical course of patients with FL Grade 3b is similar to those with DLBCL, and FL Grade 3b is commonly treated as DLBCL (National Comprehensive Cancer Network. NCCN clinical practice guidelines in oncology. *B-Cell Lymphoma and Prevention and Treatment of Cancer-Related Infections* [resource on the Internet]. 2020. Available from: nccn.org).

Regardless of the biologic and clinical heterogeneity of B-cell lymphomas, subjects with advanced-stage B-cell malignancies are typically treated, initially, with intensive cytotoxic chemotherapy combined with monoclonal antibodies (mAbs) such as the anti-CD20 mAb, rituximab (Rituxan®, MabThera®). Although durable responses can be achieved in some subjects, the majority of subjects will ultimately experience progressive or relapsed disease. NHL remains an incurable disease with currently available therapies. The addition of rituximab to commonly used induction chemotherapy, including cyclophosphamide, doxorubicin, vincristine, and prednisone (CHOP); cyclophosphamide, vincristine, and prednisone (CVP); fludarabine, cyclophosphamide, and mitoxantrone (FCM); bendamustine; or gemcitabine and oxaliplatin (Zelenetz et al. *J. Natl. Compr. Canc. Netw.* 2014, 12(6):916-946; Forstpointner et al. *Blood.* 2006, 108(13): 4003-4008; Mounier et al., *Haematologica.* 2013, 98(11):1726-1731), followed by rituximab maintenance therapy led to prolonged remission and improved subject outcomes. In particular, R-GemOx (rituximab, gemcitabine, and oxaliplatin; see Mounier et al., *Haematologica.* 2013, 98(11):1726-1731) is a recommended regimen in the NCCN Guideline 2021 for subjects with R/R DLBCL who are not candidates for autologous stem cell transplant (ASCT) therapy.

For such subjects, alternative or secondary treatment modalities, such as bispecific antibody-based immunotherapies, may be particularly efficacious. Bispecific antibodies such as mosunetuzumab are capable of simultaneously binding cell surface antigens on cytotoxic cells (e.g., T cells, via binding to CD3) and cancer cells (e.g., B cells, via binding to CD20), with the intent that the bound cytotoxic cell will destroy the bound cancer cell. Antibody drug conjugates are capable of binding to cell-surface epitopes (e.g., targeting CD79b; e.g., polatuzumab vedotin) to promote internalization of the bound drug conjugate for targeted delivery of cytotoxic agents. However, such antibody-based and antibody-drug-conjugate-based immunotherapies may be limited by unwanted effects, including cytokine-driven toxicities (e.g., cytokine release syndrome (CRS)), infusion-related reactions (IRRs), severe tumor lysis syndrome (TLS), and hepatotoxicities.

Thus, there is an unmet need in the field for the development of efficacious methods of combination dosing for the treatment of CD20-positive cell proliferative disorders, including B cell proliferative disorders such as non-Hodgkin's lymphoma (NHL) (e.g., a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma) that achieve a more favorable benefit-risk profile.

SUMMARY OF THE INVENTION

The present invention relates to methods of treating a subject having a CD20-positive cell proliferative disorder (e.g., a B cell proliferative disorder; e.g., a non-Hodgkin's lymphoma (NHL) (e.g., a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma), a chronic lymphoid leukemia (CLL), or a central nervous system lymphoma (CNSL)), by administration of mosunetuzumab and polatuzumab vedotin as a combination therapy. In particular, the present invention relates to methods of treating a subject having an aggressive NHL (e.g., a DLBCL, a transformed FL, or a Grade 3b FL) by subcutaneous administration of mosunetuzumab and intravenous administration of polatuzumab vedotin as a combination therapy.

In one aspect, the invention provides a method of treating a subject having a CD20-positive cell proliferative disorder comprising subcutaneously administering to the subject mosunetuzumab and intravenously administering to the subject polatuzumab vedotin in a dosing regimen comprising at least a first dosing cycle and a second dosing cycle, wherein: (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg (e.g., 5 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 5 mg), the C1D2 of mosunetuzumab is about 15 mg (e.g., 15 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 15 mg) or about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg ±0.75 mg, ±1 mg, ±1.5 mg, ±2 mg, or ±3 mg; e.g., 45 mg), and the C1D3 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein the C2D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg).

In some embodiments, the C1D2 is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg).

In some embodiments, the C1D2 is about 15 mg (e.g., 15 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 15 mg).

In some embodiments, the first dosing cycle is a 21-day (±1 day) dosing cycle. In some embodiments, the C1D1, C1D2, and C1D3 of mosunetuzumab are administered on or about Days 1, 8 (±1 day), and 15 (±1 day), respectively, of the first dosing cycle. In some embodiments, the C1 D1 of polatuzumab vedotin is administered on Day 1 of the first dosing cycle.

In some embodiments, the second dosing cycle is a 21-day (±1 day) dosing cycle. In some embodiments, the C2D1 of mosunetuzumab is administered on Day 1 of the second dosing cycle. In some embodiments, the C2D1 of polatuzumab vedotin is administered on Day 1 of the second dosing cycle.

In some embodiments, the method further comprises one or more additional dosing cycles. In some embodiments, the method comprises four to six additional dosing cycles. In some embodiments, the method comprises six additional dosing cycles. In some embodiments, each additional dosing cycle is a 21-day (±1 day) dosing cycle.

In some embodiments, one or more of the additional dosing cycles comprise an additional single dose of mosunetuzumab and an additional single dose of polatuzumab vedotin. In some embodiments, the additional single dose of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg). In some embodiments, each additional single dose of polatuzumab vedotin is administered to the subject on Day 1 of each additional dosing cycle comprising an additional dose of polatuzumab vedotin. In some embodiments, one or more of the additional dosing cycles comprise an additional single dose of mosunetuzumab and do not comprise administration of polatuzumab vedotin.

In some embodiments, the additional single dose of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg). In some embodiments, each additional single dose of mosunetuzumab is administered to the subject on Day 1 of each additional dosing cycle comprising an additional dose of mosunetuzumab.

In some embodiments, the dosing regimen comprises six additional dosing cycles, wherein each of the six additional dosing cycles comprises a single dose of mosunetuzumab, and wherein no more than four of the six additional dosing cycles comprise administration of polatuzumab vedotin.

In one aspect, the invention features a method of treating a subject having a CD20-positive cell proliferative disorder comprising subcutaneously administering to the subject mosunetuzumab and intravenously administering to the subject polatuzumab vedotin in a dosing regimen comprising eight dosing cycles, wherein: (a) the first dosing cycle comprises: (i) a first dose (C1D1) of mosunetuzumab, a second dose (C1D2) of mosunetuzumab, and a third dose (C1D3) of mosunetuzumab, wherein the C1D1 of mosunetuzumab is about 5 mg (e.g., 5 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 5 mg), the C1D2 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and the C1D3 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg); and (ii) a single dose (C1D1) of polatuzumab vedotin, wherein the C1D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); (b) the second to sixth dosing cycles each comprises a single dose (C2D1-C6D1) of mosunetuzumab and a single dose (C2D1-C6D1) of polatuzumab vedotin, wherein each single dose C2D1-C6D1 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein each single dose C2D1C6D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); and (c) the seventh and eighth dosing cycles each comprises a single dose C7D1 and C8D1, respectively, of mosunetuzumab and does not comprise administration of polatuzumab vedotin, wherein each single dose C7D1 and C8D1 is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg).

In one aspect, the invention features a method of treating a subject having a CD20-positive cell proliferative disorder comprising subcutaneously administering to the subject mosunetuzumab and intravenously administering to the subject polatuzumab vedotin in a dosing regimen comprising eight dosing cycles, wherein: (a) the first dosing cycle comprises: (i) a first dose (C1D1) of mosunetuzumab, a second dose (C1D2) of mosunetuzumab, and a third dose (C1D3) of mosunetuzumab, wherein the C1D1 of mosunetuzumab is about 5 mg (e.g., 5 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 5 mg), the C1D2 of mosunetuzumab is about 15 mg (e.g., 15 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 15 mg), and the C1D3 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg); and (ii) a single dose (C1D1) of polatuzumab vedotin, wherein the C1D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); (b) the second to sixth dosing cycles each comprises a single dose (C2D1-C6D1) of mosunetuzumab and a single dose (C2D1-C6D1) of polatuzumab vedotin, wherein each single dose C2D1-C6D1 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein each single dose C2D1C6D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); and (c) the seventh and eighth dosing cycles each comprises a single dose C7D1 and C8D1, respectively, of mosunetuzumab and does not comprise administration of polatuzumab vedotin, wherein each single dose C7D1 and C8D1 is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg).

In some embodiments, each dosing cycle is a 21-day (±1 day) dosing cycle. In some embodiments, the C1D1, C1D2, and C1D3 of mosunetuzumab are administered on or about Days 1, 8 (±1 day), and 15 (±1 day), respectively, of the first dosing cycle. In some embodiments, each single dose of the C2D1-C8D1 of mosunetuzumab is administered on Day 1 of each respective dosing cycle.

In some embodiments, each single dose of the C1D1-C6D1 of polatuzumab vedotin is administered on Day 1 of each respective dosing cycle.

In some embodiments, the C1D1 of polatuzumab vedotin is administered prior to administration of the C1D1 of mosunetuzumab, and wherein the C2D1 of polatuzumab vedotin is administered prior to administration of the C2D1 of mosunetuzumab. In some embodiments, each single dose C3D1-C6D1 of polatuzumab vedotin is administered prior to administration of each single dose C3D1-C6D1 of mosunetuzumab, respectively. In some embodiments, polatuzumab vedotin is administered at least about 60 minutes prior to administration of mosunetuzumab.

In some embodiments, the method further comprises administering to the subject one or more additional therapeutic agents.

In some embodiments, the one or more additional therapeutic agents is a corticosteroid or an IL-6R antagonist. In some embodiments, the one or more additional therapeutic agents is an IL-6R antagonist. In some embodiments, the IL-6R antagonist is tocilizumab. In some embodiments, tocilizumab is administered to the subject as a single dose of about 8 mg/kg (e.g., 8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, ±1 mg/kg, ±1.5 mg/kg, or ±2 mg/kg; e.g., 8 mg/kg), and wherein the single dose does not exceed 800 mg. In some embodiments, tocilizumab is administered to the subject as a single dose of about 12 mg/kg (e.g., 12 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, ±1 mg/kg, ±1.5 mg/kg, or ±2 mg/kg; e.g., 12 mg/kg), and wherein the single dose does not exceed 800 mg. In some embodiments, tocilizumab is administered intravenously.

In some embodiments, the one or more additional therapeutic agents is a corticosteroid. In some embodiments, the corticosteroid is dexamethasone, prednisone, or methylprednisolone.

In some embodiments, the corticosteroid is dexamethasone. In some embodiments, dexamethasone is administered as a single dose of about 10 mg (e.g., 10 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 10 mg) every 6 hours. In some embodiments, dexamethasone is administered intravenously. In some embodiments, dexamethasone is administered as a single dose of about 20 mg (e.g., 20 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 20 mg) prior to administration of any dose of mosunetuzumab. In some embodiments, dexamethasone is administered orally.

In some embodiments, the corticosteroid is methylprednisolone. In some embodiments, methylprednisolone is administered at a dose of about 1000 mg/day (e.g., 1000 mg/day±1 mg/day, ±2.5 mg/day, ±5 mg/day, ±7.5 mg/day, ±10 mg/day, ±20 mg/day, ±30 mg/day, ±40 mg/day, ±50 mg/day, ±75 mg/day, ±100 mg/day, ±150 mg/day, ±200 mg/day, or ±300 mg/day; e.g., 1000 mg/day). In some embodiments, methylprednisolone is administered intravenously.

In some embodiments, the corticosteroid is prednisone. In some embodiments, prednisone is administered at a dose of about 10-30 mg/day (e.g., about 10 mg/day, about 11 mg/day, about 12 mg/day, about 13 mg/day, about 14 mg/day, about 15 mg/day, about 16 mg/day, about 17 mg/day, about 18 mg/day, about 19 mg/day, about 20 mg/day, about 21 mg/day, about 22 mg/day, about 23 mg/day, about 24 mg/day, about 25 mg/day, about 26 mg/day, about 27 mg/day, about 28 mg/day, about 29 mg/day, or about 30 mg/day; e.g., 10 mg/day, 11 mg/day, 12 mg/day, 13 mg/day, 14 mg/day, 15 mg/day, 16 mg/day, 17 mg/day, 18 mg/day, 19 mg/day, 20 mg/day, 21 mg/day, 22 mg/day, 23 mg/day, 24 mg/day, 25 mg/day, 26 mg/day, 27 mg/day, 28 mg/day, 29 mg/day, or 30 mg/day). In some embodiments, prednisone is administered orally.

In some embodiments, the one or more additional therapeutic agents is acetaminophen or paracetamol. In some embodiments, acetaminophen or paracetamol is administered as a single dose of about 500-1000 mg (e.g., about 500 mg, about 550 mg, about 600 mg, about 650 mg, about 700 mg, about 750 mg, about 800 mg, about 850 mg, about 900 mg, about 950 mg, or about 1000 mg; e.g., 500 mg, 550 mg, 600 mg, 650 mg, 700 mg, 750 mg, 800 mg, 850 mg, 900 mg, 950 mg, or 1000 mg) prior to administration of any dose of polatuzumab vedotin. In some embodiments, acetaminophen or paracetamol is administered orally.

In some embodiments, the one or more additional therapeutic agents is diphenhydramine. In some embodiments, diphenhydramine is administered as a single dose of about 50-100 mg (e.g., about 50 mg, about 55 mg, about 60 mg, about 65 mg, about 70 mg, about 75 mg, about 80 mg, about 85 mg, about 90 mg, about 95 mg, or about 100 mg; e.g., 50 mg, 55 mg, 60 mg, 65 mg, 70 mg, 75 mg, 80 mg, 85 mg, 90 mg, 95 mg, or 100 mg) prior to administration of any dose of polatuzumab vedotin. In some embodiments, diphenhydramine is administered orally.

In some embodiments, the CD20-positive cell proliferative disorder is a B cell proliferative disorder. In some embodiments, the B cell proliferative disorder is a non-Hodgkin's lymphoma (NHL), a chronic lymphoid leukemia (CLL), or a central nervous system lymphoma (CNSL).

In some embodiments, the NHL is a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma. In some embodiments, the NHL is a relapsed and/or refractory (R/R) NHL.

In some embodiments, the NHL is a DLBCL. In some embodiments, the DLBCL is an R/R DLBCL. In some embodiments, the DLBCL is a Richter's transformation.

In some embodiments, the NHL is an FL (e.g., a Grade 1, 2, 3a, or 3b FL). In some embodiments, the FL is an R/R FL. In some embodiments, the FL is a transformed FL. In some embodiments, the FL is a Grade 3b FL.

In some embodiments, the NHL is a HGBL. In some embodiments, the HGBL is an R/R HGBL.

In some embodiments, the NHL is an aggressive NHL. In some embodiments, the aggressive NHL is a DLBCL, a transformed FL, or a Grade 3b FL. In some embodiments, the aggressive NHL is an R/R NHL.

In some embodiments, the subject is ineligible for autologous stem cell transplant (ASCT).

In some embodiments, the subject has relapsed after or is refractory to two or more (e.g., two, three, four, five, six, seven, eight, nine, ten, or more) prior lines of therapy.

In some embodiments, the subject is human.

In one aspect, the invention features a method of treating a population of subjects having a CD20-positive cell proliferative disorder comprising subcutaneously administering to the subjects of the population mosunetuzumab and intravenously administering to the subjects of the population polatuzumab vedotin in a dosing regimen comprising at least a first dosing cycle and a second dosing cycle, wherein: (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg (e.g., 5 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 5 mg), the C1D2 of mosunetuzumab is about 15 mg (e.g., 15 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 15 mg) or about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and the C1D3 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein the C1D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); and (b) the second dosing cycle comprises a single dose (C2D1) of mosunetuzumab and a single dose (C2D1) of polatuzumab vedotin, wherein the C2D1 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein the C2D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg).

In one aspect, the invention features a method of treating a population of subjects having a CD20-positive cell proliferative disorder comprising subcutaneously administering to the subjects of the population mosunetuzumab and intravenously administering to the subjects of the population polatuzumab vedotin in a dosing regimen comprising eight dosing cycles, wherein: (a) the first dosing cycle comprises: (i) a first dose (C1D1) of mosunetuzumab, a second dose (C1D2) of mosunetuzumab, and a third dose (C1D3) of mosunetuzumab, wherein the C1 D1 of mosunetuzumab is about 5 mg (e.g., 5 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 5 mg), the C1D2 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and the C1D3 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg); and (ii) a single dose (C1D1) of polatuzumab vedotin, wherein the C1D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); (b) the second to sixth dosing cycles each comprises a single dose (C2D1-C6D1) of mosunetuzumab and a single dose (C2D1-C6D1) of polatuzumab vedotin, wherein each single dose C2D1-C6D1 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein each single dose C2D1C6D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); and (c) the seventh and eighth dosing cycles each comprises a single dose C7D1 and C8D1, respectively, of mosunetuzumab and does not comprise administration of polatuzumab vedotin, wherein each single dose C7D1 and C8D1 is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg).

In some embodiments, the average duration of progression-free survival of the population of subjects is higher than a reference average duration of progression-free survival of a reference population of subjects.

In some embodiments, the complete response rate in the population of subjects is higher than a reference complete response rate in a reference population of subjects.

In some embodiments, the objective response rate in the population of subjects is higher than a reference objective response rate in a reference population of subjects.

In some embodiments, the average duration of response of the population of subjects is higher than a reference average duration of response of a reference population of subjects.

In some embodiments, the average duration of complete response of the population of subjects is higher than a reference average duration of complete response of a reference population of subjects.

In some embodiments, the reference population of subjects is administered a combination therapy comprising rituximab, gemcitabine, and oxaliplatin. In some embodiments, the combination therapy is administered to the reference population of subjects in a dosing cycle comprising eight dosing cycles. In some embodiments, each dosing cycle is a 14-day (±1 day) dosing cycle. In some embodiments, the combination therapy is administered to the reference population of subjects about every two weeks (Q2W). In some embodiments, rituximab is administered intravenously at a dose of about 375 mg/m$^2$ (e.g., 375 mg/m$^2$±1 mg/m$^2$, ±2.5 mg/m$^2$, ±5 mg/m$^2$, ±7.5 mg/m$^2$, ±10 mg/m$^2$, ±20 mg/m$^2$, ±30 mg/m$^2$, ±40 mg/m$^2$, or ±50 mg/m$^2$; e.g., 375 mg/m$^2$) Q2W, gemcitabine is administered intravenously at a dose of about 1000 mg/m$^2$ Q2W (e.g., 1000 mg/m$^2$±1 mg/m$^2$, ±2.5 mg/m$^2$, ±5 mg/m$^2$, ±7.5 mg/m$^2$, ±10 mg/m$^2$, ±20 mg/m$^2$, ±30 mg/m$^2$, ±40 mg/m$^2$, ±50 mg/m$^2$; ±100 mg/m$^2$; ±150 mg/m$^2$; ±200 mg/m$^2$; ±250 mg/m$^2$; ±300 mg/m$^2$; e.g., 1000 mg/m$^2$), and oxaliplatin is administered intravenously at a dose of about 100 mg/m$^2$ (e.g., 100 mg/m$^2$±1 mg/m$^2$, ±2.5 mg/m$^2$, ±5 mg/m$^2$, ±7.5 mg/m$^2$, ±10 mg/m$^2$, ±20 mg/m$^2$, or ±30 mg/m$^2$; e.g., 100 mg/m$^2$) Q2W.

In some embodiments, the CD20-positive cell proliferative disorder is a B cell proliferative disorder. In some embodiments, the B cell proliferative disorder is a non-Hodgkin's lymphoma (NHL), a chronic lymphoid leukemia (CLL), or a central nervous system lymphoma (CNSL).

In some embodiments, the NHL is a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma. In some embodiments, the NHL is a relapsed and/or refractory (R/R) NHL.

In some embodiments, the NHL is a DLBCL. In some embodiments, the DLBCL is an R/R DLBCL. In some embodiments, the DLBCL is a Richter's transformation.

In some embodiments, the NHL is an FL (e.g., a Grade 1, 2, 3a, or 3b FL). In some embodiments, the FL is an R/R FL. In some embodiments, the FL is a transformed FL. In some embodiments, the FL is a Grade 3b FL.

In some embodiments, the NHL is a HGBL. In some embodiments, the HGBL is an R/R HGBL.

In some embodiments, the NHL is an aggressive NHL. In some embodiments, the aggressive NHL is a DLBCL, a transformed FL, or a Grade 3b FL. In some embodiments, the aggressive NHL is an R/R NHL.

In some embodiments, each subject in the population of subjects is ineligible for autologous stem cell transplant (ASCT). In some embodiments, each subject in the population of subjects has relapsed after or is refractory to two or more prior lines of therapy. In some embodiments, each subject in the population of subjects is human.

In some embodiments, each subject in the reference population of subjects is ineligible for autologous stem cell transplant (ASCT). In some embodiments, each subject in the reference population of subjects has relapsed after or is refractory to two or more prior lines of therapy. In some embodiments, each subject in the reference population of subjects is human.

BRIEF DESCRIPTION OF THE DRAWINGS

FIG. 1 is a schematic of the study design described in Example 1. 2L=second-line; DLBCL=diffuse large B cell lymphoma; CRR=complete response rate; FL=follicular lymphoma; M=mosunetuzumab; NOS=not otherwise specified; OS=overall survival; ORR=objective response rate; P=polatuzumab vedotin; PFS=progression-free survival; Q2W=every 2 weeks (i.e., 14-day dosing cycles); Q3W=every 3 weeks (i.e., 21-day dosing cycles); R GemOx=rituximab, gemcitabine, and oxaliplatin; R/R=relapsed and/or refractory.

DETAILED DESCRIPTION

Figure 2A:
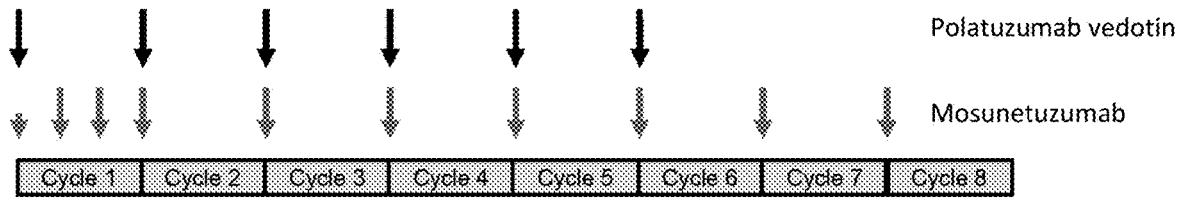
FIG. 2A is a schematic of the dosing regimen of Arm A (mosunetuzumab+polatuzumab vedotin arm) described in Example 1. Treatment comprises eight total dosing cycles (Cycles 1-8). Mosunetuzumab is administered with the following doses and timings: 5 mg subcutaneously on Cycle 1, Day 1; 45 mg on Cycle 1, Day 8; Cycle 1, Day 15; and Day 1 of Cycles 2-8. Polatuzumab vedotin is administered intravenously with the following dose and timing: 1.8 mg/kg on Day 1 of Cycles 1-6. Each dosing cycle is 21 days.

The present invention relates to methods of treating a subject or a population of subjects having a CD20-positive cell proliferative disorder (e.g., a B cell proliferative disorder; e.g., a non-Hodgkin's lymphoma (NHL) (e.g., a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma), a chronic lymphoid leukemia (CLL), or a central nervous system lymphoma (CNSL)), by administration of mosunetuzumab and polatuzumab vedotin as a combination therapy. In particular, the present invention relates to methods of treating a subject or a population of subjects having an aggressive NHL (e.g., a DLBCL, a transformed FL, or a Grade 3b FL) by subcutaneous administration of mosunetuzumab and intravenous administration of polatuzumab vedotin as a combination therapy.

The invention is based, in part, on the discovery that combination therapy involving subcutaneous administration of mosunetuzumab and intravenous administration of polatuzumab vedotin over multiple dosing cycles (e.g., wherein the first dosing cycle is a step-up, fractionated dosing cycle) can effectively treat a subject or a population of subjects having a CD20-positive cell proliferative disorder (e.g., a B cell proliferative disorder; e.g., a non-Hodgkin's lymphoma (NHL) (e.g., a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma), a chronic lymphoid leukemia (CLL), or a central nervous system lymphoma (CNSL)), in particular those who have an aggressive NHL (e.g., a DLBCL, a transformed FL, or a Grade 3b FL) and/or who are relapsed and/or refractory (R/R) to at least one line of prior therapy, while maintaining an acceptable safety profile (e.g., with respect to frequency and severity of adverse events, such as cytokine release syndrome (CRS)). In some instances, the subject or the population of subjects may have received two or more lines of prior therapy. In some instances, the subject or the population of subjects may be ineligible for autologous stem cell transplant (ASCT).

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

II. Definitions

It is to be understood that aspects and embodiments of the invention described herein include "comprising," "consisting," and "consisting essentially of" aspects and embodiments.

As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se.

The terms "cancer" and "cancerous" refer to or describe the physiological condition in mammals that is typically characterized by unregulated cell growth. Examples of cancer include, but are not limited to, hematologic cancers, such as mature B cell cancers, excluding Hodgkin's lymphoma, but including non-Hodgkin's lymphoma (NHL), such as diffuse large B cell lymphoma (DLBCL), which may be relapsed and/or refractory DLBCL or a Richter's transformation. Other specific examples of cancer also include germinal-center B cell-like (GCB) diffuse large B cell lymphoma (DLBCL), activated B cell-like (ABC) DLBCL, follicular lymphoma (FL), transformed FL, mantle cell lymphoma (MCL), acute myeloid leukemia (AML), chronic lymphoid leukemia (CLL), marginal zone lymphoma (MZL), transformed MZL, high grade B-cell lymphoma, primary mediastinal (thymic) large B cell lymphoma (PMLBCL), small lymphocytic leukemia (SLL), lymphoplasmacytic lymphoma (LL), transformed LL, Waldenstrom macroglobulinemia (WM), central nervous system lymphoma (CNSL), Burkitt's lymphoma (BL), B cell prolymphocytic leukemia, splenic marginal zone lymphoma, hairy cell leukemia, splenic lymphoma/leukemia, unclassifiable, splenic diffuse red pulp small B cell lymphoma, hairy cell leukemia variant, heavy chain diseases, α heavy chain disease, γ heavy chain disease, μ heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, primary cutaneous follicle center lymphoma, T cell/histiocyte rich large B cell lymphoma, primary DLBCL of the CNS, primary cutaneous DLBCL, leg type, EBV-positive DLBCL of the elderly, DLBCL associated with chronic inflammation, lymphomatoid granulomatosis, intravascular large B cell lymphoma, ALK-positive large B cell lymphoma, plasmablastic lymphoma, large B cell lymphoma arising in HHV8-associated multicentric Castleman disease, primary effusion lymphoma: B cell lymphoma, unclassifiable, with features intermediate between DLBCL and Burkitt lymphoma, and B cell lymphoma, unclassifiable, with features intermediate between DLBCL and classical Hodgkin's lymphoma. Further examples of cancer include, but are not limited to, carcinoma, lymphoma, blastoma, sarcoma, and leukemia or lymphoid malignancies, including B cell lymphomas. More particular examples of such cancers include, but are not limited to, multiple myeloma (MM); low-grade/follicular NHL; small lymphocytic (SL) NHL; intermediate-grade/follicular NHL; intermediate-grade diffuse NHL; high-grade immunoblastic NHL; high-grade lymphoblastic NHL; high-grade small non-cleaved cell NHL; bulky disease NHL; AIDS-related lymphoma; and acute lymphoblastic leukemia (ALL); chronic myeloblastic leukemia; and post-transplant lymphoproliferative disorder (PTLD).

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In another embodiment, the cell proliferative disorder is a tumor.

The terms "B cell proliferative disorder" or "B cell malignancy" refer to disorders that are associated with some degree of abnormal B cell proliferation and include, for example, lymphomas, leukemias, myelomas, and myelodysplastic syndromes. In some instances, the B cell proliferative disorder is a lymphoma, such as non-Hodgkin's lymphoma (NHL), including, for example, follicular lymphoma (FL) (e.g., a relapsed and/or refractory FL or transformed FL (trFL)), diffuse large B cell lymphoma (DLBCL) (e.g., a relapsed and/or refractory DLBCL or a Richter's transformation), mantle cell lymphoma (MCL), high grade B-cell lymphoma (HGBL), primary mediastinal (thymic) large B-cell lymphoma (PMLBCL), diffuse B cell lymphoma, small lymphocytic lymphoma, marginal zone lymphoma (MZL), Burkitt lymphoma, or lymphoplasmacytic lymphoma. In another embodiment, the B cell proliferative disorder is a leukemia, such as chronic lymphocytic leukemia (CLL). In one embodiment, the B-cell proliferative disorder is relapsed and/or refractory. In some embodiments, an NHL may be an aggressive NHL (aNHL). An "aggressive" NHL grows and spreads quickly, usually accompanied by severe symptoms, as opposed to an "indolent" NHL which tends to grow and spread slowly, manifesting with few symptoms. Examples of aNHL include, e.g., HGBL, DLBCL, trFL, and Grade 3b FL (see Swerdlow S H, et al. *Blood* 2016; 127:2375-90).

"Refractory disease" is defined as no complete remission to at least a first-line therapy. In one embodiment, refractory disease defined as no response to or relapse within 6 months of prior therapy. In one embodiment, refractory disease is characterized by one or more of the following: progressive disease (PD) as best response to first-line therapy, stable disease (SD) as best response after at least one first line therapy, or partial response (PR) as best response, and biopsy-proven residual disease or disease progression after the partial response. "Relapsed disease" is defined as complete remission to first-line therapy. In one embodiment, disease relapse is proven by biopsy. In one embodiment, subjects have relapsed after or failed to respond to at least one prior systemic treatment regimen.

As used herein, "treatment" (and grammatical variations thereof, such as "treat" or "treating") refers to clinical intervention in an attempt to alter the natural course of the subject being treated, and can be performed either for prophylaxis or during the course of clinical pathology. Desirable effects of treatment include, but are not limited to, preventing recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies and antibody drug conjugates of the invention are used to delay development of a disease or to slow the progression of a disease.

As used herein, "delaying progression" of a disorder or disease means to defer, hinder, slow, retard, stabilize, and/or postpone development of the disease or disorder (e.g., a CD20-positive cell proliferative disorder). This delay can be of varying lengths of time, depending on the history of the disease and/or individual being treated. As is evident to one skilled in the art, a sufficient or significant delay can, in effect, encompass prevention, in that the individual does not develop the disease. For example, a late-stage cancer, such as development of metastasis, may be delayed.

By "reduce" or "inhibit" is meant the ability to cause an overall decrease, for example, of 20%, 30%, 40%, 50%, 60%, 70%, 75%, 80%, 85%, 90%, 95%, or greater. For clarity the term includes also reduction to zero (or below the detection limit of the analytical method), i.e., complete abolishment or elimination. In certain embodiments, reduce or inhibit can refer to the reduction or inhibition of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities, following treatment with mosunetuzumab using the step-up dosing regimen of the invention relative to unchanging, preset dosing with the target dose of mosunetuzumab. In other embodiments, reduce or inhibit can refer to effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP). In other embodiments reduce or inhibit can refer to the symptoms of the CD20-positive cell proliferative disorder (e.g., the B cell proliferative disorder) being treated, the presence or size of metastases, or the size of the primary tumor. In yet other embodiments, reducing or inhibiting cancer relapse means to reduce or inhibit tumor or cancer relapse, or tumor or cancer progression.

As used herein, "administering" is meant a method of giving a dosage of a compound (e.g., a bispecific antibody (e.g., mosunetuzumab) and/or an antibody drug conjugate (e.g., polatuzumab vedotin)) or a composition (e.g., a pharmaceutical composition, e.g., a pharmaceutical composition including a bispecific antibody (e.g., mosunetuzumab) and/or an antibody drug conjugate (e.g., polatuzumab vedotin)) to a subject. The compounds and/or compositions utilized in the methods described herein can be administered subcutaneously (e.g., by subcutaneous injection) or intravenously (e.g., by intravenous infusion).

A "fixed" or "flat" dose of a therapeutic agent (e.g., a bispecific antibody (e.g., mosunetuzumab) or an antibody drug conjugate (e.g., polatuzumab vedotin)) herein refers to a dose that is administered to a subject without regard for the weight or body surface area (BSA) of the subject. The fixed or flat dose is therefore not provided as a mg/kg dose or a mg/m$^2$ dose, but rather as an absolute amount of the therapeutic agent (e.g., mg).

A "subject" or an "individual" is a mammal. Mammals include, but are not limited to, primates (e.g., humans and non-human primates such as monkeys), domesticated animals (e.g., cows, sheep, cats, dogs, and horses), rabbits, and rodents (e.g., mice and rats). In particular embodiments, the subject or individual is a human. In particular embodiments, the subjects or individuals of a population are human.

A "reference population," e.g., a "reference population of subjects," as used herein, refers to a population (e.g., a population of subjects) that is used for comparison purposes. In some embodiments, a reference population of subjects comprises subjects having a CD20-positive cell proliferative disorder (e.g., a B cell proliferative disorder; e.g., a non-Hodgkin's lymphoma (NHL) (e.g., a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma), a chronic lymphoid leukemia (CLL), or a central nervous system lymphoma (CNSL)), e.g., subjects who have an aggressive NHL (e.g., a DLBCL, a transformed FL, or a Grade 3b FL) and/or who are relapsed and/or are refractory to (R/R) to at least one line of prior therapy. In some embodiments, the reference population of subjects are ineligible for autologous stem cell transplant (ASCT) treatment or are R/R to at least two lines of prior therapy. In some embodiments, a reference population of subjects is treated with R-GemOx. In some embodiments, a reference population of subjects has received treatment with R-GemOx. In some embodiments, a reference population of subjects does not comprise any subjects who are treated with or who have received treatment with mosunetuzumab and/or polatuzumab vedotin. In some embodiments, a reference population of subjects is not treated with and has not received treatment with mosunetuzumab and/or polatuzumab vedotin. Furthermore, one of skill in the art understands "reference population" in the context of the objective(s) of the comparisons being made. For example, in some embodiments, a reference population is an untreated population having a CD20-positive cell proliferative disorder, while in other embodiments, the reference population is a population having a CD20-positive cell proliferative disorder who have been previously treated with at least two lines of prior therapy.

"Individual response" or "response" can be assessed using any endpoint indicating a benefit to the subject, including, without limitation, (1) inhibition, to some extent, of disease progression (e.g., progression of a CD20-positive cell proliferative disorder (e.g., a B cell proliferative disorder), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e., reduction, slowing down or complete stopping) of metastasis; (5) relief, to some extent, of one or more symptoms associated with the CD20-positive cell proliferative disorder (e.g., the B cell proliferative disorder); (6) increase or extend in the length of survival, including overall survival and progression-free survival; and/or (9) decreased mortality at a given point of time following treatment.

As used herein, "complete response" or "CR" refers to disappearance of all target lesions (i.e., all evidence of disease).

As used herein, "partial response" or "PR" refers to at least a 30% decrease in the sum of the longest diameters (SLD) of target lesions, taking as reference the baseline SLD, or at least a 50% decrease in the sum of the product of the diameters (SPD) of target lesions, taking as reference the baseline SPD.

As used herein, "objective response rate" (ORR) refers to the sum of complete response (CR) rate and partial response (PR) rate.

As used herein, "duration of objective response" (DOR) is defined as the time from the first occurrence of a documented objective response to disease progression, or death from any cause within 30 days of the last dose of a treatment, whichever occurs first.

As used herein, "tumor burden" refers to the total amount of tumor (e.g., tumor cells or tumor mass) in a subject (e.g., a human subject) having a cancer, e.g., a CD20-positive cell proliferative disorder (e.g., a B cell proliferative disorder). In some embodiments, tumor burden is defined as the sum of diameters of target lesions or the sum of the product of target lesions. In a particular embodiment, tumor burden is defined as the sum of the product of the diameters of (SPD) target lesions. In some embodiments, the diameter of target lesions is quantified by computed tomography (CT).

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

An "effective response" of a subject or a subject's "responsiveness" to treatment with a medicament and similar wording refers to the clinical or therapeutic benefit imparted to a subject as risk for, or suffering from, a disease or disorder, such as cancer. In one embodiment, such benefit includes any one or more of: extending survival (including overall survival and progression free survival); resulting in an objective response (including a complete response or a partial response); or improving signs or symptoms of cancer.

A subject who "does not have an effective response" to treatment refers to a subject who does not have any one of extending survival (including overall survival and progression free survival); resulting in an objective response (including a complete response or a partial response); or improving signs or symptoms of cancer.

As used herein, "survival" refers to the subject remaining alive, and includes overall survival as well as progression-free survival.

As used herein, "overall survival" (OS) refers to the percentage of subjects in a group who are alive after a particular duration of time, e.g., 1 year or 5 years from the time of diagnosis or treatment.

As used herein, "progression-free survival" (PFS) refers to the length of time during and after treatment during which the disease being treated (e.g., a CD20-positive cell proliferative disorder (e.g., a B cell proliferative disorder)) does not get worse. Progression-free survival may include the amount of time subjects have experienced a complete response or a partial response, as well as the amount of time subjects have experienced stable disease.

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD, or at least a 50% increase in the SPD of target legions, taking as reference the smallest SPD, recorded since the treatment started or the presence of one or more new lesions.

As used herein, "delaying progression" of a disorder or disease means to defer, hinder, slow, retard, stabilize, and/or postpone development of the disease or disorder (e.g., a CD20-positive cell proliferative disorder (e.g., a B cell proliferative disorder)). This delay can be of varying lengths of time, depending on the history of the disease and/or subject being treated. As is evident to one skilled in the art, a sufficient or significant delay can, in effect, encompass prevention, in that the subject does not develop the disease. For example, in a late-stage cancer, development of central nervous system (CNS) metastasis, may be delayed.

By "extending survival" is meant increasing overall or progression free survival in a treated subject relative to an untreated subject (e.g., relative to a subject not treated with the medicament), or relative to a subject who does not express a biomarker at the designated level, and/or relative to a subject treated with an approved anti-tumor agent. An objective response refers to a measurable response, including complete response (CR) or partial response (PR).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

The terms "full-length antibody," "intact antibody," and "whole antibody" are used herein interchangeably to refer to an antibody having a structure substantially similar to a native antibody structure or having heavy chains that contain an Fc region as defined herein.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'$_2$, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term IgG "isotype" or "subclass" as used herein is meant any of the subclasses of immunoglobulins defined by the chemical and antigenic characteristics of their constant regions.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "variable region" or "variable domain" refers to the domain of an antibody heavy or light chain that is involved in binding the antibody (i.e., mosunetuzumab) to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

The term an "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For a review of methods for assessment of antibody purity, see, e.g., Flatman et al., *J. Chromatogr. B* 848:79-87 (2007). In preferred embodiments, the antibody (i.e., mosunetuzumab) will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody (i.e., mosunetuzumab) as being obtained from a substantially homogeneous population of antibodies, and is not to be construed as requiring production of the antibody by any particular method. For example, the monoclonal antibodies (i.e., mosunetuzumab) to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (K)). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant (K)) of $\leq 1$ µM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). In certain embodiments, an anti-CD3 antibody binds to an epitope of CD3 that is conserved among CD3 from different species.

The term "cluster of differentiation 3" or "CD3," as used herein, refers to any native CD3 from any vertebrate source, including mammals such as primates (e.g., humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI Ref Seq No. NP_000724), which is 207 amino acids in length, and human CD3γ protein (NCBI Ref Seq No. NP_000064), which is 182 amino acids in length.

The terms "anti-CD20 antibody" and "an antibody that binds to CD20" refer to an antibody that is capable of binding CD20 with sufficient affinity such that the antibody is useful as a diagnostic and/or therapeutic agent in targeting CD20. In one embodiment, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant ($K_D$) of $\leq 1$ µM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). In certain embodiments, an anti-CD20 antibody binds to an epitope of CD20 that is conserved among CD20 from different species. In some embodiments, the anti-CD20 antibody is a monoclonal antibody. In some embodiments, the anti-CD20 antibody or anti-CD20 monoclonal antibody is rituximab. In some embodiments, the anti-CD20 antibody or anti-CD20 monoclonal antibody is obinutuzumab.

As used herein, the term "rituximab" or "RITUXAN®" refers to an anti-CD20 antibody (e.g., anti-CD20 monoclonal antibody) having the Proposed International Nonproprietary Names for Pharmaceutical Substances (Proposed INN) List 77 (WHO Drug Information, Vol. 11, No. 2, 1997, p. 99), or the CAS Registry Number 174722-31-7.

As used herein, the term "obinutuzumab" or "GAZYVA®" refers to an anti-CD20 antibody (e.g., anti-CD20 monoclonal antibody) having the Proposed International Nonproprietary Names for Pharmaceutical Substances (Proposed INN) List 99 (WHO Drug Information, Vol. 22, No. 2, 2008, p. 396), Proposed International Nonproprietary Names for Pharmaceutical Substances (Proposed INN) List 108 (WHO Drug Information, Vol. 26, No. 4, 2012, p. 453), or the CAS Registry Number 949142-50-1.

The term "cluster of differentiation 20" or "CD20," as used herein, refers to any native CD20 from any vertebrate source, including mammals such as primates (e.g., humans) and rodents (e.g., mice and rats), unless otherwise indicated. The term encompasses "full-length," unprocessed CD20, as well as any form of CD20 that results from processing in the cell. The term also encompasses naturally occurring variants of CD20, including, for example, splice variants or allelic variants. CD20 includes, for example, human CD20 protein (see, e.g., NCBI Ref Seq Nos. NP_068769.2 and NP_690605.1), which is 297 amino acids in length and may be generated, for example, from variant mRNA transcripts that lack a portion of the 5' UTR (see, e.g., NCBI Ref Seq No. NM_021950.3) or longer variant mRNA transcripts (see, e.g., NCBI Ref Seq No. NM_152866.2).

The terms "anti-CD20/anti-CD3 bispecific antibody," "bispecific anti-CD20/anti-CD3 antibody," and "antibody that binds to CD20 and CD3," or variants thereof, refer to mosunetuzumab.

As used herein, the term "mosunetuzumab" refers to an anti-CD20/anti-CD3 bispecific antibody having the International Nonproprietary Names for Pharmaceutical Substances (INN) List 117 (WHO Drug Information, Vol. 31, No. 2, 2017, p. 303), or the CAS Registry Number 1905409-39-3.

The terms "anti-CD79b antibody" and "an antibody that binds to CD79b" refer to an antibody that is capable of binding CD79b with sufficient affinity such that the antibody is useful as a diagnostic and/or therapeutic agent in targeting CD79b. In one embodiment, the extent of binding of an anti-CD79b antibody to an unrelated, non-CD79b protein is less than about 10% of the binding of the antibody to CD79b as measured, e.g., by a radioimmunoassay (RIA). In certain embodiments, an antibody that binds to CD79b has a dissociation constant ($K_D$) of $\leq 1$ µM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, or e.g., from $10^{-9}$ M to $10^{-13}$ M). In certain embodiments, an anti-CD79b antibody binds to an epitope of CD79b that is conserved among CD79b from different species. As used herein, an anti-CD79b antibody is polatuzumab.

As used herein, the term "polatuzumab vedotin" refers to an antibody drug conjugate comprising an anti-CD79b antibody conjugated to monomethyl auristatin E (MMAE, i.e., vedotin). Polatuzumab vedotin is also referred to as IUPHAR/BPS Number 8404, the KEGG Number D10761, or by the CAS Registry Number 1313206-42-6. Polatuzumab vedotin-piiq is also interchangeably referred to as "polatuzumab vedotin-piiq", "huMA79bv28-MC-vc-PAB-MMAE", or "DCDS4501A."

As used herein, the term "binds," "specifically binds to," or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, for example, by a radioimmunoassay (RIA). In certain embodiments, an antibody that specifically binds to a target has a dissociation constant ($K_D$) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding. The term as used herein can be exhibited, for example, by a molecule having a $K_D$ for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a $K_D$ in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and $K_D$ values are inversely related. A high affinity for an antigen is measured by a low $K_D$ value. In one embodiment, the term "specific binding" refers to binding where a molecule binds to a particular polypeptide or epitope on a particular polypeptide without substantially binding to any other polypeptide or polypeptide epitope.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN® (DNASTAR®) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX® operating system, including digital UNIX® V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the term "chemotherapeutic agent" refers to a compound useful in the treatment of a cancer, such as a CD20-positive cell proliferative disorder (e.g., a B cell proliferative disorder; e.g., a non-Hodgkin's lymphoma (NHL) (e.g., a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma), a chronic lymphoid leukemia (CLL), or a central nervous system lymphoma (CNSL)). Examples of chemotherapeutic agents include EGFR inhibitors (including small molecule inhibitors (e.g., erlotinib (TARCEVA®, Genentech/OSI Pharm.); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); and dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl)ethyl]amino]methyl]-2-furanyl]-4-quinazolinamine)); a tyrosine kinase inhibitor (e.g., an EGFR inhibitor; a small molecule HER2 tyrosine kinase inhibitor such as TAK165 (Takeda); CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; PKI-166 (Novartis); pan-HER inhibitors such as canertinib (CI-1033; Pharmacia); Raf-1 inhibitors such as antisense agent ISIS-5132 (ISIS Pharmaceuticals) which inhibit Raf-1 signaling; non-HER-targeted tyrosine kinase inhibitors such as imatinib mesylate (GLEEVEC®, Glaxo SmithKline); multi-targeted tyrosine kinase inhibitors such as sunitinib (SUTENT®, Pfizer); VEGF receptor tyrosine kinase inhibitors such as vatalanib (PTK787/ZK222584, Novartis/Schering AG); MAPK extracellular regulated kinase I inhibitor CI-1040 (Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo [2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone); and rapamycin (sirolimus, RAPAMUNE®)); proteasome inhibitors such as bortezomib (VELCADE®, Millennium Pharm.); disulfiram; epigallocatechin gallate; salinosporamide A; carfilzomib; 17-AAG (geldanamycin); radicicol; lactate dehydrogenase A (LDH-A); fulvestrant (FASLODEX®, AstraZeneca); letrozole (FEMARA®, Novartis), finasunate (VATALANIB®, Novartis); oxaliplatin (ELOXATIN®, Sanofi); 5-FU (5-fluorouracil); leucovorin; Ionafamib (SCH 66336); sorafenib (NEXAVAR®, Bayer Labs); AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylmelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin γ1 and calicheamicin ω1); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, cactinomycin, carabicin, caminomycin, carzinophilin, chromomycinis, dactinomycin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); thiotepa; chloranmbucil; GEMZAR® (gemcitabine); 6-thioguanine; mercaptopurine; methotrexate; etoposide (VP-16); ifosfamide; mitoxantrone; novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids, prodrugs, and derivatives of any of the above.

Chemotherapeutic agents also include (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, triptorelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEU- VECTIN®, and VAXID®; (ix) growth inhibitory agents including vincas (e.g., vincristine and vinblastine), NAVELBINE® (vinorelbine), taxanes (e.g., paclitaxel, nab-paclitaxel, and docetaxel), topoisomerase II inhibitors (e.g., doxorubicin, epirubicin, daunorubicin, etoposide, and bleomycin), and DNA alkylating agents (e.g., tamoxigen, dacarbazine, mechlorethamine, cisplatin, methotrexate, 5-fluorouracil, and ara-C); and (x) pharmaceutically acceptable salts, acids, prodrugs, and derivatives of any of the above.

The term "chemo-immunotherapy" refers to combination therapy that includes both chemotherapy drugs and immunotherapeutic agents. In some embodiments, chemo-immunotherapy is used to treat a cancer, e.g., a CD20-positive cancer, e.g., a NHL, e.g., e.g., a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma. In some embodiments, immunotherapeutic agents include an antibody, e.g., an anti-CD20 antibody (e.g., an anti-CD20 monoclonal antibody). In some embodiments, the anti-CD20 antibody or anti-CD20 monoclonal antibody is rituximab. In some embodiments, chemo-immunotherapy includes R-GemOx.

The term "R-GemOx" as used herein refers to a treatment comprising rituximab (RITUXAN®; CAS #: 174722-31-7) plus gemcitabine (CAS #: 95058-81-4) and oxaliplatin (CAS #: 61825-94-3). In some embodiments, R-GemOx is a chemotherapy treatment or regimen used in the treatment of a cancer, optionally a B cell proliferative disorder (e.g., a non-Hodgkin's lymphoma; e.g., a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma). In some embodiments, R-GemOx is the standard of care (SOC) or standard therapy to be administered to a subject to treat the cancer, optionally the B cell proliferative disorder (e.g., the non-Hodgkin's lymphoma; e.g., the diffuse-large B cell lymphoma (DLBCL), a follicular lymphoma (FL), the high-grade B cell lymphoma (HGBL), the mantle cell lymphoma (MCL), the high-grade B cell lymphoma, the primary mediastinal (thymic) large B cell lymphoma (PMLBCL), the diffuse B cell lymphoma, the small lymphocytic lymphoma, the marginal zone lymphoma (MZL), the Burkitt lymphoma, the a lymphoplasmacytic lymphoma). In some embodiments, R-GemOx is the standard therapy to be administered to subjects who are relapsed and/or refractory to prior therapies and/or subjects who are ineligible for autologous stem cell therapy (ASCT). In some embodiments, R-GemOx is administered every two weeks (in 14-day dosing cycles) for eight dosing cycles. In some embodiments, the dosing regimen for R-GemOx therapy comprises eight 14-day dosing cycles, wherein during each dosing cycle, the subject is administered 375 mg/m$^2$ rituximab intravenously (IV), 1000 mg/m$^2$ gemcitabine IV, and 1000 mg/m$^2$ oxaliplatin IV.

The term "cytotoxic agent" as used herein refers to any agent that is detrimental to cells (e.g., causes cell death, inhibits proliferation, or otherwise hinders a cellular function). Cytotoxic agents include, but are not limited to, radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{212}$Pb, and radioactive isotopes of Lu); chemotherapeutic agents; enzymes and fragments thereof such as nucleolytic enzymes; and toxins such as small molecule toxins or enzymatically active toxins of bacterial, fungal, plant or animal origin, including fragments and/or variants thereof. Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one instance, the cytotoxic agent is a platinum-based chemotherapeutic agent (e.g., carboplatin or cisplatin). In one instance, the cytotoxic agent is an antagonist of EGFR, e.g., N-(3-ethynylphenyl)-6,7-bis(2-methoxyethoxy)quinazolin-4-amine (e.g., erlotinib). In one instance the cytotoxic agent is a RAF inhibitor, e.g., a BRAF and/or CRAF inhibitor. In one instance the RAF inhibitor is vemurafenib. In one instance, the cytotoxic agent is a PI3K inhibitor.

The term "package insert" is used to refer to instructions customarily included in commercial packages of therapeutic products, that contain information about the indications, usage, dosage, administration, combination therapy, contraindications and/or warnings concerning the use of such therapeutic products.

III. Therapeutic Methods

Provided herein are methods of treating a subject or a population of subjects having a CD20-positive cell proliferative disorder (e.g., a B cell proliferative disorder; e.g., a non-Hodgkin's lymphoma (NHL) (e.g., a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma), a chronic lymphoid leukemia (CLL), or a central nervous system lymphoma (CNSL)), by administration of mosunetuzumab and polatuzumab vedotin as a combination therapy. In particular, provided herein are methods of treating a subject or a population of subjects having an aggressive NHL (e.g., a DLBCL, a transformed FL, or a Grade 3b FL) by subcutaneous administration of mosunetuzumab and intravenous administration of polatuzumab vedotin as a combination therapy. In some instances, the subject or the population of subjects are relapsed and/or refractory (R/R) to at least one line of prior therapy, while maintaining an acceptable safety profile (e.g., with respect to frequency and severity of adverse events, such as cytokine release syndrome (CRS)). In some instances, the subject or the population of subjects may have received two or more lines of prior therapy. In some instances, the subjects may be ineligible for autologous stem cell transplant (ASCT).

A. Therapeutic Methods for Dosing of Mosunetuzumab

In one aspect, the invention provides a method of treating a subject having a CD20-positive cell proliferative disorder comprising subcutaneously administering to the subject mosunetuzumab and intravenously administering to the subject polatuzumab vedotin in a dosing regimen comprising at least a first dosing cycle and a second dosing cycle, wherein: (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg (e.g., 5 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 5 mg), the C1D2 of mosunetuzumab is about 15 mg (e.g., 15 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 15 mg) or about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and the C1D3 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein the C2D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg).

In some embodiments, the C1D2 is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg).

In some embodiments, the C1D2 is about 15 mg (e.g., 15 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 15 mg).

In some embodiments, the first dosing cycle is a 21-day (±1 day) dosing cycle. In some embodiments, the C1D1, C1D2, and C1D3 of mosunetuzumab are administered on or about Days 1, 8 (±1 day), and 15 (±1 day), respectively, of the first dosing cycle. In some embodiments, the C1 D1 of polatuzumab vedotin is administered on Day 1 of the first dosing cycle.

In some embodiments, the second dosing cycle is a 21-day (±1 day) dosing cycle. In some embodiments, the C2D1 of mosunetuzumab is administered on Day 1 of the second dosing cycle. In some embodiments, the C2D1 of polatuzumab vedotin is administered on Day 1 of the second dosing cycle.

In some embodiments, the method further comprises one or more additional dosing cycles. In some embodiments, the method comprises four to six additional dosing cycles. In some embodiments, the method comprises six additional dosing cycles. In some embodiments, each additional dosing cycle is a 21-day (±1 day) dosing cycle.

In some embodiments, one or more of the additional dosing cycles comprise an additional single dose of mosunetuzumab and an additional single dose of polatuzumab vedotin. In some embodiments, the additional single dose of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg). In some embodiments, each additional single dose of polatuzumab vedotin is administered to the subject on Day 1 of each additional dosing cycle comprising an additional dose of polatuzumab vedotin. In some embodiments, one or more of the additional dosing cycles comprise an additional single dose of mosunetuzumab and do not comprise administration of polatuzumab vedotin.

In some embodiments, the additional single dose of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg). In some embodiments, each additional single dose of mosunetuzumab is administered to the subject on Day 1 of each additional dosing cycle comprising an additional dose of mosunetuzumab.

In some embodiments, the dosing regimen comprises six additional dosing cycles, wherein each of the six additional dosing cycles comprises a single dose of mosunetuzumab, and wherein no more than four of the six additional dosing cycles comprise administration of polatuzumab vedotin.

In one aspect, the invention features a method of treating a subject having a CD20-positive cell proliferative disorder comprising subcutaneously administering to the subject mosunetuzumab and intravenously administering to the subject polatuzumab vedotin in a dosing regimen comprising eight dosing cycles, wherein: (a) the first dosing cycle comprises: (i) a first dose (C1D1) of mosunetuzumab, a second dose (C1D2) of mosunetuzumab, and a third dose (C1D3) of mosunetuzumab, wherein the C1D1 of mosunetuzumab is about 5 mg (e.g., 5 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 5 mg), the C1D2 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and the C1D3 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg); and (ii) a single dose (C1D1) of polatuzumab vedotin, wherein the C1D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); (b) the second to sixth dosing cycles each comprises a single dose (C2D1-C6D1) of mosunetuzumab and a single dose (C2D1-C6D1) of polatuzumab vedotin, wherein each single dose C2D1-C6D1 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein each single dose C2D1C6D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); and (c) the seventh and eighth dosing cycles each comprises a single dose C7D1 and C8D1, respectively, of mosunetuzumab and does not comprise administration of polatuzumab vedotin, wherein each single dose C7D1 and C8D1 is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg).

In one aspect, the invention features a method of treating a subject having a CD20-positive cell proliferative disorder comprising subcutaneously administering to the subject mosunetuzumab and intravenously administering to the subject polatuzumab vedotin in a dosing regimen comprising eight dosing cycles, wherein: (a) the first dosing cycle comprises: (i) a first dose (C1D1) of mosunetuzumab, a second dose (C1D2) of mosunetuzumab, and a third dose (C1D3) of mosunetuzumab, wherein the C1D1 of mosunetuzumab is about 5 mg (e.g., 5 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 5 mg), the C1D2 of mosunetuzumab is about 15 mg (e.g., 15 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 15 mg), and the C1D3 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg); and (ii) a single dose (C1D1) of polatuzumab vedotin, wherein the C1D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); (b) the second to sixth dosing cycles each comprises a single dose (C2D1-C6D1) of mosunetuzumab and a single dose (C2D1-C6D1) of polatuzumab vedotin, wherein each single dose C2D1-C6D1 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein each single dose C2D1C6D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); and (c) the seventh and eighth dosing cycles each comprises a single dose C7D1 and C8D1, respectively, of mosunetuzumab and does not comprise administration of polatuzumab vedotin, wherein each single dose C7D1 and C8D1 is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg).

In some embodiments, each dosing cycle is a 21-day (±1 day) dosing cycle. In some embodiments, the C1D1, C1D2, and C1D3 of mosunetuzumab are administered on or about Days 1, 8 (±1 day), and 15 (±1 day), respectively, of the first dosing cycle. In some embodiments, each single dose of the C2D1-C8D1 of mosunetuzumab is administered on Day 1 of each respective dosing cycle.

In some embodiments, each single dose of the C1D1-C6D1 of polatuzumab vedotin is administered on Day 1 of each respective dosing cycle.

In some embodiments, the C1D1 of polatuzumab vedotin is administered prior to administration of the C1D1 of mosunetuzumab, and wherein the C2D1 of polatuzumab vedotin is administered prior to administration of the C2D1 of mosunetuzumab. In some embodiments, each single dose C3D1-C6D1 of polatuzumab vedotin is administered prior to administration of each single dose C3D1-C6D1 of mosunetuzumab, respectively. In some embodiments, when mosunetuzumab and polatuzumab vedotin are administered on the same day, mosunetuzumab may be administered before, simultaneously with, or after administration of polatuzumab vedotin. In some instances, mosunetuzumab is administered after administration of polatuzumab vedotin. In particular instances, mosunetuzumab is administered at least 60 minutes (e.g., 1 hour, 1.5 hours, 2 hours, 2.5 hours, 3 hours, 3.5 hours, 4 hours, 4.5 hours, 5 hours, 6 hours, 7 hours, 8 hours, 9 hours, 10 hours, 11 hours, or 12 hours) after administration of polatuzumab vedotin. In some embodiments, polatuzumab vedotin is administered at least about 60 minutes (e.g., 1 hour, 1.5 hours, 2 hours, 2.5 hours, 3 hours, 3.5 hours, 4 hours, 4.5 hours, 5 hours, 6 hours, 7 hours, 8 hours, 9 hours, 10 hours, 11 hours, or 12 hours) prior to administration of mosunetuzumab.

In some embodiments, the CD20-positive cell proliferative disorder is a B cell proliferative disorder. In some embodiments, the B cell proliferative disorder is a non-Hodgkin's lymphoma (NHL), a chronic lymphoid leukemia (CLL), or a central nervous system lymphoma (CNSL).

In some embodiments, the NHL is a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma. In some embodiments, the NHL is a relapsed and/or refractory (R/R) NHL.

In some embodiments, the NHL is a DLBCL. In some embodiments, the DLBCL is an R/R DLBCL. In some embodiments, the DLBCL is a Richter's transformation.

In some embodiments, the NHL is an FL (e.g., a Grade 1, 2, 3a, or 3b FL). In some embodiments, the FL is an R/R FL. In some embodiments, the FL is a transformed FL.

In some embodiments, the NHL is a HGBL. In some embodiments, the HGBL is an R/R HGBL.

In some embodiments, the NHL is an aggressive NHL. In some embodiments, the aggressive NHL is a DLBCL, a transformed FL, or a Grade 3b FL. In some embodiments, the aggressive NHL is an R/R NHL.

In some embodiments, the subject is ineligible for autologous stem cell transplant (ASCT).

In some embodiments, the subject has relapsed after or is refractory to two or more (e.g., two, three, four, five, six, seven, eight, nine, ten, or more) prior lines of therapy.

In some embodiments, the subject is human.

In one aspect, the invention features a method of treating a population of subjects having a CD20-positive cell proliferative disorder comprising subcutaneously administering to the subjects of the population mosunetuzumab and intravenously administering to the subjects of the population polatuzumab vedotin in a dosing regimen comprising at least a first dosing cycle and a second dosing cycle, wherein: (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg (e.g., 5 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 5 mg), the C1D2 of mosunetuzumab is about 15 mg (e.g., 15 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 15 mg) or about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and the C1D3 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein the C1D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); and (b) the second dosing cycle comprises a single dose (C2D1) of mosunetuzumab and a single dose (C2D1) of polatuzumab vedotin, wherein the C2D1 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein the C2D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg).

In one aspect, the invention features a method of treating a population of subjects having a CD20-positive cell proliferative disorder comprising subcutaneously administering to the subjects of the population mosunetuzumab and intravenously administering to the subjects of the population polatuzumab vedotin in a dosing regimen comprising eight dosing cycles, wherein: (a) the first dosing cycle comprises: (i) a first dose (C1D1) of mosunetuzumab, a second dose (C1D2) of mosunetuzumab, and a third dose (C1D3) of mosunetuzumab, wherein the C1 D1 of mosunetuzumab is about 5 mg (e.g., 5 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 5 mg), the C1D2 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and the C1D3 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg); and (ii) a single dose (C1D1) of polatuzumab vedotin, wherein the C1D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); (b) the second to sixth dosing cycles each comprises a single dose (C2D1-C6D1) of mosunetuzumab and a single dose (C2D1-C6D1) of polatuzumab vedotin, wherein each single dose C2D1-C6D1 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein each single dose C2D1C6D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); and (c) the seventh and eighth dosing cycles each comprises a single dose C7D1 and C8D1, respectively, of mosunetuzumab and does not comprise administration of polatuzumab vedotin, wherein each single dose C7D1 and C8D1 is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg).

In some embodiments, the average duration of progression-free survival of the population of subjects is higher than a reference average duration of progression-free survival of a reference population of subjects.

In some embodiments, the complete response rate in the population of subjects is higher than a reference complete response rate in a reference population of subjects.

In some embodiments, the objective response rate in the population of subjects is higher than a reference objective response rate in a reference population of subjects.

In some embodiments, the average duration of response of the population of subjects is higher than a reference average duration of response of a reference population of subjects.

In some embodiments, the average duration of complete response of the population of subjects is higher than a reference average duration of complete response of a reference population of subjects.

In some embodiments, the reference population of subjects is administered a combination therapy comprising rituximab, gemcitabine, and oxaliplatin. In some embodiments, the combination therapy is administered to the reference population of subjects in a dosing cycle comprising eight dosing cycles. In some embodiments, each dosing cycle is a 14-day (±1 day) dosing cycle. In some embodiments, the combination therapy is administered to the reference population of subjects about every two weeks (Q2W). In some embodiments, rituximab is administered intravenously at a dose of about 375 mg/m$^2$ (e.g., 375 mg/m$^2$±1 mg/m$^2$, ±2.5 mg/m$^2$, ±5 mg/m$^2$, ±7.5 mg/m$^2$, ±10 mg/m$^2$, ±20 mg/m$^2$, ±30 mg/m$^2$, ±40 mg/m$^2$, or ±50 mg/m$^2$; e.g., 375 mg/m$^2$) Q2W, gemcitabine is administered intravenously at a dose of about 1000 mg/m$^2$ Q2W (e.g., 1000 mg/m$^2$±1 mg/m$^2$, ±2.5 mg/m$^2$, ±5 mg/m$^2$, ±7.5 mg/m$^2$, ±10 mg/m$^2$, ±20 mg/m$^2$, ±30 mg/m$^2$, ±40 mg/m$^2$, ±50 mg/m$^2$; ±100 mg/m$^2$; ±150 mg/m$^2$; ±200 mg/m$^2$; ±250 mg/m$^2$; ±300 mg/m$^2$; e.g., 1000 mg/m$^2$), and oxaliplatin is administered intravenously at a dose of about 100 mg/m$^2$ (e.g., 100 mg/m$^2$±1 mg/m$^2$, ±2.5 mg/m$^2$, ±5 mg/m$^2$, ±7.5 mg/m$^2$, ±10 mg/m$^2$, ±20 mg/m$^2$, or ±30 mg/m$^2$; e.g., 100 mg/m$^2$) Q2W.

In some embodiments, the CD20-positive cell proliferative disorder is a B cell proliferative disorder. In some embodiments, the B cell proliferative disorder is a non-Hodgkin's lymphoma (NHL), a chronic lymphoid leukemia (CLL), or a central nervous system lymphoma (CNSL).

In some embodiments, the NHL is a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma. In some embodiments, the NHL is a relapsed and/or refractory (R/R) NHL.

In some embodiments, the NHL is a DLBCL. In some embodiments, the DLBCL is an R/R DLBCL. In some embodiments, the DLBCL is a Richter's transformation.

In some embodiments, the NHL is an FL (e.g., a Grade 1, 2, 3a, or 3b FL). In some embodiments, the FL is an R/R FL. In some embodiments, the FL is a transformed FL.

In some embodiments, the NHL is a HGBL. In some embodiments, the HGBL is an R/R HGBL.

In some embodiments, the NHL is an aggressive NHL. In some embodiments, the aggressive NHL is a DLBCL, a transformed FL, or a Grade 3b FL. In some embodiments, the aggressive NHL is an R/R NHL.

In some embodiments, each subject in the population of subjects is ineligible for autologous stem cell transplant (ASCT). In some embodiments, each subject in the population of subjects has relapsed after or is refractory to two or more prior lines of therapy. In some embodiments, each subject in the population of subjects is human.

In some embodiments, each subject in the reference population of subjects is ineligible for autologous stem cell transplant (ASCT). In some embodiments, each subject in the reference population of subjects has relapsed after or is refractory to two or more prior lines of therapy. In some embodiments, each subject in the reference population of subjects is human.

B. Dosing Strategies for Mitigating Adverse Events

The present invention relates to methods of treating a subject or a population of subjects having a CD20-positive cell proliferative disorder (e.g., a B cell proliferative disorder; e.g., a non-Hodgkin's lymphoma (NHL) (e.g., a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma), a chronic lymphoid leukemia (CLL), or a central nervous system lymphoma (CNSL)), by administration of mosunetuzumab and polatuzumab vedotin as a combination therapy. In particular, the present invention relates to methods of treating a subject or a population of subjects having an aggressive NHL (e.g., a DLBCL, a transformed FL, or a Grade 3b FL) by subcutaneous administration of mosunetuzumab and intravenous administration of polatuzumab vedotin as a combination therapy. In some instances, the subject or the population of subjects are relapsed and/or refractory (R/R) to at least one line of prior therapy, while maintaining an acceptable safety profile (e.g., with respect to frequency and severity of adverse events, such as cytokine release syndrome (CRS)). In some instances, the subject or the population of subjects may have received two or more lines of prior therapy. In some instances, the subjects may be ineligible for autologous stem cell transplant (ASCT). The therapies and dosing regimens described herein provide acceptable safety profiles in a subject or a population of subjects with R/R NHL treated with the described dosing regimens.

1. CRS Symptoms and Grading

Any of the methods described herein may involve monitoring a subject for cytokine release syndrome (CRS), e.g., a CRS event following commencement of any of the methods described above. Current clinical management focuses on treating the individual signs and symptoms, providing supportive care, and attempting to dampen the inflammatory response using a high dose of corticosteroids. However, this approach is not always successful, especially in the case of late intervention. The CRS grading criteria used by the methods described herein are published by the American Society for Transplantation and Cellular Therapy (ASTCT) to define mild, moderate, severe, or life-threatening CRS and harmonize reporting across clinical trials to allow rapid recognition and treatment of CRS (Lee et al. *Biol Blood Marrow Transplantation.* 25(4): 625-638, 2019). The ASTCT criteria is intended to be objective, easy to apply, and more accurately categorize the severity of CRS. This CRS grading system is shown below in Table 1.

TABLE 1

CRS Grading System

| CRS Parameter | Grade 1 | Grade 2 | Grade 3 | Grade 4 |
|---|---|---|---|---|
| Fever | Temperature ≥38° C. | Temperature ≥38° C. | Temperature ≥38° C. with | Temperature ≥38° C. |
| Hypotension | None | Not requiring vasopressors | Requiring a vasopressor with or without vasopressin | Requiring multiple vasopressors (excluding vasopressin) |
|  |  |  | and/or |  |
| Hypoxia | None | Requiring low-glow nasal cannula or blow-by | Requiring high-flow nasal cannula, facemask, nonrebreather mask or Venturi mask | Requiring positive pressure (e.g., CPAP, BiPAP, intubation and mechanical ventilation) |

ASTCT = American Society for Transplantation and Cellular Therapy; BiPAP = bilevel positive airway pressure; CPAP = continuous positive airway pressure; CRS = cytokine release syndrome; CTCAE = Common Terminology Criteria for Adverse Events.

Fever is defined as a temperature ≥38° C. not attributable to any other cause. In subjects who have CRS then receive antipyretic or anti-cytokine therapy such as tocilizumab or steroids, fever is no longer required to grade subsequent CRS severity. In this case, CRS grading is determined by hypotension and/or hypoxia.

CRS grade is determined by the more severe event, hypotension or hypoxia not attributable to any other cause. For example, a subject with temperature of 39.5° C., hypotension requiring 1 vasopressor, and hypoxia requiring low-flow nasal cannula is classified as Grade 3 CRS.

Low-flow nasal cannula is defined as oxygen delivered at ≤6 L/minute. Low flow also includes blow-by oxygen delivery, sometimes used in pediatrics. High-flow nasal cannula is defined as oxygen delivered at >6 L/minute.

CRS is associated with elevations in a wide array of cytokines, including marked elevations in IFN-γ, IL-6, and TNF-α levels. Emerging evidence implicates IL-6, in particular, as a central mediator in CRS. IL-6 is a proinflammatory, multi-functional cytokine produced by a variety of cell types, which has been shown to be involved in a diverse array of physiological processes, including T cell activation. Regardless of the inciting agent, CRS is associated with high IL-6 levels (Nagorsen et al. *Cytokine.* 25(1): 31-5, 2004; Lee et al. *Blood.* 124(2): 188-95, 2014); Doesegger et al. *Clin. Transl. Immunology.* 4(7): e39, 2015), and IL-6 correlates with the severity of CRS, with subjects who experience a Grade 4 or 5 CRS event having much higher IL-6 levels compared to subjects who do not experience CRS or experience milder CRS (Grades 0-3) (Chen et al. *J. Immunol. Methods.* 434:1-8, 2016).

Therefore, blocking the inflammatory action of IL-6 using an agent that inhibits IL-6-mediated signaling to manage CRS observed in subjects during the double-step fractionated, dose-escalation dosing regimen is an alternative to steroid treatment that would not be expected to negatively impact T cell function or diminish the efficacy or clinical benefit of mosunetuzumab therapy in the treatment of CD20-positive cell proliferative disorders (e.g., a B cell proliferative disorders).

If the subject has a CRS event that does not resolve or worsens within 24 hours of administering the IL-6R antagonist to treat the symptoms of the CRS event, and the method may further comprise administering to the subject one or more additional doses of the IL-6R antagonist to manage the CRS event. The subject may be administered a corticosteroid, such as methylprednisolone or dexamethasone if CRS event is not managed through administration of the IL-6R antagonist.

2. Other Adverse Events and Grading

Any of the methods described herein may involve monitoring a subject for additional non-CRS adverse events. Incidence, nature, and severity of physical findings and adverse events, with severity determined according to the National Cancer Institute Common Terminology Criteria for Adverse Events version 5 (NCI CTCAE v5.0). Other than CRS, one of the most common adverse events reported in subjects undergoing treatment with mosunetuzumab is neutropenia (e.g., febrile neutropenia).

Neutropenia is characterized by an abnormally low blood count of neutrophils, which are a type of white blood cells. Neutropenia may lead to an increased risk of infection. The generally accepted reference range for absolute neutrophil count (ANC) in adult humans is 1,500 to 8,000 cells/µL of blood. Mild neutropenia is characterized by ANC between 1,000-1,500 cells/µL (Grade 1-2); moderate neutropenia is characterized by ANC between 500 and 1,000 cells/µL (Grade 3), and severe neutropenia is characterized by ANC below 500 cells/µL (Grade 4). Febrile neutropenia (Grade 3±neutropenia) is characterized by ANC below 1,000 cells/µL in addition to either a single temperature measurement greater than 38.3° C. or sustained temperature measurements greater than 38° C. for more than one hour.

3. Dosing Regimens with Acceptable Safety Profiles

In one aspect, the invention features a method of treating a population of subjects having a CD20-positive cell proliferative disorder comprising subcutaneously administering to the subjects of the population mosunetuzumab and intravenously administering to the subjects of the population polatuzumab vedotin in a dosing regimen comprising at least a first dosing cycle and a second dosing cycle, wherein: (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg (e.g., 5 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 5 mg), the C1D2 of mosunetuzumab is about 15 mg (e.g., 15 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 15 mg) or about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and the C1D3 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein the C1D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); and (b) the second dosing cycle comprises a single dose (C2D1) of mosunetuzumab and a single dose (C2D1) of polatuzumab vedotin, wherein the C2D1 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein the C2D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg).

In one aspect, the invention features a method of treating a population of subjects having a CD20-positive cell proliferative disorder comprising subcutaneously administering to the subjects of the population mosunetuzumab and intravenously administering to the subjects of the population polatuzumab vedotin in a dosing regimen comprising eight dosing cycles, wherein: (a) the first dosing cycle comprises: (i) a first dose (C1D1) of mosunetuzumab, a second dose (C1D2) of mosunetuzumab, and a third dose (C1D3) of mosunetuzumab, wherein the C1 D1 of mosunetuzumab is about 5 mg (e.g., 5 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 5 mg), the C1D2 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and the C1D3 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg); and (ii) a single dose (C1D1) of polatuzumab vedotin, wherein the C1D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); (b) the second to sixth dosing cycles each comprises a single dose (C2D1-C6D1) of mosunetuzumab and a single dose (C2D1-C6D1) of polatuzumab vedotin, wherein each single dose C2D1-C6D1 of mosunetuzumab is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg), and wherein each single dose C2D1C6D1 of polatuzumab vedotin is about 1.8 mg/kg (e.g., 1.8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, or ±1 mg/kg; e.g., 1.8 mg/kg); and (c) the seventh and eighth dosing cycles each comprises a single dose C7D1 and C8D1, respectively, of mosunetuzumab and does not comprise administration of polatuzumab vedotin, wherein each single dose C7D1 and C8D1 is about 45 mg (e.g., 45 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 45 mg).

In one aspect, the methods of the invention features administering to the subject one or more additional therapeutic agents to reduce adverse effects of mosunetuzumab and/or polatuzumab vedotin administration. In some embodiments, premedication with corticosteroids reduces the rate of cytokine release syndrome (CRS) in subjects treated with mosunetuzumab (e.g., in subjects administered a combination of mosunetuzumab and polatuzumab vedotin).

In some embodiments, the one or more additional therapeutic agents is a corticosteroid or an IL-6R antagonist. In some embodiments, the one or more additional therapeutic agents is an IL-6R antagonist. In some embodiments, the IL-6R antagonist is tocilizumab. In some embodiments, tocilizumab is administered to the subject as a single dose of about 8 mg/kg (e.g., 8 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, ±1 mg/kg, ±1.5 mg/kg, or ±2 mg/kg; e.g., 8 mg/kg), and wherein the single dose does not exceed 800 mg. In some embodiments, tocilizumab is administered to the subject as a single dose of about 12 mg/kg (e.g., 12 mg/kg±0.01 mg/kg, ±0.025 mg/kg, ±0.05 mg/kg, ±0.075 mg/kg, ±0.1 mg/kg, ±0.2 mg/kg, ±0.3 mg/kg, ±0.4 mg/kg, ±0.5 mg/kg, ±0.75 mg/kg, ±1 mg/kg, ±1.5 mg/kg, or ±2 mg/kg; e.g., 12 mg/kg), and wherein the single dose does not exceed 800 mg. In some embodiments, tocilizumab is administered intravenously.

In some embodiments, the one or more additional therapeutic agents is a corticosteroid. In some embodiments, the corticosteroid is dexamethasone, prednisone, or methylprednisolone.

In some embodiments, the corticosteroid is dexamethasone. In some embodiments, dexamethasone is administered as a single dose of about 10 mg (e.g., 10 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 10 mg) every 6 hours. In some embodiments, dexamethasone is administered intravenously. In some embodiments, dexamethasone is administered as a single dose of about 20 mg (e.g., 20 mg±0.01 mg, ±0.025 mg, ±0.05 mg, ±0.075 mg, ±0.1 mg, ±0.2 mg, ±0.3 mg, ±0.4 mg, ±0.5 mg, ±0.75 mg, ±1 mg, ±1.5 mg, ±2 mg, or ±3 mg; e.g., 20 mg) prior to administration of any dose of mosunetuzumab. In some embodiments, dexamethasone is administered orally.

In some embodiments, the corticosteroid is methylprednisolone. In some embodiments, methylprednisolone is administered at a dose of about 1000 mg/day (e.g., 1000 mg/day±1 mg/day, ±2.5 mg/day, ±5 mg/day, ±7.5 mg/day, ±10 mg/day, ±20 mg/day, ±30 mg/day, ±40 mg/day, ±50 mg/day, ±75 mg/day, ±100 mg/day, ±150 mg/day, ±200 mg/day, or ±300 mg/day; e.g., 1000 mg/day). In some embodiments, methylprednisolone is administered intravenously.

In some embodiments, the corticosteroid is prednisone. In some embodiments, prednisone is administered at a dose of about 10-30 mg/day (e.g., about 10 mg/day, about 11 mg/day, about 12 mg/day, about 13 mg/day, about 14 mg/day, about 15 mg/day, about 16 mg/day, about 17 mg/day, about 18 mg/day, about 19 mg/day, about 20 mg/day, about 21 mg/day, about 22 mg/day, about 23 mg/day, about 24 mg/day, about 25 mg/day, about 26 mg/day, about 27 mg/day, about 28 mg/day, about 29 mg/day, or about 30 mg/day; e.g., 10 mg/day, 11 mg/day, 12 mg/day, 13 mg/day, 14 mg/day, 15 mg/day, 16 mg/day, 17 mg/day, 18 mg/day, 19 mg/day, 20 mg/day, 21 mg/day, 22 mg/day, 23 mg/day, 24 mg/day, 25 mg/day, 26 mg/day, 27 mg/day, 28 mg/day, 29 mg/day, or 30 mg/day). In some embodiments, prednisone is administered orally.

In some embodiments, the one or more additional therapeutic agents is acetaminophen or paracetamol. In some embodiments, acetaminophen or paracetamol is administered as a single dose of about 500-1000 mg (e.g., about 500 mg, about 550 mg, about 600 mg, about 650 mg, about 700 mg, about 750 mg, about 800 mg, about 850 mg, about 900 mg, about 950 mg, or about 1000 mg; e.g., 500 mg, 550 mg, 600 mg, 650 mg, 700 mg, 750 mg, 800 mg, 850 mg, 900 mg, 950 mg, or 1000 mg) prior to administration of any dose of polatuzumab vedotin. In some embodiments, acetaminophen or paracetamol is administered orally.

In some embodiments, the one or more additional therapeutic agents is diphenhydramine. In some embodiments, diphenhydramine is administered as a single dose of about 50-100 mg (e.g., about 50 mg, about 55 mg, about 60 mg, about 65 mg, about 70 mg, about 75 mg, about 80 mg, about 85 mg, about 90 mg, about 95 mg, or about 100 mg; e.g., 50 mg, 55 mg, 60 mg, 65 mg, 70 mg, 75 mg, 80 mg, 85 mg, 90 mg, 95 mg, or 100 mg) prior to administration of any dose of polatuzumab vedotin. In some embodiments, diphenhydramine is administered orally.

The methods described herein may result in an acceptable safety profile for subjects having a CD20-positive cell proliferative disorder (e.g., a B cell disorder, e.g., a non-Hodgkin's lymphoma, e.g., an aggressive NHL, e.g., a R/R aggressive NHL) being treated with combination therapy of mosunetuzumab and polatuzumab vedotin. In particular instances, the combination therapy comprising mosunetuzumab and polatuzumab vedotin comprises mosunetuzumab administered subcutaneously and polatuzumab vedotin administered intravenously.

IV. Therapeutic Agents

A. Mosunetuzumab

The invention provides mosunetuzumab, a bispecific antibody that binds to CD20 and CD3, useful for treating a CD20-positive cell proliferative disorder. In some instances, the CD20-positive cell proliferative disorder is a relapsed and/or refractory (R/R) non-Hodgkin's lymphomas (NHLs) (e.g., aggressive NHLs (aNHLs)), including, e.g., R/R diffuse large DLBCL, R/R HGBL, R/R trFL, and R/R Grade 3b FL.

In some instances, mosunetuzumab includes an anti-CD20 arm having a first binding domain comprising at least one, two, three, four, five, or six hypervariable regions (HVRs) selected from (a) an HVR-H1 comprising the amino acid sequence of GYTFTSYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of VVYYSN-SYWYFDV (SEQ ID NO: 3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6). In some instances, mosunetuzumab comprises an anti-CD20 arm comprising a first binding domain comprising at least one (e.g., 1, 2, 3, or 4) of the heavy chain framework regions FR-H1, FR-H2, FR-H3, and FR-H4 comprising the sequences of SEQ ID NOs: 17-20, respectively, and/or at least one (e.g., 1, 2, 3, or 4) of the light chain framework regions FR-L1, FR-L2, FR-L3, and FR-L4 comprising the sequences of SEQ ID NOs: 21-24, respectively. In some instances, mosunetuzumab comprises an anti-CD20 arm comprising a first binding domain comprising (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7; (b) a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8; or (c) a VH domain as in (a) and a VL domain as in (b). Accordingly, in some instances, the first binding domain comprises a VH domain comprising an amino acid sequence of SEQ ID NO: 7 and a VL domain comprising an amino acid sequence of SEQ ID NO: 8.

In some instances, mosunetuzumab includes an anti-CD3 arm having a second binding domain comprising at least one, two, three, four, five, or six HVRs selected from (a) an HVR-H1 comprising the amino acid sequence of NYYIH (SEQ ID NO: 9); (b) an HVR-H2 comprising the amino acid sequence of WIYPGDGNTKYNEKFKG (SEQ ID NO: 10); (c) an HVR-H3 comprising the amino acid sequence of DSYSNYYFDY (SEQ ID NO: 11); (d) an HVR-L1 comprising the amino acid sequence of KSSQSLLNSRTRKNYLA (SEQ ID NO: 12); (e) an HVR-L2 comprising the amino acid sequence of WASTRES (SEQ ID NO: 13); and (f) an HVR-L3 comprising the amino acid sequence of TQSFILRT (SEQ ID NO: 14). In some instances, mosunetuzumab comprises an anti-CD3 arm comprising a second binding domain comprising at least one (e.g., 1, 2, 3, or 4) of the heavy chain framework regions FR-H1, FR-H2, FR-H3, and FR-H4 comprising the sequences of SEQ ID NOs: 25-28, respectively, and/or at least one (e.g., 1, 2, 3, or 4) of the light chain framework regions FR-L1, FR-L2, FR-L3, and FR-L4 comprising the sequences of SEQ ID NOs: 29-32, respectively. In some instances, mosunetuzumab comprises an anti-CD3 arm comprising a second binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 15; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 16; or (c) a VH domain as in (a) and a VL domain as in (b). Accordingly, in some instances, the second binding domain comprises a VH domain comprising an amino acid sequence of SEQ ID NO: 15 and a VL domain comprising an amino acid sequence of SEQ ID NO: 16.

In some instances, mosunetuzumab includes (1) an anti-CD20 arm having a first binding domain comprising at least one, two, three, four, five, or six HVRs selected from (a) an HVR-H1 comprising the amino acid sequence of GYTFTSYNMH (SEQ ID NO: 1); (b) an HVR-H2 comprising the amino acid sequence of AIYPGNGDTSYNQKFKG (SEQ ID NO: 2); (c) an HVR-H3 comprising the amino acid sequence of VVYYSNSYWYFDV (SEQ ID NO: 3); (d) an HVR-L1 comprising the amino acid sequence of RASSSVSYMH (SEQ ID NO: 4); (e) an HVR-L2 comprising the amino acid sequence of APSNLAS (SEQ ID NO: 5); and (f) an HVR-L3 comprising the amino acid sequence of QQWSFNPPT (SEQ ID NO: 6); and (2) an anti-CD3 arm having a second binding domain comprising at least one, two, three, four, five, or six HVRs selected from (a) an HVR-H1 comprising the amino acid sequence of NYYIH (SEQ ID NO: 9); (b) an HVR-H2 comprising the amino acid sequence of WIYPGDGNTKYNEKFKG (SEQ ID NO: 10); (c) an HVR-H3 comprising the amino acid sequence of DSYSNYYFDY (SEQ ID NO: 11); (d) an HVR-L1 comprising the amino acid sequence of KSSQSLLNSRTRKNYLA (SEQ ID NO: 12); (e) an HVR-L2 comprising the amino acid sequence of WASTRES (SEQ ID NO: 13); and (f) an HVR-L3 comprising the amino acid sequence of TQSFILRT (SEQ ID NO: 14). In some instances, mosunetuzumab comprises (1) an anti-CD20 arm comprising a first binding domain comprising at least one (e.g., 1, 2, 3, or 4) of the heavy chain framework regions FR-H1, FR-H2, FR-H3, and FR-H4 comprising the sequences of SEQ ID NOs: 17-20, respectively, and/or at least one (e.g., 1, 2, 3, or 4) of the light chain framework regions FR-L1, FR-L2, FR-L3, and FR-L4 comprising the sequences of SEQ ID NOs: 21-24, respectively; and (2) an anti-CD3 arm comprising a second binding domain comprising at least one (e.g., 1, 2, 3, or 4) of heavy chain framework regions FR-H1, FR-H2, FR-H3, and FR-H4 comprising the sequences of SEQ ID NOs: 25-28, respectively, and/or at least one (e.g., 1, 2, 3, or 4) of the light chain framework regions FR-L1, FR-L2, FR-L3, and FR-L4 comprising the sequences of SEQ ID NOs: 29-32, respectively. In some instances, mosunetuzumab comprises (1) an anti-CD20 arm comprising a first binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 8; or (c) a VH domain as in (a) and a VL domain as in (b), and (2) an anti-CD3 arm comprising a second binding domain comprising (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 15; (b) a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 16; or (c) a VH domain as in (a) and a VL domain as in (b). In some instances, mosunetuzumab comprises (1) an anti-CD20 arm comprising a first binding domain comprising a VH domain comprising an amino acid sequence of SEQ ID NO: 7 and a VL domain comprising an amino acid sequence of SEQ ID NO: 8 and (2) an anti-CD3 arm comprising a second binding domain comprising a VH domain comprising an amino acid sequence of SEQ ID NO: 15 and a VL domain comprising an amino acid sequence of SEQ ID NO: 16.

In some instances, mosunetuzumab has the International Nonproprietary Names for Pharmaceutical Substances (INN) List 117 (WHO Drug Information, Vol. 31, No. 2, 2017, p. 303), or CAS Registry No. 1905409-39-3, and having (1) an anti-CD20 arm comprising the heavy chain and light chain sequences of SEQ ID NOs: 33 and 34, respectively; and (2) an anti-CD3 arm comprising the heavy chain and light chain sequences of SEQ ID NOs: 35 and 36, respectively. In some instances, mosunetuzumab comprises (1) an anti-CD20 arm comprising a first binding domain comprising (a) a heavy chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 33; (b) a light chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 34; or (c) a heavy chain as in (a) and a light chain as in (b), and (2) an anti-CD3 arm comprising a second binding domain comprising (a) a heavy chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 35; (b) a light chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 36; or (c) a heavy chain as in (a) and a light chain as in (b). In some instances, mosunetuzumab comprises (1) an anti-CD20 arm comprising a first binding domain comprising a heavy chain comprising an amino acid sequence of SEQ ID NO: 33 and a light chain comprising an amino acid sequence of SEQ ID NO: 34 and (2) an anti-CD3 arm comprising a second binding domain comprising a heavy chain comprising an amino acid sequence of SEQ ID NO: 35 and a light chain comprising an amino acid sequence of SEQ ID NO: 36.

Amino acid sequences of mosunetuzumab are summarized in Table 2 below.

TABLE 2

Sequence IDs for Mosunetuzumab

| CD3 Arm | | CD20 Arm | |
|---|---|---|---|
| SEQ ID NO: | Description | SEQ ID NO: | Description |
| 9 | CD3 HVR-H1 | 1 | CD20 HVR-H1 |
| 10 | CD3 HVR-H2 | 2 | CD20 HVR-H2 |
| 11 | CD3 HVR-H3 | 3 | CD20 HVR-H3 |
| 12 | CD3 HVR-L1 | 4 | CD20 HVR-L1 |
| 13 | CD3 HVR-L2 | 5 | CD20 HVR-L2 |
| 14 | CD3 HVR-L3 | 6 | CD20 HVR-L3 |
| 15 | CD3 VH | 7 | CD20 VH |
| 16 | CD3 VL | 8 | CD20 VL |
| 35 | CD3 heavy chain | 33 | CD20 heavy chain |
| 36 | CD3 light chain | 34 | CD20 light chain |

Mosunetuzumab may be produced using recombinant methods and compositions, for example, as described in U.S. Pat. No. 4,816,567.

B. Polatuzumab Vedotin

The invention provides polatuzumab vedotin, an anti-CD79b antibody drug conjugate useful for treating a CD20-positive cell proliferative disorder. In some instances, the CD20-positive cell proliferative disorder is a relapsed and/or refractory (R/R) non-Hodgkin's lymphomas (NHLs) (e.g., aggressive NHLs (aNHLs)), including, e.g., R/R diffuse large DLBCL, R/R HGBL, R/R trFL, and R/R Grade 3b FL.

In some instances, the anti-CD79b antibody of polatuzumab vedotin (i.e., polatuzumab) includes an anti-CD79b binding domain comprising at least one, two, three, four, five, or six hypervariable regions (HVRs) selected from (a) an HVR-H1 comprising the amino acid sequence of SEQ ID NO: 37; (b) an HVR-H2 comprising the amino acid sequence of SEQ ID NO: 38; (c) an HVR-H3 comprising the amino acid sequence of SEQ ID NO: 39; (d) an HVR-L1 comprising the amino acid sequence of SEQ ID NO: 40; (e) an HVR-L2 comprising the amino acid sequence of SEQ ID NO: 41; and (f) an HVR-L3 comprising the amino acid sequence of SEQ ID NO: 42. In some instances, the anti-CD79b antibody drug conjugate includes an anti-CD79b binding domain comprising all six of the following HVRs: (a) an HVR-H1 comprising the amino acid sequence of GYTFSSYWIE (SEQ ID NO: 37); (b) an HVR-H2 comprising the amino acid sequence of GEILPGGGDTNYNE-IFKG (SEQ ID NO: 38); (c) an HVR-H3 comprising the amino acid sequence of TRRVPIRLDY (SEQ ID NO: 39); (d) an HVR-L1 comprising the amino acid sequence of KASQSVDYEGDSFLN (SEQ ID NO: 40); (e) an HVR-L2 comprising the amino acid sequence of AASNLES (SEQ ID NO: 41); and (f) an HVR-L3 comprising the amino acid sequence of QQSNEDPLT (SEQ ID NO: 42).

In some instances, the anti-CD79b antibody of polatuzumab vedotin (i.e., polatuzumab) includes at least one (e.g., 1, 2, 3, or 4) of heavy chain framework regions FR-H1, FR-H2, FR-H3, and FR-H4 comprising the sequences of SEQ ID NOs: 45-48, respectively, and/or at least one (e.g., 1, 2, 3, or 4) of the light chain framework regions FR-L1, FR-L2, FR-L3, and FR-L4 comprising the sequences of SEQ ID NOs: 49-52, respectively. In some instances, the anti-CD79b antibody drug conjugate comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 43; (b) a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 44; or (c) a VH domain as in (a) and a VL domain as in (b). Accordingly, in some instances, the anti-CD79b antibody of polatuzumab vedotin (i.e., polatuzumab) comprises a VH domain comprising an amino acid sequence of SEQ ID NO: 43 and a VL domain comprising an amino acid sequence of SEQ ID NO: 44.

In some instances, the anti-CD79b antibody of polatuzumab vedotin (i.e., polatuzumab) includes (a) a heavy chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 53; (b) a light chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 54; or (c) a heavy chain as in (a) and a light chain as in (b). Accordingly, in some instances, the anti-CD79b antibody of polatuzumab vedotin (i.e., polatuzumab) comprises a heavy chain comprising an amino acid sequence of SEQ ID NO: 53 and a light chain comprising an amino acid sequence of SEQ ID NO: 54.

The sequences of the anti-CD79b antibody of polatuzumab vedotin (i.e., polatuzumab) are summarized in Table 3 below.

TABLE 3

Sequence IDs for the Anti-CD79b Antibody of Polatuzumab Vedotin

| Heavy Chain | | Light Chain | |
|---|---|---|---|
| SEQ ID NO: | Description | SEQ ID NO: | Description |
| 37 | HVR-H1 | 40 | HVR-L1 |
| 38 | HVR-H2 | 41 | HVR-L2 |
| 39 | HVR-H3 | 42 | HVR-L3 |
| 43 | VH | 44 | VL |
| 53 | Heavy Chain | 54 | Light Chain |

In some instances, the anti-CD79b antibody of polatuzumab vedotin (i.e., polatuzumab) is linked to monomethyl auristatin E (MMAE, i.e., vedotin). In some instances, polatuzumab vedotin (immunoglobulin G1-kappa auristatin E conjugate, anti-[*Homo sapiens* CD79b (immunoglobulin-associated CD79 beta)] is a humanized monoclonal antibody conjugated to auristatin E; gamma1 heavy chain (1-447) [humanized VH (*Homo sapiens* IGHV3-23*04 (76.50%)-(IGHD)-IGHJ4*01) [8.8.10] (1-117)-*Homo sapiens* IGHG1*03 (CH1 R120>K (214)(118-215), hinge (216-230), CH2 (231-340), CH3 (341-445), CHS (446-447)) (118-447)], (220-218')-disulfide with kappa light chain (1'-218') [humanized V-KAPPA (*Homo sapiens* IGKV1-39*01 (85.90%)-IGKJ1*01) [10.3.9] (1'-111')-

*Homo sapiens* IGKC*01 (112'-218')]; dimer (226-226":229-229")-bisdisulfide; conjugated, on an average of 3 to 4 cysteinyl, to monomethylauristatin E (MMAE), via a cleavable maleimidocaproyl-valyl-citrullinyl-p-aminobenzyloxy-carbonyl (mc-val-cit-PABC) type linker; also known as RG-7596, or RO5541077-000)), as defined by International Nonproprietary Names for Pharmaceutical Substances (INN) List 110 (WHO Drug Information, Vol. 27, No. 4, 2016, p. 443). Polatuzumab vedotin is also referred to as IUPHAR/BPS Number 8404, the KEGG Number D10761, or the CAS #: 1313206-42-6. Polatuzumab vedotin is also interchangeably referred to as "polatuzumab vedotin-piiq", "huMA79bv28-MC-vc-PAB-MMAE", or "DCDS4501A."

In some instances, polatuzumab vedotin comprises the formula:

symptoms associated with CRS is a corticosteroid (e.g., dexamethasone (CAS #: 50-02-2), prednisone (CAS #: 53-03-2), prednisolone (CAS #50-42-8), or methylprednisolone (CAS #: 83-43-2)) or an IL-6R antagonist (e.g., tocilizumab (CAS #: 375823-41-9), sarilumab (CAS #: 1189541-98-7), vobarilizumab (ALX-0061; CAS #: 1628814-88-9), satralizumab (SA-237; CAS #: 1535963-91-7), and variants thereof).

In some instances, the additional therapeutic agent is tocilizumab. In some instances, the additional therapeutic agent is a corticosteroid. In some instances, the corticosteroid is dexamethasone. In some instances, the corticosteroid is prednisone. In some instances, the corticosteroid is methylprednisolone.

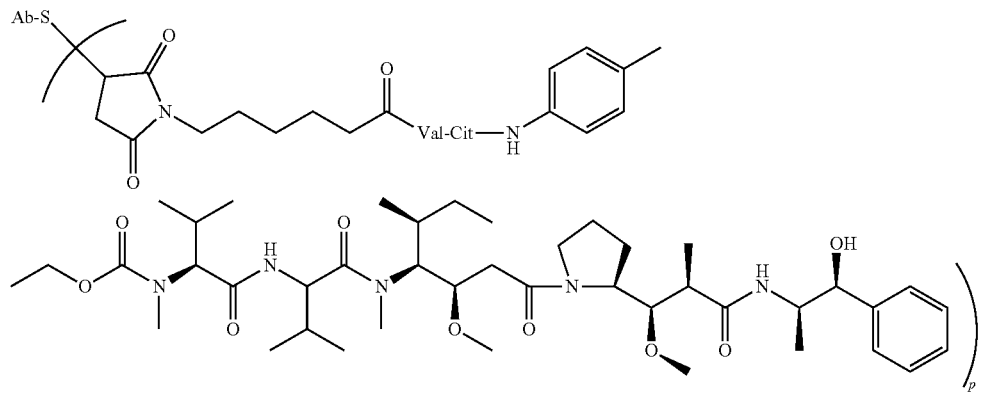

wherein Ab is polatuzumab described herein, and wherein p is between 1 and 8.

In some embodiments, polatuzumab vedotin comprises an anti-CD79b antibody (i.e., polatuzumab) that comprises a VH as in any of the embodiments provided herein, and a VL as in any of the embodiments provided herein. In some embodiments, polatuzumab vedotin comprises an anti-CD79b antibody (i.e., polatuzumab) that comprises the VH and VL sequences having the amino acid sequences of SEQ ID NO: 43 and SEQ ID NO: 44, respectively. In some embodiments, polatuzumab vedotin comprises an anti-CD79b antibody (i.e., polatuzumab) that comprises a heavy chain having the amino acid sequence of SEQ ID NO: 53 and a light chain having the amino acid sequence of SEQ ID NO: 54.

In some embodiments, polatuzumab vedotin comprises a substantially full length anti-CD79b antibody, e.g., an IgG1 antibody or other antibody class or isotype as described elsewhere herein. Polatuzumab vedotin may be produced using recombinant methods and compositions, for example, as described in U.S. Pat. No. 4,816,567. In some instances, polatuzumab vedotin is described in U.S. Pat. No. 8,088,378, which is incorporated herein by reference in its entirety.

C. Additional Therapeutic Agents

In some instances, the methods described herein include administering mosunetuzumab and polatuzumab vedotin in combination with one or more additional therapeutic agents.

In some instances, the one or more additional therapeutic agents may reduce the rate or the severity of cytokine release syndrome (CRS). In some instances, the one or more additional therapeutic agents may prevent symptoms associated with CRS. In particular instances, the additional therapeutic agent used to reduce the rate or severity of CRS or prevent In some instances, the one or more additional therapeutic agents is acetaminophen or paracetamol. Acetaminophen or paracetamol has the CAS #: 103-90-2.

In some instances, the one or more additional therapeutic agents is diphenhydramine. Diphenhydramine has the CAS #: 58-73-1.

V. Pharmaceutical Compositions and Formulations

Mosunetuzumab and/or polatuzumab vedotin described herein can be used in pharmaceutical compositions and formulations. Pharmaceutical compositions and formulations of mosunetuzumab, polatuzumab vedotin, and/or other therapeutic agents describe herein (e.g., dexamethasone, methylprednisolone, prednisone, acetaminophen, paracetamol, and diphenhydramine) can be prepared by mixing one, two, or all three agents having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Polatuzumab vedotin may also be formulated according to standard formulation and/or manufacturing practices. Dexamethasone, methylprednisolone, prednisone, acetaminophen, paracetamol, and diphenhydramine may also be formulated according to standard formulation and/or manufacturing practices. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride;

phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in U.S. Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other. For example, it may be desirable to further provide an additional therapeutic agent (e.g., a corticosteroid, a chemotherapeutic agent, a cytotoxic agent, a growth inhibitory agent, and/or an anti-hormonal agent, such as those recited herein above). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes.

In some embodiments, mosunetuzumab is formulated for administration subcutaneously. In some embodiments, polatuzumab vedotin is formulated for administration intravenously. In some embodiments, dexamethasone is formulated for administration intravenously. In some embodiments, dexamethasone is formulated for administration orally. In some embodiments, methylprednisolone is formulated for administration intravenously. In some embodiments, prednisone is formulated for administration orally. In some embodiments, acetaminophen or paracetamol is formulated for administration orally. In some embodiments, diphenhydramine is formulated for administration orally.

VI. Kits and Articles of Manufacture

In another aspect of the invention, a kit or an article of manufacture containing materials useful for the treatment, prevention, and/or diagnosis of the disorders described above is provided. The kit or article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be a vial having a stopper pierceable by a hypodermic injection needle). At least one active agent in the composition is mosunetuzumab or polatuzumab vedotin described herein. The label or package insert indicates that the composition is used for treating relapsed and/or refractory (R/R) follicular lymphoma (FL) and further includes information related to at least one of the dosing regimens described herein. In some embodiments, the label or package insert indicates that the composition is used for treating a CD20-positive cell proliferative disorder in a subject who is relapsed and/or refractory (R/R) to at least one prior lines of therapy and is autologous stem cell transplant (ASCT) or a subject who is R/R to at least two prior lines of therapy. Moreover, the kit or article of manufacture may comprise (a) a first container with a composition contained therein, wherein the composition comprises mosunetuzumab, polatuzumab vedotin, or both mosunetuzumab and polatuzumab vedotin; and (b) a second container with a composition contained therein, wherein the composition comprises an additional therapeutic agent. Examples of additional therapeutic agents include dexamethasone, methylprednisolone, prednisone, acetaminophen, paracetamol, and diphenhydramine. Alternatively, or additionally, the kit or article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

Example 1. A Randomized, Open-Label, Multicenter Phase III Study Evaluating Efficacy and Safety of Mosunetuzumab in Combination with Polatuzumab Vedotin in Comparison with Rituximab in Combination with Gemcitabine Plus Oxaliplatin (R-GemOx) in Subjects with Relapsed and/or Refractory Aggressive B-Cell Non-Hodgkin's Lymphoma Study Design This is a Phase III, open-label, multicenter, randomized, controlled trial in subjects with R/R DLBCL, trFL, or FL Grade 3b, who are not candidates for ASCT. Approximately 222 eligible subjects are randomized in 2:1 ratio to receive either mosunetuzumab (M)+polatuzumab vedotin (P) (Arm A) or R-GemOx (rituximab, gemcitabine, oxaliplatin) (Arm B). This study evaluates the efficacy and safety of mosunetuzumab compared with R-GemOx in subjects with R/R aggressive non-Hodgkin's lymphoma (aNHL), including DLBCL, trFL, and FL Grade 3b, who received at least one prior systemic therapy and are not candidates for ASCT. The study schema is provided in FIG. 1.

Randomization

Subjects in this trial are stratified at the time of randomization for the following 2 factors:
Number of previous lines of systemic therapy for aggressive lymphoma (1 vs. ≥2)
Outcome after last systemic therapy (relapsed vs. refractory)
Relapsed disease in this study is defined as disease that has recurred ≥6 months after completion of the last treatment.
Refractory disease is defined as disease that either progressed during therapy or progressed within 6 months (<6 months) of last treatment.

Arm A Treatment (Mosunetuzumab+Polatuzumab Vedotin)

The Arm A treatment consists of mosunetuzumab administered subcutaneously (SC) and polatuzumab vedotin administered intravenously (IV) (see FIG. 2A). One cycle of treatment is 21 days (e.g., 21-day dosing cycles). Mosunetuzumab is administered 5 mg SC on Cycle 1, Day 1 (Cycle 1 Dose 1; i.e., C1D1); 45 mg on Cycle 1 (Cycle 1 Dose 2; i.e., C1D2), Day 8; Cycle 1, Day 15 (Cycle 1 Dose 3; i.e., C1D3); and Day 1 of Cycles 2-8 (Cycle 2-8 Dose 1; i.e., C2D1-C8D1). Polatuzumab vedotin is administered IV at 1.8 mg/kg on Day 1 of Cycles 1-6 (C1D1-C6D1). Prophylactic (preemptive) or therapeutic use of granulocyte colony-stimulating factor (G-CSF) is permitted. Dosing occurs if a subject's clinical assessment and laboratory test values are acceptable, including peripheral neuropathy Grade≤1, ANC≥1000/mm$^3$ and platelet count ≥75,000/mm$^3$. Details of each drug administration is described in the Study Treatment section below.

Arm B Treatment (Rituximab, Gemcitabine, Oxaliplatin)

Figure 2B:
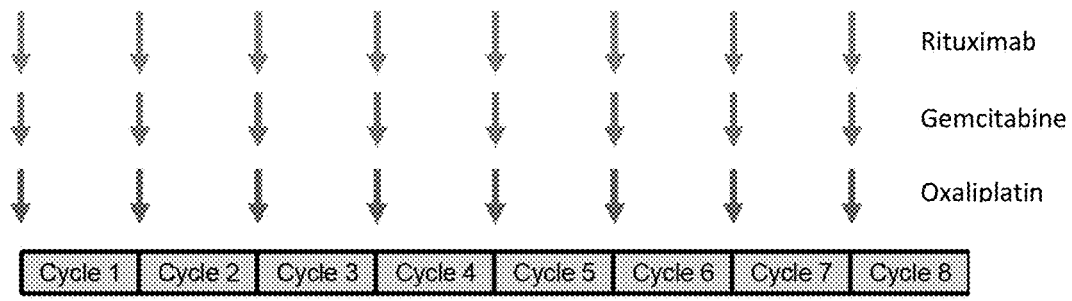
FIG. 2B is a schematic of the dosing regimen of Arm B (R-GemOx arm) described in Example 1. Treatment comprises eight total dosing cycles (Cycles 1-8). Rituximab 375 mg/m$^2$ is administered IV on Day 1 of Cycles 1-8. Gemcitabine 1000 mg/m$^2$ is administered IV on Day 1 of Cycles 1-8. Oxaliplatin 100 mg/m² is administered IV on Day 1 of Cycles 1-8. Each dosing cycle is 14 days.

The Arm B treatment consists of R-GemOx (see FIG. 2B). One cycle of treatment is 14 days (e.g., 14-day dosing cycles). Rituximab 375 mg/m$^2$ is administered IV on Day 1. Gemcitabine 1000 mg/m$^2$ is administered IV on Day 1. Oxaliplatin 100 mg/m$^2$ is administered IV on Day 1. Prophylactic (preemptive) or therapeutic use of G-CSF is permitted at the treating physician's discretion. Dosing occurs if a subject's clinical assessment and laboratory test values are acceptable, including ANC≥1000/mm$^3$ and platelet count ≥75,000/mm$^3$. If these required hematologic parameters are not met within 2 weeks after the last treatment, the treatment is delayed. If such a delay occurs despite prophylactic (preemptive) use of G CSF, it is acceptable to change the treatment cycle to every 21 days (e.g., 21-day dosing cycles), instead of 14 days for the subsequent treatment. Treatment is administered for up to 8 cycles. Details of each drug administration is described in Study Treatment section below. In some instances, a reference population of subjects comprises subjects who are assigned to Arm B and/or who receive the Arm B treatment.

Assessment During the Study

All subjects are monitored for adverse events, clinical laboratory test results and vital signs throughout the study and for at least 90 days after the final dose of study treatment. Adverse events are graded according to the National Cancer Institute Common Terminology Criteria for Adverse Events (NCI CTCAE) Version 5.0, except for cytokine release syndrome (CRS) severity, which is determined per the American Society for Transplantation and Cellular Therapy (ASTCT) CRS grading criteria CRS (Lee et al. *Biol Blood Marrow Transplantation*. 25(4): 625-638, 2019). Response assessments are performed according to the 2014 Lugano Response Criteria (Cheson B D, et al. *J Clin Oncol* 2014; 32:1-9), as assessed on positron emission tomography (PET)/computed tomography scans. To characterize the pharmacokinetic (PK) profile and immune response in response to study treatment, blood samples are taken at various timepoints before and after dosing.

Inclusion Criteria

Subjects in the study exhibit the following inclusion criteria:
Subjects who are age ≥18 years at the time of signing Informed Consent Form
Subjects who have an Eastern Cooperative Oncology Group (ECOG) Performance Status of 0, 1, or 2
Subjects who have a life expectancy of at least 12 weeks
Subjects who have CD20-positive aggressive lymphoma (e.g., aggressive non-Hodgkin's lymphoma [aNHL]) as determined by the local hematopathology laboratory from the following diagnoses by 2016 World Health Organization classification of lymphoid neoplasms:
Diffuse large B cell lymphoma (DLBCL), not otherwise specified (NOS)
High-grade B-cell lymphoma (HGBL; NOS or double/triple hit)
Transformed follicular lymphoma (trFL): The disease must be R/R to standard therapies for trFL
Follicular lymphoma (FL) Grade 3b
Subjects who have received at least one prior systemic therapy for aNHL
Subjects who have either relapsed or have become refractory to a prior regimen must meet the following criteria:
Relapsed to prior regimen(s) after having a documented history of response (CR or PR) of ≥6 months in duration from completion of regimen(s)
Refractory to any prior regimen, defined as no response to the prior therapy, or progression within 6 months of completion of the last dose of therapy.
Subjects who have received only one prior line of therapy must be ineligible for ASCT
Subjects who have measurable disease, defined as at least 1 bi-dimensionally measurable nodal lesion, defined as >1.5 cm in its longest dimension, or at least 1 bi-dimensionally measurable extra nodal lesion, defined as >1.0 cm in its longest dimension
Subjects who have a pathology report for the initial histopathology diagnosis and the most recent histopathology diagnosis prior to entering the study
Subjects with trFL must also have a pathology report completed at the time of disease transformation
Subjects whose representative tumor specimen and the corresponding pathology report are available for confirmation of diagnosis as well as for biomarker analysis
Pretreatment sample of excisional, incisional, forceps, or at least 1 core-needle tumor biopsy is required. Cytological or fine-needle aspiration samples are not acceptable.
Fresh biopsy is preferred. However, subjects who are unable to undergo biopsy procedures may be eligible for study enrollment if an archival tumor tissue sample obtained after the most recent systemic treatment as paraffin blocks or at least 10 slides (preferably 15) unstained can be sent to the Sponsor.

Receipt of tumor samples or central review of diagnosis does not have to occur prior to study enrollment Subjects who have adequate hepatic, hematologic, and renal functions defined by laboratory values below:

Hepatic function: AST and ALT≤2.5× upper limit of normal (ULN); total bilirubin ≤1.5×ULN; subjects with a documented history of Gilbert syndrome and in whom total bilirubin elevations are accompanied by elevated indirect bilirubin are eligible.

Hematologic function: platelet count ≥75,000/mm³ without transfusion within 14 days prior to first dose of study treatment; ANC≥1000/mm³; total hemoglobin ≥9 g/dL without transfusion within 14 days prior to first dose of study treatment.

Subjects with extensive marrow involvement of lymphoma and/or disease-related cytopenias (e.g., immune thrombocytopenia) may be enrolled if the following is met: platelet count ≥50,000/mm³ without transfusion within 14 days of study treatment; ANC≥500/mm³; any hemoglobin but without transfusion within 7 days prior to first dose of study treatment.

Renal function: estimated creatinine clearance (CrCl) ≥40 mL/min by Cockroft-Gault method (see Gault M H, Longerich L L, Harnett J D, et al., *Nephron* 1992, 62:249) or other institutional standard methods.

For women of childbearing potential: subjects who agree to remain abstinent (refrain from heterosexual intercourse) or use contraception and agree to refrain from donating eggs.

For men: subjects who agree to remain abstinent (refrain from heterosexual intercourse) or use a condom and agree to refrain from donating sperm.

Exclusion Criteria:

Subjects in the study do not exhibit the following exclusion criteria:

Subjects who are pregnant, breastfeeding, or intending to become pregnant during the study or within 3 months after the final dose of mosunetuzumab, 9 months after the final dose of polatuzumab vedotin, 12 months after the final dose of rituximab, 6 months after the final dose of gemcitabine, 9 months after the final dose of oxaliplatin, and 3 months after the final dose of tocilizumab, as applicable. Women of childbearing potential must have a negative serum pregnancy test result within 7 days prior to initiation of study treatment.

Subjects who have received prior treatment with mosunetuzumab or other CD20-directed bispecific antibodies, prior treatment with polatuzumab vedotin, and/or prior treatment with R-GemOx or GemOx Subjects who have a contraindication to any component of the study treatment Subjects with current Grade >1 peripheral neuropathy Subjects who have received anti-lymphoma treatments with monoclonal antibodies, radio-immunoconjugates or ADCs within 4 weeks before the first dose of study treatment Subjects who have received treatment with any chemotherapeutic agent, or treatment with any other anti-cancer agent (investigational or otherwise) within 4 weeks or 5 half-lives of the drug, whichever is shorter, prior to the first dose of study treatment Subjects who have received treatment with radiotherapy within 2 weeks prior to the first dose of study treatment Subjects who have received radiotherapy within 4 weeks prior to the first study treatment administration must have at least one measurable lesion outside of the radiation field.

Subjects who have only one measurable lesion that was previously irradiated but subsequently progressed are eligible Subjects who have ASCT within 100 days prior to the first study treatment administration Subjects who received prior treatment with CAR T therapy within 30 days before the first study treatment administration Subjects who have had prior allogeneic SCT Subjects who have had solid organ transplantation Subjects who have a known or suspected history of HLH Subjects who have a history of confirmed progressive multifocal leukoencephalopathy Subjects who have a history of severe allergic or anaphylactic reactions to monoclonal antibody therapy (or recombination antibody-related fusion proteins)

Subjects who have history of malignancy that has been treated with curative intent within ≥2 years prior to screening, with the exception of the cancer under investigation in this study and malignancies with a negligible risk of metastasis or death (e.g., 5-year OS rate >90%), such as adequately treated carcinoma in situ of the cervix, non-melanoma skin carcinoma, localized prostate cancer, ductal carcinoma in situ, or Stage I uterine cancer Subjects who have prostate cancer with no evidence of metastatic disease and are not on active therapy except for anti-androgen therapy may be allowed study entry Subjects who have a history of curatively treated basal or squamous cell carcinoma of the skin or in situ carcinoma of the cervix are allowed Subjects who have a malignancy that has been in remission without treatment for ≥2 years prior to the first study treatment administration are allowed Subjects who currently have or have had a past history of CNS involvement of lymphoma Subjects who have a history of CNS disease which was symptomatic or required treatment in the past 1 year, such as stroke, epilepsy, CNS vasculitis or neurodegenerative disease Subjects who have significant cardiovascular disease such as New York Heart Association Class III or IV cardiac disease, myocardial infarction within the last 6 months, unstable arrhythmias, or unstable angina Subjects who have significant active pulmonary disease (e.g., bronchospasm and/or obstructive pulmonary disease)

Subjects who have a known active bacterial, viral, fungal, mycobacterial, parasitic, or other infection (excluding fungal infections of the nail beds) at study enrollment, or any major episode of infection requiring treatment with IV antibiotics or hospitalization (relating to the completion of the course of antibiotics) within 2 weeks prior to the first study treatment administration Subjects who have a known or suspected chronic active Epstein-Barr virus (EBV) infection Subjects who have had a recent major surgery within 4 weeks prior to the first study treatment administration. Protocol-mandated procedures (e.g., tumor biopsies and bone marrow biopsies) are permitted.

Subjects who have positive test results for chronic hepatitis B infection (defined as positive hepatitis B surface antigen [HBsAg] serology). Subjects with occult or prior hepatitis B infection (defined as positive total hepatitis B core antibody and negative HBsAg) may be included if hepatitis B virus (HBV) DNA is undetectable at the time of screening. These subjects should be considered for prophylactic antivirals (e.g., entecavir) before and throughout the treatment, and must be willing to undergo monthly DNA testing.

Subjects who have acute or chronic hepatitis C virus (HCV) infection. Subjects who are positive for HCV antibody must be negative for HCV by polymerase chain reaction (PCR) to be eligible for study participation Subjects who have a history of HIV infection Subjects who have been administered a live, attenuated vaccine within 4 weeks before the first dose of study treatment administration or anticipation that such a live, attenuated vaccine is required during the study. Subjects must not receive live, attenuated vaccines (e.g., FluMist®) while receiving study treatment and after the last dose until B-cell recovery to the normal ranges. Killed vaccines or toxoids should be given at least 4 weeks prior to the first dose of study treatment to allow development of sufficient immunity.

Subjects with a history of autoimmune disease, including, but not limited to, myasthenia gravis, myositis, autoimmune hepatitis, systemic lupus erythematosus, rheumatoid arthritis, inflammatory bowel disease, vascular thrombosis associated with antiphospholipid syndrome, Wegener granulomatosis, Sjögren syndrome, Guillain-Barré syndrome, multiple sclerosis, vasculitis, or glomerulonephritis Subjects with a history of autoimmune-related hypothyroidism on a stable dose of thyroid replacement hormone may be eligible Subjects with controlled Type 1 diabetes mellitus who are on an insulin regimen are eligible for the study Subjects who have received systemic immunosuppressive medications (including, but not limited to, cyclophosphamide, azathioprine, methotrexate, thalidomide, and anti-TNF agents) with the exception of corticosteroid treatment ≤10 mg/day prednisone or equivalent within 2 weeks prior to first dose of study treatment Subjects who have received acute, low-dose, systemic immunosuppressant medications (e.g., single dose of dexamethasone for nausea or B-symptoms) may be enrolled in the study The use of inhaled corticosteroids is permitted The use of mineralocorticoids for management of orthostatic hypotension is permitted The use of physiologic doses of corticosteroids for management of adrenal insufficiency is permitted Subjects who received investigational therapy, whether or not intended for lymphoma treatment, within 7 days prior to initiation of study treatment Subjects who have a clinically significant history of liver disease, including viral or other hepatitis, or cirrhosis Subjects who have any serious medical condition or abnormality in clinical laboratory tests that, precludes the subject's safe participation in and in the completion of the study, or which could affect compliance with the protocol or interpretation of results Study Treatments and Concomitant Therapy The investigational medicinal products (IMPs) for this study are mosunetuzumab, polatuzumab vedotin, rituximab, gemcitabine, oxaliplatin, and tocilizumab. On days when 2 of the IMPs are given, the order of the administration in Arm A should be polatuzumab vedotin, followed by mosunetuzumab, and the interval between the end of polatuzumab vedotin infusion and the mosunetuzumab injection should be at least 60 minutes. In Arm B, gemcitabine should be administered before oxaliplatin. The administration of rituximab can be either before gemcitabine or after oxaliplatin.

Polatuzumab Vedotin

The dose of polatuzumab vedotin is 1.8 mg/kg. Polatuzumab vedotin is administered intravenously (IV) on Day 1 in Cycles 1-6 (C1D1-C6D1). If the subject's weight within 96 hours prior to Day 1 of a given treatment cycle increases or decreases >10% from the weight obtained for Cycle 1, Day 1, the most recent weight is used to calculate the dose. The weight that triggered a dose adjustment is taken as the new reference weight for future dose adjustments. All subsequent doses are modified accordingly.

After reconstitution with sterile water for injection and dilution into IV bags that contain isotonic sodium chloride solution (0.9% NaCl), polatuzumab vedotin is administered by IV infusion with use of a dedicated standard administration set with 0.2 µM or 0.22 µM in line filters at a final polatuzumab vedotin concentration determined by the subject specific dose.

The initial dose is administered over 90 (±10) minutes to subjects who are well hydrated. Premedication (e.g., 500-1000 mg of oral acetaminophen or paracetamol and 50±100 mg diphenhydramine as per institutional standard practice) may be administered to an individual subject before administration of polatuzumab vedotin. Administration of corticosteroids is permitted at the discretion of the treating physician. If infusion-related reactions (IRRs) are observed with the first infusion in the absence of premedication, premedication must be administered before subsequent doses.

The polatuzumab vedotin infusion is slowed or interrupted for subjects experiencing infusion-associated symptoms. Following the initial dose, subjects are observed for 90 minutes for fever, chills, rigors, hypotension, nausea, or other infusion-associated symptoms. If prior infusions have been well-tolerated, subsequent doses of polatuzumab vedotin are administered over 30 (±10) minutes, followed by a 30-minute observation period after the infusion. The time interval between the end of infusion of polatuzumab vedotin and the start of mosunetuzumab injection is at least 60 minutes.

Mosunetuzumab

Mosunetuzumab is administered subcutaneously (SC) with a Cycle 1 step-up-dosing regimen. The same dosing, independent of body weight, is used for mosunetuzumab. In Cycle 1, subjects receive mosunetuzumab on Day 1 (5 mg; Cycle 1 Dose 1 (C1D1)), Day 8 (45 mg; Cycle 1 Dose 2 (C1D2)), and Day 15 (45 mg; Cycle 1 Dose 3 (C1D3)). In Cycles 2-8, subjects receive mosunetuzumab on Day 1 (45 mg; Cycle 2 Dose 1 to Cycle 8 Dose 1 (C2D1-C8D1)).

Mosunetuzumab is delivered by standard medical syringe with a final volume not to exceed 2.0 mL.

Mosunetuzumab is administered to well-hydrated subjects. Corticosteroid premedication with dexamethasone 20 mg is administered prior the administration of each mosunetuzumab dose. The administration of corticosteroid premedication may be optional for Cycle 2 and beyond at the investigator's discretion. However, if the subject experiences CRS with prior administration of mosunetuzumab, premedication with steroids must be administered for subsequent doses until no additional CRS events are observed. In addition, premedication with oral acetaminophen or paracetamol (e.g., 500-1000 mg) and/or 50-100 mg diphenhydramine may be administered per standard institutional practice prior to administration of mosunetuzumab.

Mosunetuzumab is administered over 30 seconds to 2 minutes. Refer to the pharmacy manual for more details, including syringe size and preferred injection site. During Cycles 1 and 2, and also for later cycles if CRS occurred after the last mosunetuzumab, subjects are observed for at least 30 minutes after mosunetuzumab for fever, chills, rigors, hypotension, nausea, or other signs and symptoms of CRS. Vital signs are recorded pre-injection (within 30 minutes) and then 30 (±15) minutes after mosunetuzumab administration. In Cycle 3 and beyond, in the absence of CRS after the last dose of mosunetuzumab, the observation time after the mosunetuzumab injection is at least 15 minutes. Vital signs are assessed prior to the mosunetuzumab injection (within 30 minutes prior to injection) and then at least once after the injection during the observation period.

Tocilizumab

Tocilizumab is administered intravenously (IV) only to those subjects who experience a CRS event for which tocilizumab is indicated. Subjects who weigh ≥30 kg receive tocilizumab 8 mg/kg in a 100-mL infusion bag or bottle, and subjects who weigh >30 kg receive tocilizumab 12 mg/kg in 50-mL infusion bag or bottle. Doses exceeding 800 mg per infusion are not recommended. The infusion is administered IV over 60 minutes. Treatment is repeated every 8 hours as necessary (for a maximum of 4 doses).

Rituximab

Rituximab is administered at a dose of 375 mg/m$^2$ by intravenously (IV) infusion on Day 1 of each 14-day cycle (Cycles 1-8). Once the rituximab infusion is complete, subjects are to be observed for 30 minutes before the start of the other infusions. The infusion of rituximab may be split over 2 days if the subject is at increased risk for an infusion-related reaction (IRR) (high tumor burden or high peripheral lymphocyte count). For subjects who experience an adverse event during a rituximab infusion, administration of R-GemOx may be continued on the following day, if required. Rituximab can be given either before gemcitabine or after oxaliplatin on the same day.

Gemcitabine

Gemcitabine is administered at 1000 mg/m$^2$ intravenously (IV) on Day 1 of each 14-day cycle (Cycles 1-8). Gemcitabine is administered before oxaliplatin on the same day.

Oxaliplatin

Oxaliplatin is administered at 100 mg/m$^2$ intravenously (IV) on Day 1 of each 14-day cycle (Cycles 1-8). Oxaliplatin is administered after gemcitabine on the same day.

Permitted Concomitant Therapy

In general, investigators may manage a subject's care (including preexisting conditions) through use of supportive therapies. Subjects who experience infusion-associated symptoms may be treated symptomatically with acetaminophen, ibuprofen, diphenhydramine, and/or H$_2$-receptor antagonists (e.g., famotidine, cimetidine), or equivalent medications. Prophylactic use of hematopoietic growth factors or anti-infectives for viral, fungal, bacterial, or *Pneumocystis* infections are permitted. Premedication with antihistamines, antipyretics, and/or analgesics are also permitted.

Cautionary Concomitant Therapy

Given the expected pharmacology of mosunetuzumab, the transient release of cytokines (most resolved within the first 24 hours of the Cycle 1, Day 1 dose) may suppress CYP450 enzymes and cause drug-drug interactions. Subjects who may be of highest risk of a drug-drug interaction are those receiving concomitant medications that are CYP450 substrates and have a narrow therapeutic index.

In vitro data suggest that unconjugated MMAE is mainly metabolized by CYP3A4 and, to a lesser extent, by CYP2D6. Based on a validated physiological-based PK model simulation (Chen et al. 2015), strong CYP3A4 inhibitors may increase the exposure (e.g., AUC) of unconjugated MMAE by approximately 50%, while antibody-conjugated monomethyl auristatin E (acMMAE; e.g., polatuzumab vedotin) PK is not affected. Concomitant medications that are strong CYP3A4 inhibitors should be considered cautionary as they may potentially lead to adverse reactions.

Cytochrome P450 enzymes in the liver are down-regulated by infection and inflammatory stimuli, including cytokines such as IL-6. Inhibition of IL-6 signaling in subjects with rheumatoid arthritis who are treated with tocilizumab may restore CYP450 activities to higher levels than those subjects not treated with tocilizumab, leading to increased metabolism of drugs that are CYP450 substrates. In vitro studies showed that tocilizumab has the potential to affect expression of multiple CYP enzymes, including CYP1A2, CY2B6, CYP2C9, CYP2C19, CYP2D6, and CYP3A4. The effects of tocilizumab on CYP2C8 or transporters are unknown. In vivo studies with omeprazole (metabolized by CYP2C19 and CYP3A4) and simvastatin (metabolized by CYP3A4) showed up to a 28% and 57% decrease in exposure 1 week following a single dose of tocilizumab, respectively. The effect of tocilizumab on CYP450 enzyme activity may persist for several weeks after stopping therapy.

Prohibited Concomitant Therapy

Herbal therapies intended for the treatment of lymphoma are prohibited.

Concomitant therapy intended for the treatment of cancer (including, but not limited to, chemotherapy, hormonal therapy, immunotherapy, radiotherapy, and herbal therapy), whether health authority-approved or experimental, is prohibited for various time periods prior to starting study treatment, depending on the agent, and during study treatment, until disease progression is documented and the subject has discontinued study treatment Intrathecal chemotherapy for CNS prophylaxis is permitted. Adjuvant endocrine therapy for non-metastatic, hormone receptor positive breast cancer and anti-androgen therapy for non-metastatic prostate cancer are permitted.

Investigational therapy, whether intended for the treatment of lymphoma or not, is prohibited within 7 days prior to initiation of study treatment and during study treatment Systemic immunosuppressive therapy is prohibited (except medications indicated per protocol, including corticosteroids and tocilizumab)

Live virus vaccines are prohibited for at least 4 weeks before initiation of or at any time during study treatment Efficacy Assessments Subjects undergo tumor assessments at screening, every 8 weeks for the first 6 months following treatment initiation, and every 3 months, regardless of dose delays, until radiographic disease progression, study discontinuation or up to 2 years, whichever is earlier, per Lugano Criteria 2014 (Cheson B D, et al. *J Clin Oncol* 2014; 32:1-9). All measurable and/or evaluable lesions are assessed and documented at screening.

Radiographic Assessments

Fluorodeoxyglucose (FDG) PET-CT scans, in conjunction with diagnostic-quality CT scans, are required at screening, the interim response assessment, and at the end-of-treatment. After the end-of-treatment, CT scans (preferred) or FDG PET-CT scans are performed. Diagnosis of disease progression based on clinical examination are confirmed radiographically by imaging (e.g., CT scan, FDG PET-CT scan) or histopathologically by biopsy as soon as feasible (within 30 days) and prior to initiation of non-protocol specified anti-cancer therapy.

All measurable and/or evaluable disease are documented at screening and re assessed at each subsequent tumor evaluation. Response is assessed by the investigator and the IRF on the basis of physical examinations, CT scans, FDG PET-CT scans.

Bone Marrow Assessment

Subjects may use screening PET/CT scans to assess bone marrow involvement; bone marrow examinations are not required unless clinically indicated (Cheson B D, et al. *J Clin Oncol* 2014; 32:1-9).

Response Evaluation

Objective response is determined at specified timepoints according to the Lugano Response Criteria (Cheson B D, et al. *J Clin Oncol* 2014; 32:1-9).

Endpoints (e.g., ORR, CRR, PFS, DOR, duration of complete response [DOCR]), are calculated programmatically.

Safety Assessment

Adverse Events

An adverse event is any untoward medical occurrence in a patient or clinical study subject temporally associated with the use of a study treatment, whether or not considered related to the study treatment.

The following events meet the definition of adverse event:
  Any abnormal laboratory test results (hematology, clinical chemistry, or urinalysis) or other safety assessments (e.g., ECG, radiological scans, vital sign measurements), including those that worsen from baseline, or are considered clinically significant in the medical and scientific judgment of the investigator (i.e., not related to progression of underlying disease)
  Exacerbation of a chronic or intermittent preexisting condition, including either an increase in frequency and/or intensity of the condition
  New condition detected or diagnosed after study treatment administration, even though it may have been present before the start of the study
  Signs, symptoms, or clinical sequelae of a suspected drug-drug interaction
  Signs, symptoms, or clinical sequelae of a suspected overdose of either study treatment or a concomitant medication Overdose per se is not reported as an adverse event or serious adverse event unless it is an intentional overdose taken with possible suicidal or self-harming intent. Such overdoses are reported regardless of sequelae.

"Lack of efficacy" or "failure of expected pharmacological action" per se is not reported as an adverse event or serious adverse event. Such instances are captured in the efficacy assessments. However, the signs, symptoms, and/or clinical sequelae resulting from lack of efficacy are reported as an adverse event or serious adverse event if they fulfill the definition of an adverse event or serious adverse event.

The investigator assesses the severity of each adverse event reported during the study through use of the NCI CTCAE (v5.0) grading scale.

Serious Adverse Events

A serious adverse event is defined as any untoward medical occurrence that, at any dose: results in death; is life-threatening; requires in-patient hospitalization or prolongation of existing hospitalization; results in persistent disability or incapacity; is a congenital anomaly or birth defect; and other adverse events deemed to be serious adverse events, e.g., invasive or malignant cancers, intensive treatment in an emergency room or at home for allergic bronchospasm, blood dyscrasias or convulsions that do not result in hospitalization, or development of drug dependency or drug abuse.

The terms "severe" and "serious" are not synonymous. Severity refers to the intensity of an adverse event (e.g., rated as mild, moderate, or severe, or according to National Cancer Institute Common Terminology Criteria for Adverse Events [NCI CTCAE] (v5.0)); the event itself may be of relatively minor medical significance (such as severe headache without any further findings). Severity and seriousness need to be independently assessed for each adverse event.

Adverse Events of Special Interest

Adverse events of special interest (AESI) for this study include cases of potential drug-induced liver injury that include an elevated ALT or AST in combination with either an elevated bilirubin or clinical jaundice and cases of suspected transmission of an infectious agent by a study treatment. In addition, AESI specific to mosunetuzumab or polatuzumab vedotin are as follows:

Mosunetuzumab:
  Grade≥2 CRS
  Grade≥2 neurologic adverse event
  Grade≥2 injection-site reaction
  Any suspected HLH or macrophage activation syndrome
  Grade≥3 TLS
  Grade≥3 febrile neutropenia
  Grade≥2 AST, ALT, or total bilirubin elevation
  Any Grade disseminated intravascular coagulation (minimum Grade 2 by definition)
  Grade≥2 tumor flare (e.g., manifestation of signs/symptoms associated with an increase in size of known nodal or extranodal lesions by clinical or radiographic assessment, new onset or worsening of preexisting pleural effusions)
  Any Grade pneumonitis/interstitial lung disease (excluding pneumonia of infectious etiology)

Polatuzumab Vedotin:
  TLS any grade (minimum Grade 3 by definition)
  Second malignancies Pharmacokinetics Serum/plasma samples are collected for measurement of serum/plasma concentrations of mosunetuzumab and polatuzumab vedotin. Samples are used to evaluate the pharmacokinetics of mosunetuzumab and polatuzumab vedotin. Samples collected for analyses of mosunetuzumab and polatuzumab vedotin concentration may also be used to evaluate safety or efficacy aspects related to concerns arising during or after the study. Also, these data are used to understand the relationship of PK exposure to dose and support characterization of dose/exposure-response relationships in the combination setting. In addition, these data are used to explore and characterize the potential PK interactions between mosunetuzumab and polatuzumab vedotin.

Clinical Outcome Assessments

Subject-reported outcome (PRO) instruments are completed to assess the treatment benefit of mosunetuzumab and polatuzumab vedotin compared with R-GemOx. In addition, PRO instruments enable the capture of each subject's direct experience with mosunetuzumab and polatuzumab vedotin.

Subject-reported outcomes data are collected through use of the following instruments: the European Organization for Research and Treatment of Cancer Quality of Life-Core 30 Questionnaire (EORTC QLQ-C30; see Aaronson et al. *J. Nat Cancer Inst.* 1993, 85(5): 365-376; Fitzsimmons et al., *Eur. J. Cancer.* 1999, 35(6): 939-941; Functional Assessment of Cancer Therapy-Lymphoma subscale (FACT Lym LymS; see Hlubocky et al., *Leuk Lymphoma.* 2013, 54(9): 1942-1946); Functional Assessment of Cancer Therapy-Gynecologic Oncology Group-Neurotoxicity (FACT/GOG-Ntx; Huang et al., *Int. J. Gynecol. Cancer.* 2007, 17(2): 387-393); and EuroQoI 5-Dimension, 5-Level Questionnaire (EQ-5D-5L; see EuroQoI Group *Health Policy.* 1990, 16(3): 199-208; Brooks *Health Policy* 1996, 37(1): 53-72; Herdman et al. *Qual. Life. Res.* 2011, 20(10): 1727-1736; Janssen et al. *Qual. Life. Res.* 2013, 22(7): 1717-1727).

Additional Samples

Additional samples may be obtained from consenting subjects. Additional sample types include tissue samples (e.g., body fluids, solid tissues, and derivatives thereof), blood samples, tumor biopsies. Samples may be used for exploratory biomarker research. Samples may be used for biomolecule extraction (e.g., DNA, RNA, and/or protein extraction).

EMBODIMENTS

Some embodiments of the technology described herein can be defined according to any of the following numbered embodiments:

1. A method of treating a subject having a CD20-positive cell proliferative disorder comprising subcutaneously administering to the subject mosunetuzumab and intravenously administering to the subject polatuzumab vedotin in a dosing regimen comprising at least a first dosing cycle and a second dosing cycle, wherein:
    (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
    (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

2. Mosunetuzumab and polatuzumab vedotin for use in treating a subject having a CD20-positive cell proliferative disorder, wherein mosunetuzumab is to be administered subcutaneously to the subject and polatuzumab vedotin is to be administered intravenously to the subject in a dosing regimen comprising at least a first dosing cycle and a second dosing cycle, and wherein:
    (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
    (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

3. Use of mosunetuzumab and polatuzumab vedotin for treating a subject having a CD20-positive cell proliferative disorder, wherein mosunetuzumab is to be administered subcutaneously to the subject and polatuzumab vedotin is to be administered intravenously to the subject in a dosing regimen comprising at least a first dosing cycle and a second dosing cycle, and wherein:
    (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
    (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

4. Use of mosunetuzumab in the manufacture of a medicament for use in combination with polatuzumab vedotin for treating a subject having a CD20-positive cell proliferative disorder, wherein mosunetuzumab is to be administered subcutaneously to the subject and polatuzumab vedotin is to be administered intravenously to the subject in a dosing regimen comprising at least a first dosing cycle and a second dosing cycle, and wherein:
    (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
    (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

5. Use of polatuzumab vedotin in the manufacture of a medicament for use in combination with mosunetuzumab for treating a subject having a CD20-positive cell proliferative disorder, wherein mosunetuzumab is to be administered subcutaneously to the subject and polatuzumab vedotin is to be administered intravenously to the subject in a dosing regimen comprising at least a first dosing cycle and a second dosing cycle, and wherein:
    (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
    (b) the second dosing cycle comprises a single dose (C2D1) of mosunetuzumab and a single dose (C2D1)

of polatuzumab vedotin, wherein the C2D1 of mosunetuzumab is about 45 mg, and wherein the C2D1 of polatuzumab vedotin is about 1.8 mg/kg.

6. Use of mosunetuzumab and polatuzumab vedotin in the manufacture of a medicament for treating a subject having a CD20-positive cell proliferative disorder, wherein mosunetuzumab is to be administered subcutaneously to the subject and polatuzumab vedotin is to be administered intravenously to the subject in a dosing regimen comprising at least a first dosing cycle and a second dosing cycle, and wherein:
  (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
  (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

7. The method, mosunetuzumab and polatuzumab vedotin for use, or use of any one of embodiments 1-6, wherein the C1D2 is about 45 mg.

8. The method, mosunetuzumab and polatuzumab vedotin for use, or use of any one of embodiments 1-6, wherein the C1D2 is about 15 mg.

9. The method, mosunetuzumab and polatuzumab vedotin for use, or use of any one of embodiments 1-8, wherein the first dosing cycle is a 21-day dosing cycle.

10. The method, mosunetuzumab and polatuzumab vedotin for use, or use of embodiment 9, wherein the C1D1, C1D2, and C1D3 of mosunetuzumab are administered or are to be administered on or about Days 1, 8, and 15, respectively, of the first dosing cycle.

11. The method, mosunetuzumab and polatuzumab vedotin for use, or use of embodiment 9 or 10, wherein the C1D1 of polatuzumab vedotin is administered or is to be administered on Day 1 of the first dosing cycle.

12. The method, mosunetuzumab and polatuzumab vedotin for use, or use of any one of embodiments 1-11, wherein the second dosing cycle is a 21-day dosing cycle.

13. The method, mosunetuzumab and polatuzumab vedotin for use, or use of embodiment 12, wherein the C2D1 of mosunetuzumab is administered or is to be administered on Day 1 of the second dosing cycle.

14. The method, mosunetuzumab and polatuzumab vedotin for use, or use of embodiment 12 or 13, wherein the C2D1 of polatuzumab vedotin is administered or is to be administered on Day 1 of the second dosing cycle.

15. The method, mosunetuzumab and polatuzumab vedotin for use, or use of any one of embodiments 1-14, wherein the method further comprises one or more additional dosing cycles.

16. The method, mosunetuzumab and polatuzumab vedotin for use, or use of embodiment 15, wherein the method comprises four to six additional dosing cycles.

17. The method, mosunetuzumab and polatuzumab vedotin for use, or use of embodiment 16, wherein the method comprises six additional dosing cycles.

18. The method, mosunetuzumab and polatuzumab vedotin for use, or use of embodiment 16 or 17, wherein each additional dosing cycle is a 21-day dosing cycle.

19. The method, mosunetuzumab and polatuzumab vedotin for use, or use of any one of embodiments 16-18, wherein one or more of the additional dosing cycles comprise an additional single dose of mosunetuzumab and an additional single dose of polatuzumab vedotin.

20. The method, mosunetuzumab and polatuzumab vedotin for use, or use of embodiment 19, wherein the additional single dose of polatuzumab vedotin is about 1.8 mg/kg.

21. The method, mosunetuzumab and polatuzumab vedotin for use, or use of embodiment 19 or 20, wherein each additional single dose of polatuzumab vedotin is administered or is to be administered to the subject on Day 1 of each additional dosing cycle comprising an additional dose of polatuzumab vedotin.

22. The method, mosunetuzumab and polatuzumab vedotin for use, or use of any one of embodiments 16-21, wherein one or more of the additional dosing cycles comprise an additional single dose of mosunetuzumab and do not comprise administration of polatuzumab vedotin.

23. The method, mosunetuzumab and polatuzumab vedotin for use, or use of any one of embodiments 19-22, wherein the additional single dose of mosunetuzumab is about 45 mg.

24. The method, mosunetuzumab and polatuzumab vedotin for use, or use of any one of embodiments 19-23, wherein each additional single dose of mosunetuzumab is administered or is to be administered to the subject on Day 1 of each additional dosing cycle comprising an additional dose of mosunetuzumab.

25. The method, mosunetuzumab and polatuzumab vedotin for use, or use of any one of embodiments 15-24, wherein the dosing regimen comprises six additional dosing cycles, wherein each of the six additional dosing cycles comprises a single dose of mosunetuzumab, and wherein no more than four of the six additional dosing cycles comprise administration of polatuzumab vedotin.

26. A method of treating a subject having a CD20-positive cell proliferative disorder comprising subcutaneously administering to the subject mosunetuzumab and intravenously administering to the subject polatuzumab vedotin in a dosing regimen comprising eight dosing cycles, wherein:
  (a) the first dosing cycle comprises:
    (i) a first dose (C1D1) of mosunetuzumab, a second dose (C1D2) of mosunetuzumab, and a third dose (C1D3) of mosunetuzumab, wherein the C1 D1 of mosunetuzumab is about 5 mg, the C1D2 of mosunetuzumab is about 45 mg, and the C1 D3 of mosunetuzumab is about 45 mg; and
    (ii) a single dose (C1D1) of polatuzumab vedotin, wherein the C1D1 of polatuzumab vedotin is about 1.8 mg/kg;
  (b) the second to sixth dosing cycles each comprises a single dose (C2D1-C6D1) of mosunetuzumab and a single dose (C2D1-C6D1) of polatuzumab vedotin, wherein each single dose C2D1-C6D1 of mosunetuzumab is about 45 mg, and wherein each single dose C2D1-C6D1 of polatuzumab vedotin is about 1.8 mg/kg; and
  (c) the seventh and eighth dosing cycles each comprises a single dose C7D1 and C8D1, respectively, of mosunetuzumab and does not comprise administration of polatuzumab vedotin, wherein each single dose C7D1 and C8D1 is about 45 mg.

27. Mosunetuzumab and polatuzumab vedotin for use in treating a subject having a CD20-positive cell proliferative disorder, wherein mosunetuzumab is to be administered subcutaneously to the subject and polatuzumab vedotin is to be administered intravenously to the subject in a dosing regimen comprising eight dosing cycles, and wherein:
  (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
  (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

28. Use of mosunetuzumab and polatuzumab vedotin for treating a subject having a CD20-positive cell proliferative disorder, wherein mosunetuzumab is to be administered subcutaneously to the subject and polatuzumab vedotin is to be administered intravenously to the subject in a dosing regimen comprising eight dosing cycles, and wherein:
  (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
  (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

29. Use of mosunetuzumab in the manufacture of a medicament for use in combination with polatuzumab vedotin for treating a subject having a CD20-positive cell proliferative disorder, wherein mosunetuzumab is to be administered subcutaneously to the subject and polatuzumab vedotin is to be administered intravenously to the subject in a dosing regimen comprising eight dosing cycles, and wherein:
  (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
  (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

30. Use of polatuzumab vedotin in the manufacture of a medicament for use in combination with mosunetuzumab for treating a subject having a CD20-positive cell proliferative disorder, wherein mosunetuzumab is to be administered subcutaneously to the subject and polatuzumab vedotin is to be administered intravenously to the in a dosing regimen comprising eight dosing cycles, and wherein:
  (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
  (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

31. Use of mosunetuzumab and polatuzumab vedotin in the manufacture of a medicament for treating a subject having a CD20-positive cell proliferative disorder, wherein mosunetuzumab is to be administered subcutaneously to the subject and polatuzumab vedotin is to be administered intravenously to the subject in a dosing regimen comprising eight dosing cycles, and wherein:
  (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
  (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

32. A method of treating a subject having a CD20-positive cell proliferative disorder comprising subcutaneously administering to the subject mosunetuzumab and intravenously administering to the subject polatuzumab vedotin in a dosing regimen comprising eight dosing cycles, wherein:
  (a) the first dosing cycle comprises:
    (i) a first dose (C1D1) of mosunetuzumab, a second dose (C1D2) of mosunetuzumab, and a third dose (C1D3) of mosunetuzumab, wherein the C1 D1 of mosunetuzumab is about 5 mg, the C1D2 of mosunetuzumab is about 15 mg, and the C1 D3 of mosunetuzumab is about 45 mg; and
    (ii) a single dose (C1D1) of polatuzumab vedotin, wherein the C1D1 of polatuzumab vedotin is about 1.8 mg/kg;
  (b) the second to sixth dosing cycles each comprises a single dose (C2D1-C6D1) of mosunetuzumab and a single dose (C2D1-C6D1) of polatuzumab vedotin, wherein each single dose C2D1-C6D1 of mosunetuzumab is about 45 mg, and wherein each single dose C2D1-C6D1 of polatuzumab vedotin is about 1.8 mg/kg; and
  (c) the seventh and eighth dosing cycles each comprises a single dose C7D1 and C8D1, respectively, of mosunetuzumab and does not comprise administration of polatuzumab vedotin, wherein each single dose C7D1 and C8D1 is about 45 mg.

33. Mosunetuzumab and polatuzumab vedotin for use in treating a subject having a CD20-positive cell proliferative disorder, wherein mosunetuzumab is to be administered subcutaneously to the subject and polatuzumab vedotin is to be administered intravenously to the subject in a dosing regimen comprising eight dosing cycles, and wherein:

(a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

34. Use of mosunetuzumab and polatuzumab vedotin for treating a subject having a CD20-positive cell proliferative disorder, wherein mosunetuzumab is to be administered subcutaneously to the subject and polatuzumab vedotin is to be administered intravenously to the subject in a dosing regimen comprising eight dosing cycles, and wherein:

(a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

35. Use of mosunetuzumab in the manufacture of a medicament for use in combination with polatuzumab vedotin for treating a subject having a CD20-positive cell proliferative disorder, wherein mosunetuzumab is to be administered subcutaneously to the subject and polatuzumab vedotin is to be administered intravenously to the subject in a dosing regimen comprising eight dosing cycles, and wherein:

(a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

36. Use of polatuzumab vedotin in the manufacture of a medicament for use in combination with mosunetuzumab for treating a subject having a CD20-positive cell proliferative disorder, wherein mosunetuzumab is to be administered subcutaneously to the subject and polatuzumab vedotin is to be administered intravenously to the subject in a dosing regimen comprising eight dosing cycles, and wherein:

(a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

37. Use of mosunetuzumab and polatuzumab vedotin in the manufacture of a medicament for treating a subject having a CD20-positive cell proliferative disorder, wherein mosunetuzumab is to be administered subcutaneously to the subject and polatuzumab vedotin is to be administered intravenously to the subject in a dosing regimen comprising eight dosing cycles, and wherein:

(a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

38. The method, mosunetuzumab and polatuzumab vedotin for use, or use of any one of embodiments 26-37, wherein each dosing cycle is a 21-day dosing cycle.

39. The method, mosunetuzumab and polatuzumab vedotin for use, or use of embodiment 38, wherein the C1D1, C1D2, and C1D3 of mosunetuzumab are administered on or about Days 1, 8, and 15, respectively, of the first dosing cycle.

40. The method, mosunetuzumab and polatuzumab vedotin for use, or use of any one of embodiments 26-39, wherein each single dose of the C2D1-C8D1 of mosunetuzumab is administered on Day 1 of each respective dosing cycle.

41. The method, mosunetuzumab and polatuzumab vedotin for use, or use of any one of embodiments 26-40, wherein each single dose of the C1D1-C6D1 of polatuzumab vedotin is administered on Day 1 of each respective dosing cycle.

42. The method, mosunetuzumab and polatuzumab vedotin for use, or use of any one of embodiments 1-41, wherein the C1D1 of polatuzumab vedotin is administered or is to be administered prior to administration of the C1D1 of mosunetuzumab, and wherein the C2D1 of polatuzumab vedotin is administered or is to be administered prior to administration of the C2D1 of mosunetuzumab.

43. The method, mosunetuzumab and polatuzumab vedotin for use, or use of any one of embodiments 26-42, wherein each single dose C3D1-C6D1 of polatuzumab vedotin is administered or is to be administered prior to administration of each single dose C3D1-C6D1 of mosunetuzumab, respectively.

44. The method, mosunetuzumab and polatuzumab vedotin for use, or use of embodiment 42 or 43, wherein polatuzumab vedotin is administered or is to be administered at least about 60 minutes prior to administration of mosunetuzumab.

45. The method of any one of embodiments 1, 7-26, 32, and 38-44, wherein the method further comprises administering to the subject one or more additional therapeutic agents.

46. The mosunetuzumab and polatuzumab vedotin for use or use of any one of embodiments 2-25, 27-31, and 33-44, wherein mosunetuzumab and polatuzumab vedotin are for use in combination with one or more additional therapeutic agents.

47. The method, mosunetuzumab and polatuzumab vedotin for use, or use of embodiment 45 or 46, wherein the one or more additional therapeutic agents is a corticosteroid or an IL-6R antagonist.

48. The method, mosunetuzumab and polatuzumab vedotin for use, or use of embodiment 47, wherein the IL-6R antagonist is tocilizumab.

49. The method, mosunetuzumab and polatuzumab vedotin for use, or use of embodiment 48, wherein tocilizumab is administered or is to be administered to the subject as a single dose of about 8 mg/kg, and wherein the single dose does not exceed 800 mg.

50. The method, mosunetuzumab and polatuzumab vedotin for use, or use of embodiment 48, wherein tocilizumab is administered or is to be administered to the subject as a single dose of about 12 mg/kg, and wherein the single dose does not exceed 800 mg.

51. The method, mosunetuzumab and polatuzumab vedotin for use, or use of any one of embodiments 48-50, wherein tocilizumab is administered or is to be administered intravenously.

52. The method, mosunetuzumab and polatuzumab vedotin for use, or use of embodiment 47, wherein the one or more additional therapeutic agents is a corticosteroid.

53. The method, mosunetuzumab and polatuzumab vedotin for use, or use of embodiment 52, wherein the corticosteroid is dexamethasone, prednisone, or methylprednisolone.

54. The method, mosunetuzumab and polatuzumab vedotin for use, or use of embodiment 53, wherein the corticosteroid is dexamethasone.

55. The method, mosunetuzumab and polatuzumab vedotin for use, or use of embodiment 54, wherein dexamethasone is administered or is to be administered as a single dose of about 10 mg every 6 hours.

56. The method, mosunetuzumab and polatuzumab vedotin for use, or use of embodiment 54 or 55, wherein dexamethasone is administered or is to be administered intravenously.

57. The method, mosunetuzumab and polatuzumab vedotin for use, or use of embodiment 54, wherein dexamethasone is administered or is to be administered as a single dose of about 20 mg prior to administration of any dose of mosunetuzumab.

58. The method, mosunetuzumab and polatuzumab vedotin for use, or use of embodiment 54 or 57, wherein dexamethasone is administered or is to be administered orally.

59. The method, mosunetuzumab and polatuzumab vedotin for use, or use of embodiment 53, wherein the corticosteroid is methylprednisolone.

60. The method, mosunetuzumab and polatuzumab vedotin for use, or use of embodiment 59, wherein methylprednisolone is administered or is to be administered at a dose of about 1000 mg/day.

61. The method, mosunetuzumab and polatuzumab vedotin for use, or use of embodiment 59 or 60, wherein methylprednisolone is administered or is to be administered intravenously.

62. The method, mosunetuzumab and polatuzumab vedotin for use, or use of embodiment 53, wherein the corticosteroid is prednisone.

63. The method, mosunetuzumab and polatuzumab vedotin for use, or use of embodiment 62, wherein prednisone is administered or is to be administered at a dose of about 10-30 mg/day.

64. The method, mosunetuzumab and polatuzumab vedotin for use, or use of embodiment 62 or 63, wherein prednisone is administered orally.

65. The method, mosunetuzumab and polatuzumab vedotin for use, or use of embodiment 45 or 46, wherein the one or more additional therapeutic agents is acetaminophen or paracetamol.

66. The method, mosunetuzumab and polatuzumab vedotin for use, or use of embodiment 65, wherein acetaminophen or paracetamol is administered or is to be administered as a single dose of about 500-1000 mg prior to administration of any dose of polatuzumab vedotin.

67. The method, mosunetuzumab and polatuzumab vedotin for use, or use of embodiment 65 or 66, wherein acetaminophen or paracetamol is administered or is to be administered orally.

68. The method, mosunetuzumab and polatuzumab vedotin for use, or use of embodiment 45 or 46, wherein the one or more additional therapeutic agents is diphenhydramine.

69. The method, mosunetuzumab and polatuzumab vedotin for use, or use of embodiment 68, wherein diphenhydramine is administered or is to be administered as a single dose of about 50-100 mg prior to administration of any dose of polatuzumab vedotin.

70. The method, mosunetuzumab and polatuzumab vedotin for use, or use of embodiment 68 or 69, wherein diphenhydramine is administered or is to be administered orally.

71. The method, mosunetuzumab and polatuzumab vedotin for use, or use of any one of embodiments 1-70, wherein the CD20-positive cell proliferative disorder is a B cell proliferative disorder.

72. The method, mosunetuzumab and polatuzumab vedotin for use, or use of embodiment 71, wherein the B cell proliferative disorder is a non-Hodgkin's lymphoma (NHL), a chronic lymphoid leukemia (CLL), or a central nervous system lymphoma (CNSL).

73. The method, mosunetuzumab and polatuzumab vedotin for use, or use of embodiment 72, wherein the NHL is a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma.

74. The method, mosunetuzumab and polatuzumab vedotin for use, or use of embodiment 72, wherein the NHL is a relapsed and/or refractory (R/R) NHL.

75. The method, mosunetuzumab and polatuzumab vedotin for use, or use of embodiment 73, wherein the NHL is a DLBCL.

76. The method, mosunetuzumab and polatuzumab vedotin for use, or use of embodiment 75, wherein the DLBCL is an R/R DLBCL.

77. The method, mosunetuzumab and polatuzumab vedotin for use, or use of embodiment 75, wherein the DLBCL is a Richter's transformation.

78. The method, mosunetuzumab and polatuzumab vedotin for use, or use of embodiment 73, wherein the NHL is an FL.

79. The method, mosunetuzumab and polatuzumab vedotin for use, or use of embodiment 78, wherein the FL is an R/R FL.

80. The method, mosunetuzumab and polatuzumab vedotin for use, or use of embodiment 78, wherein the FL is a transformed FL.

81. The method, mosunetuzumab and polatuzumab vedotin for use, or use of embodiment 73, wherein the NHL is a HGBL.

82. The method, mosunetuzumab and polatuzumab vedotin for use, or use of embodiment 81, wherein the HGBL is an R/R HGBL.

83. The method, mosunetuzumab and polatuzumab vedotin for use, or use of embodiment 72 or 74, wherein the NHL is an aggressive NHL.

84. The method, mosunetuzumab and polatuzumab vedotin for use, or use of embodiment 83, wherein the aggressive NHL is a DLBCL, a transformed FL, or a Grade 3b FL.

85. The method, mosunetuzumab and polatuzumab vedotin for use, or use of any one of embodiments 1-84, wherein the subject is ineligible for autologous stem cell transplant (ASCT).

86. The method, mosunetuzumab and polatuzumab vedotin for use, or use of any one of 1-85, wherein the subject has relapsed after or is refractory to two or more prior lines of therapy.

87. The method, mosunetuzumab and polatuzumab vedotin for use, or use of any one of embodiments 1-86, wherein the subject is human.

88. A method of treating a population of subjects having a CD20-positive cell proliferative disorder comprising subcutaneously administering to the subjects of the population mosunetuzumab and intravenously administering to the subjects of the population polatuzumab vedotin in a dosing regimen comprising at least a first dosing cycle and a second dosing cycle, wherein:
  (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
  (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

89. Mosunetuzumab and polatuzumab vedotin for use in treating a population of subjects having a CD20-positive cell proliferative disorder, wherein mosunetuzumab is to be administered subcutaneously to the subjects of the population and polatuzumab vedotin is to be administered intravenously to the subjects of the population in a dosing regimen comprising at least a first dosing cycle and a second dosing cycle, and wherein:
  (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
  (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

90. Use of mosunetuzumab and polatuzumab vedotin for treating a population of subjects having a CD20-positive cell proliferative disorder, wherein mosunetuzumab is to be administered subcutaneously to the subjects of the population and polatuzumab vedotin is to be administered intravenously to the subjects of the population in a dosing regimen comprising at least a first dosing cycle and a second dosing cycle, and wherein:
  (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
  (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

91. Use of mosunetuzumab in the manufacture of a medicament for use in combination with polatuzumab vedotin for treating a population of subjects having a CD20-positive cell proliferative disorder, wherein mosunetuzumab is to be administered subcutaneously to the subjects of the population and polatuzumab vedotin is to be administered intravenously to the subjects of the population in a dosing regimen comprising at least a first dosing cycle and a second dosing cycle, and wherein:
  (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and
  (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

92. Use of polatuzumab vedotin in the manufacture of a medicament for use in combination with mosunetuzumab for treating a population of subjects having a CD20-positive cell proliferative disorder, wherein mosunetuzumab is to be administered subcutaneously to the subjects of the population and polatuzumab vedotin is to be administered intravenously to the subjects of the population in a dosing regimen comprising at least a first dosing cycle and a second dosing cycle, and wherein:
  (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

93. Use of mosunetuzumab and polatuzumab vedotin in the manufacture of a medicament for treating a population of subjects having a CD20-positive cell proliferative disorder, wherein mosunetuzumab is to be administered subcutaneously to the subjects of the population and polatuzumab vedotin is to be administered intravenously to the subjects of the population in a dosing regimen comprising at least a first dosing cycle and a second dosing cycle, and wherein:

(a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

94. A method of treating a population of subjects having a CD20-positive cell proliferative disorder comprising subcutaneously administering to the subjects of the population mosunetuzumab and intravenously administering to the subjects of the population polatuzumab vedotin in a dosing regimen comprising eight dosing cycles, wherein:

(a) the first dosing cycle comprises:
  (i) a first dose (C1D1) of mosunetuzumab, a second dose (C1D2) of mosunetuzumab, and a third dose (C1D3) of mosunetuzumab, wherein the C1 D1 of mosunetuzumab is about 5 mg, the C1D2 of mosunetuzumab is about 45 mg, and the C1 D3 of mosunetuzumab is about 45 mg; and
  (ii) a single dose (C1D1) of polatuzumab vedotin, wherein the C1D1 of polatuzumab vedotin is about 1.8 mg/kg;

(b) the second to sixth dosing cycles each comprises a single dose (C2D1-C6D1) of mosunetuzumab and a single dose (C2D1-C6D1) of polatuzumab vedotin, wherein each single dose C2D1-C6D1 of mosunetuzumab is about 45 mg, and wherein each single dose C2D1-C6D1 of polatuzumab vedotin is about 1.8 mg/kg; and (c) the seventh and eighth dosing cycles each comprises a single dose C7D1 and C8D1, respectively, of mosunetuzumab and does not comprise administration of polatuzumab vedotin, wherein each single dose C7D1 and C8D1 is about 45 mg.

95. Mosunetuzumab and polatuzumab vedotin for use in treating a population of subjects having a CD20-positive cell proliferative disorder, wherein mosunetuzumab is to be administered subcutaneously to the subjects of the population and polatuzumab vedotin is to be administered intravenously to the subjects of the population in a dosing regimen comprising eight dosing cycles, and wherein:

(a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

96. Use of mosunetuzumab and polatuzumab vedotin for treating a population of subjects having a CD20-positive cell proliferative disorder, wherein mosunetuzumab is to be administered subcutaneously to the subjects of the population and polatuzumab vedotin is to be administered intravenously to the subjects of the population in a dosing regimen comprising eight dosing cycles, and wherein:

(a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

97. Use of mosunetuzumab in the manufacture of a medicament for use in combination with polatuzumab vedotin for treating a population of subjects having a CD20-positive cell proliferative disorder, wherein mosunetuzumab is to be administered subcutaneously to the subjects of the population and polatuzumab vedotin is to be administered intravenously to the subjects of the population in a dosing regimen comprising eight dosing cycles, and wherein:

(a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

98. Use of polatuzumab vedotin in the manufacture of a medicament for use in combination with mosunetuzumab for treating a population of subjects having a CD20-positive cell proliferative disorder, wherein mosunetuzumab is to be administered subcutaneously to the subjects of the population and polatuzumab vedotin is to be administered intravenously to the subjects of the population in a dosing regimen comprising eight dosing cycles, and wherein:

(a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

99. Use of mosunetuzumab and polatuzumab vedotin in the manufacture of a medicament for treating a population of subjects having a CD20-positive cell proliferative disorder, wherein mosunetuzumab is to be administered subcutaneously to the subjects of the population and polatuzumab vedotin is to be administered intravenously to the subjects of the population in a dosing regimen comprising eight dosing cycles, and wherein:

(a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is about 5 mg, the C1D2 of mosunetuzumab is about 15 mg or about 45 mg, and the C1D3 of mosunetuzumab is about 45 mg, and wherein the C1D1 of polatuzumab vedotin is about 1.8 mg/kg; and (b) the second dosing cycle comprises a single dose (C2D1) of mosunetuzumab and a single dose (C2D1) of polatuzumab vedotin, wherein the C2D1 of mosunetuzumab is about 45 mg, and wherein the C2D1 of polatuzumab vedotin is about 1.8 mg/kg.

100. The method, mosunetuzumab and polatuzumab vedotin for use, or use of any one of embodiments 88-99, wherein the average duration of progression-free survival of the population of subjects is higher than a reference average duration of progression-free survival of a reference population of subjects.

101. The method, mosunetuzumab and polatuzumab vedotin for use, or use of any one of embodiments 88-99, wherein the complete response rate in the population of subjects is higher than a reference complete response rate in a reference population of subjects.

102. The method, mosunetuzumab and polatuzumab vedotin for use, or use of any one of embodiments 88-99, wherein the objective response rate in the population of subjects is higher than a reference objective response rate in a reference population of subjects.

103. The method, mosunetuzumab and polatuzumab vedotin for use, or use of any one of embodiments 88-99, wherein the average duration of response of the population of subjects is higher than a reference average duration of response of a reference population of subjects.

104. The method, mosunetuzumab and polatuzumab vedotin for use, or use of any one of embodiments 88-99, wherein the average duration of complete response of the population of subjects is higher than a reference average duration of complete response of a reference population of subjects.

105. The method, mosunetuzumab and polatuzumab vedotin for use, or use of any one of embodiments 100-104, wherein the reference population of subjects is administered or is to be administered a combination therapy comprising rituximab, gemcitabine, and oxaliplatin.

106. The method, mosunetuzumab and polatuzumab vedotin for use, or use of embodiment 105, wherein the combination therapy is administered or is to be administered to the reference population of subjects in a dosing cycle comprising eight dosing cycles.

107. The method, mosunetuzumab and polatuzumab vedotin for use, or use of embodiment 106, wherein each dosing cycle is a 14-day dosing cycle.

108. The method, mosunetuzumab and polatuzumab vedotin for use, or use of any one of embodiments 105-107, wherein the combination therapy is administered or is to be administered to the reference population of subjects about every two weeks (Q2W).

109. The method, mosunetuzumab and polatuzumab vedotin for use, or use of any one of embodiments 105-108, wherein rituximab is administered intravenously at a dose of about 375 $mg/m^2$ Q2W, gemcitabine is administered intravenously at a dose of about 1000 $mg/m^2$ Q2W, and oxaliplatin is administered intravenously at a dose of about 100 $mg/m^2$ Q2W.

110. The method, mosunetuzumab and polatuzumab vedotin for use, or use of any one of embodiments 100-109, wherein each subject in the reference population of subjects has a CD20-positive cell proliferative disorder.

111. The method, mosunetuzumab and polatuzumab vedotin for use, or use of any one of embodiments 88-110, wherein the CD20-positive cell proliferative disorder is a B cell proliferative disorder.

112. The method, mosunetuzumab and polatuzumab vedotin for use, or use of embodiment 111, wherein the B cell proliferative disorder is a non-Hodgkin's lymphoma (NHL), a chronic lymphoid leukemia (CLL), or a central nervous system lymphoma (CNSL).

113. The method, mosunetuzumab and polatuzumab vedotin for use, or use of embodiment 112, wherein the NHL is a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma.

114. The method, mosunetuzumab and polatuzumab vedotin for use, or use of embodiment 112, wherein the NHL is a relapsed and/or refractory (R/R) NHL.

115. The method, mosunetuzumab and polatuzumab vedotin for use, or use of embodiment 113, wherein the NHL is a DLBCL.

116. The method, mosunetuzumab and polatuzumab vedotin for use, or use of embodiment 115, wherein the DLBCL is an R/R DLBCL.

117. The method, mosunetuzumab and polatuzumab vedotin for use, or use of embodiment 115, wherein the DLBCL is a Richter's transformation.

118. The method, mosunetuzumab and polatuzumab vedotin for use, or use of embodiment 113, wherein the NHL is an FL.

119. The method, mosunetuzumab and polatuzumab vedotin for use, or use of embodiment 118, wherein the FL is an R/R FL.

120. The method, mosunetuzumab and polatuzumab vedotin for use, or use of embodiment 118, wherein the FL is a transformed FL.

121. The method, mosunetuzumab and polatuzumab vedotin for use, or use of embodiment 113, wherein the NHL is a HGBL.

122. The method, mosunetuzumab and polatuzumab vedotin for use, or use of embodiment 121, wherein the HGBL is an R/R HGBL.

123. The method, mosunetuzumab and polatuzumab vedotin for use, or use of embodiment 112 or 113, wherein the NHL is an aggressive NHL.

124. The method, mosunetuzumab and polatuzumab vedotin for use, or use of embodiment 123, wherein the aggressive NHL is a DLBCL, a transformed FL, or a Grade 3b FL.

125. The method, mosunetuzumab and polatuzumab vedotin for use, or use of any one of embodiments 88-124, wherein each subject in the population of subjects is ineligible for autologous stem cell transplant (ASCT).

126. The method, mosunetuzumab and polatuzumab vedotin for use, or use of any one of 88-124, wherein each subject in the population of subjects has relapsed after or is refractory to two or more prior lines of therapy.

127. The method, mosunetuzumab and polatuzumab vedotin for use, or use of any one of embodiments 88-124, wherein each subject in the population of subjects is human.

128. The method, mosunetuzumab and polatuzumab vedotin for use, or use of any one of embodiments 100-124, wherein each subject in the reference population of subjects is ineligible for autologous stem cell transplant (ASCT).

129. The method, mosunetuzumab and polatuzumab vedotin for use, or use of any one of 100-124, wherein each subject in the reference population of subjects has relapsed after or is refractory to two or more prior lines of therapy.

130. The method, mosunetuzumab and polatuzumab vedotin for use, or use of any one of embodiments 100-124, wherein each subject in the reference population of subjects is human.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating a subject having a B cell proliferative disorder comprising subcutaneously administering to the subject mosunetuzumab and intravenously administering to the subject polatuzumab vedotin in a dosing regimen comprising at least a first 21-day dosing cycle and a second 21-day dosing cycle, wherein:
   (a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is 5 mg, the C1D2 of mosunetuzumab is 15 mg, and the C1D3 of mosunetuzumab is 45 mg, and wherein the C1D1 of polatuzumab vedotin is 1.8 mg/kg; and
   (b) the second dosing cycle comprises a single dose (C2D1) of mosunetuzumab and a single dose (C2D1) of polatuzumab vedotin, wherein the C2D1 of mosunetuzumab is 45 mg, and wherein the C2D1 of polatuzumab vedotin is 1.8 mg/kg, and
   wherein the C1D1, C1D2, and C1D3 of mosunetuzumab are administered on or about Days 1, 8, and 15, respectively, of the first dosing cycle, the C1D1 of polatuzumab vedotin is administered on Day 1 of the first dosing cycle, the C2D1 of polatuzumab vedotin is administered on Day 1 of the second dosing cycle, and the C1D1 of polatuzumab vedotin is administered prior to administration of the C1D1 of mosunetuzumab.

2. The method of claim 1, wherein:
   (a) wherein the C2D1 of polatuzumab vedotin is administered prior to administration of the C2D1 of mosunetuzumab; and/or
   (b) the method further comprises one or more additional dosing cycles.

3. The method of claim 2, wherein the method comprises six additional dosing cycles.

4. The method of claim 2, wherein:
   (a) each additional dosing cycle is a 21-day dosing cycle; and/or
   (b) the one or more of the additional dosing cycles each comprise an additional single dose of mosunetuzumab and an additional single dose of polatuzumab vedotin, or the one or more of the additional dosing cycles each comprise an additional single dose of mosunetuzumab and do not comprise administration of polatuzumab vedotin.

5. The method of claim 4, wherein:
   (a) the additional single dose of polatuzumab vedotin is 1.8 mg/kg;
   (b) each additional single dose of polatuzumab vedotin is administered to the subject on Day 1 of each additional dosing cycle comprising an additional dose of polatuzumab vedotin;
   (c) the additional single dose of mosunetuzumab is 45 mg; and/or
   (d) each additional single dose of mosunetuzumab is administered to the subject on Day 1 of each additional dosing cycle comprising an additional dose of mosunetuzumab.

6. The method of claim 4, wherein the dosing regimen comprises six additional dosing cycles, wherein each of the six additional dosing cycles comprises a single dose of mosunetuzumab, and wherein no more than four of the six additional dosing cycles comprise administration of polatuzumab vedotin.

7. A method of treating a subject having a B cell proliferative disorder comprising subcutaneously administering to the subject mosunetuzumab and intravenously administering to the subject polatuzumab vedotin in a dosing regimen comprising eight 21-day dosing cycles, wherein:
   (a) the first dosing cycle comprises:
      (i) a first dose (C1D1) of mosunetuzumab, a second dose (C1D2) of mosunetuzumab, and a third dose (C1D3) of mosunetuzumab, wherein the C1D1 of mosunetuzumab is 5 mg, the C1D2 of mosunetuzumab is 45 mg, and the C1D3 of mosunetuzumab is 45 mg; and
      (ii) a single dose (C1D1) of polatuzumab vedotin, wherein the C1D1 of polatuzumab vedotin is 1.8 mg/kg;
   (b) the second to sixth dosing cycles each comprises a single dose (C2D1-C6D1) of mosunetuzumab and a single dose (C2D1-C6D1) of polatuzumab vedotin, wherein each single dose C2D1-C6D1 of mosunetuzumab is 45 mg, and wherein each single dose C2D1-C6D1 of polatuzumab vedotin is 1.8 mg/kg; and
   (c) the seventh and eighth dosing cycles each comprises a single dose C7D1 and C8D1, respectively, of mosunetuzumab and does not comprise administration of polatuzumab vedotin, wherein each single dose C7D1 and C8D1 is 45 mg, and
   wherein the C1D1, C1D2, and C1D3 of mosunetuzumab are administered on or about Days 1, 8, and 15, respectively, of the first dosing cycle, each single dose of the C2D1-C8D1 of mosunetuzumab is administered on Day 1 of each respective dosing cycle, and each single dose of the C1D1-C6D1 of polatuzumab vedotin is administered on Day 1 of each respective dosing cycle.

8. The method of claim 7, wherein:
   (a) the C1D1 of polatuzumab vedotin is administered prior to administration of the C1D1 of mosunetuzumab, and wherein the C2D1 of polatuzumab vedotin is administered prior to administration of the C2D1 of mosunetuzumab; and/or
   (b) each single dose C3D1-C6D1 of polatuzumab vedotin is administered prior to administration of each single dose C3D1-C6D1 of mosunetuzumab, respectively.

9. The method of claim 8, wherein polatuzumab vedotin is administered at least about 60 minutes prior to administration of mosunetuzumab.

10. The method of claim 1, wherein the method further comprises administering to the subject one or more additional therapeutic agents.

11. The method of claim 10, wherein the one or more additional therapeutic agents is a corticosteroid or an IL-6R antagonist.

12. The method of claim 11, wherein:
   (a) the IL-6R antagonist is tocilizumab, and wherein tocilizumab is administered:
      (i) to the subject as a single dose of 8 mg/kg or 12 mg/kg, and wherein the single dose does not exceed 800 mg; and/or
      (ii) intravenously;
   (b) the corticosteroid is dexamethasone, and wherein dexamethasone is administered:
      (i) as a single dose of 10 mg every 6 hours;
      (ii) as a single dose of 20 mg prior to administration of any dose of mosunetuzumab; and/or
      (iii) orally or intravenously;
   (c) the corticosteroid is prednisone, and wherein prednisone is administered:
      (i) at a dose of 10-30 mg/day; and/or
      (ii) orally; or (d) the corticosteroid is methylprednisolone, and wherein methylprednisolone is administered:
  (i) at a dose of 1000 mg/day; and/or
  (ii) intravenously.

13. The method of claim 10, wherein the one or more additional therapeutic agents is:
  (a) acetaminophen or paracetamol, wherein acetaminophen or paracetamol is administered:
    (i) as a single dose of 500-1000 mg prior to administration of any dose of polatuzumab vedotin; and/or
    (ii) orally; or
  (b) diphenhydramine, wherein diphenhydramine is administered:
    (i) as a single dose of 50-100 mg prior to administration of any dose of polatuzumab vedotin; and/or
    (ii) orally.

14. The method of claim 1, wherein the B cell proliferative disorder is a non-Hodgkin's lymphoma (NHL), a chronic lymphoid leukemia (CLL), or a central nervous system lymphoma (CNSL).

15. The method of claim 14, wherein the NHL is:
  (a) a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma;
  (b) a relapsed and/or refractory (R/R) NHL; and/or
  (c) an aggressive NHL, wherein the aggressive NHL is a DLBCL, a transformed FL, or a Grade 3b FL.

16. The method of claim 15, wherein the NHL is:
  (a) a DLBCL, and wherein the DLBCL is:
    (i) an R/R DLBCL; and/or
    (ii) a Richter's transformation;
  (b) an FL, and wherein the FL is:
    (i) an R/R FL; and/or
    (ii) a transformed FL; or
  (c) a HGBL, and wherein the HGBL is an R/R HGBL.

17. The method of claim 1, wherein the subject:
  (a) is ineligible for autologous stem cell transplant (ASCT);
  (b) has relapsed after or is refractory to two or more prior lines of therapy; and/or
  (c) is human.

18. A method of treating a population of subjects having a B cell proliferative disorder comprising subcutaneously administering to the subjects of the population mosunetuzumab and intravenously administering to the subjects of the population polatuzumab vedotin in a dosing regimen comprising eight 21-day dosing cycles, wherein:
  (a) the first dosing cycle comprises:
    (i) a first dose (C1D1) of mosunetuzumab, a second dose (C1D2) of mosunetuzumab, and a third dose (C1D3) of mosunetuzumab, wherein the C1D1 of mosunetuzumab is 5 mg, the C1D2 of mosunetuzumab is 45 mg, and the C1D3 of mosunetuzumab is 45 mg; and
    (ii) a single dose (C1D1) of polatuzumab vedotin, wherein the C1D1 of polatuzumab vedotin is 1.8 mg/kg;
  (b) the second to sixth dosing cycles each comprises a single dose (C2D1-C6D1) of mosunetuzumab and a single dose (C2D1-C6D1) of polatuzumab vedotin, wherein each single dose C2D1-C6D1 of mosunetuzumab is 45 mg, and wherein each single dose C2D1-C6D1 of polatuzumab vedotin is 1.8 mg/kg; and
  (c) the seventh and eighth dosing cycles each comprises a single dose C7D1 and C8D1, respectively, of mosunetuzumab and does not comprise administration of polatuzumab vedotin, wherein each single dose C7D1 and C8D1 is 45 mg, and
  wherein the C1D1, C1D2, and C1D3 of mosunetuzumab are administered on or about Days 1, 8, and 15, respectively, of the first dosing cycle, each single dose of the C2D1-C8D1 of mosunetuzumab is administered on Day 1 of each respective dosing cycle, and each single dose of the C1D1-C6D1 of polatuzumab vedotin is administered on Day 1 of each respective dosing cycle.

19. The method of claim 18, wherein:
  (a) the average duration of progression-free survival of the population of subjects is higher than a reference average duration of progression-free survival of a reference population of subjects;
  (b) the complete response rate in the population of subjects is higher than a reference complete response rate in a reference population of subjects;
  (c) the objective response rate in the population of subjects is higher than a reference objective response rate in a reference population of subjects;
  (d) the average duration of response of the population of subjects is higher than a reference average duration of response of a reference population of subjects; and/or
  (e) the average duration of complete response of the population of subjects is higher than a reference average duration of complete response of a reference population of subjects.

20. The method of claim 19, wherein the reference population of subjects is administered a combination therapy comprising rituximab, gemcitabine, and oxaliplatin.

21. The method of claim 20, wherein:
  (a) the combination therapy is administered to the reference population of subjects in a dosing cycle comprising eight dosing cycles and/or about every two weeks (Q2W); and/or
  (b) rituximab is administered intravenously at a dose of 375 mg/m$^2$ Q2W, gemcitabine is administered intravenously at a dose of 1000 mg/m$^2$ Q2W, and oxaliplatin is administered intravenously at a dose of 100 mg/m$^2$ Q2W.

22. The method of claim 21, wherein each dosing cycle is a 14-day dosing cycle.

23. The method of claim 19, wherein each subject in the reference population of subjects has a B cell proliferative disorder.

24. The method of claim 18, wherein the B cell proliferative disorder is a non-Hodgkin's lymphoma (NHL), a chronic lymphoid leukemia (CLL), or a central nervous system lymphoma (CNSL).

25. The method of claim 24, wherein the NHL is:
  (a) a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma;
  (b) a relapsed and/or refractory (R/R) NHL; and/or
  (c) an aggressive NHL, wherein the aggressive NHL is a DLBCL, a transformed FL, or a Grade 3b FL.

26. The method of claim 25, wherein the NHL is:
(a) a DLBCL, and wherein the DLBCL is:
  (i) an R/R DLBCL; and/or
  (ii) a Richter's transformation;
(b) an FL, and wherein the FL is:
  (i) an R/R FL; and/or
  (ii) a transformed FL; or
(c) a HGBL, and wherein the HGBL is an R/R HGBL.

27. The method of claim 18 wherein each subject in the population of subjects:
(a) is ineligible for autologous stem cell transplant (ASCT);
(b) has relapsed after or is refractory to two or more prior lines of therapy; and/or
(c) is human.

28. The method of claim 19, wherein each subject in the reference population of subjects:
(a) is ineligible for autologous stem cell transplant (ASCT);
(b) has relapsed after or is refractory to two or more prior lines of therapy; and/or
(c) is human.

29. The method of claim 23, wherein the B cell proliferative disorder is a non-Hodgkin's lymphoma (NHL), a chronic lymphoid leukemia (CLL), or a central nervous system lymphoma (CNSL).

30. The method of claim 29, wherein the NHL is:
(a) a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma;
(b) a relapsed and/or refractory (R/R) NHL; and/or
(c) an aggressive NHL, wherein the aggressive NHL is a DLBCL, a transformed FL, or a Grade 3b FL.

31. The method of claim 30, wherein the NHL is:
(a) a DLBCL, and wherein the DLBCL is:
  (i) an R/R DLBCL; and/or
  (ii) a Richter's transformation;
(b) an FL, and wherein the FL is:
  (i) an R/R FL; and/or
  (ii) a transformed FL; or
(c) a HGBL, and wherein the HGBL is an R/R HGBL.

32. A method of treating a subject having a B cell proliferative disorder comprising subcutaneously administering to the subject mosunetuzumab and intravenously administering to the subject polatuzumab vedotin in a dosing regimen comprising at least a first 21-day dosing cycle and a second 21-day dosing cycle, wherein:
(a) the first dosing cycle comprises a first dose (C1D1) of mosunetuzumab, a second dose (C1D2) of the mosunetuzumab, a third dose (C1D3) of mosunetuzumab, and a first dose (C1D1) of polatuzumab vedotin, wherein the C1D1 of mosunetuzumab is 5 mg, the C1D2 of mosunetuzumab is 45 mg, and the C1D3 of mosunetuzumab is 45 mg, and wherein the C1D1 of polatuzumab vedotin is 1.8 mg/kg; and
(b) the second dosing cycle comprises a single dose (C2D1) of mosunetuzumab and a single dose (C2D1) of polatuzumab vedotin, wherein the C2D1 of mosunetuzumab is 45 mg, and wherein the C2D1 of polatuzumab vedotin is 1.8 mg/kg, and
wherein the C1D1, C1D2, and C1D3 of mosunetuzumab are administered on or about Days 1, 8, and 15, respectively, of the first dosing cycle, the C1D1 of polatuzumab vedotin is administered on Day 1 of the first dosing cycle, the C2D1 of polatuzumab vedotin is administered on Day 1 of the second dosing cycle, and the C1D1 of polatuzumab vedotin is administered prior to administration of the C1D1 of mosunetuzumab.

33. The method of claim 32, wherein:
(a) the C1D1 of polatuzumab vedotin is administered prior to administration of the C1D1 of mosunetuzumab, and wherein the C2D1 of polatuzumab vedotin is administered prior to administration of the C2D1 of mosunetuzumab; and/or
(b) the method further comprises one or more additional dosing cycles.

34. The method of claim 33, wherein the method comprises six additional dosing cycles.

35. The method of claim 33, wherein:
(a) each additional dosing cycle is a 21-day dosing cycle; and/or
(b) the one or more of the additional dosing cycles each comprise an additional single dose of mosunetuzumab and an additional single dose of polatuzumab vedotin, or the one or more of the additional dosing cycles each comprise an additional single dose of mosunetuzumab and do not comprise administration of polatuzumab vedotin.

36. The method of claim 35, wherein:
(a) the additional single dose of polatuzumab vedotin is 1.8 mg/kg;
(b) each additional single dose of polatuzumab vedotin is administered to the subject on Day 1 of each additional dosing cycle comprising an additional dose of polatuzumab vedotin;
(c) the additional single dose of mosunetuzumab is 45 mg; and/or
(d) each additional single dose of mosunetuzumab is administered to the subject on Day 1 of each additional dosing cycle comprising an additional dose of mosunetuzumab.

37. The method of claim 35, wherein the dosing regimen comprises six additional dosing cycles, wherein each of the six additional dosing cycles comprises a single dose of mosunetuzumab, and wherein no more than four of the six additional dosing cycles comprise administration of polatuzumab vedotin.

38. The method of claim 32, wherein the method further comprises administering to the subject one or more additional therapeutic agents.

39. The method of claim 38, wherein the one or more additional therapeutic agents is a corticosteroid or an IL-6R antagonist.

40. The method of claim 39, wherein:
(a) the IL-6R antagonist is tocilizumab, and wherein tocilizumab is administered:
  (i) to the subject as a single dose of 8 mg/kg or 12 mg/kg, and wherein the single dose does not exceed 800 mg; and/or
  (ii) intravenously;
(b) the corticosteroid is dexamethasone, and wherein dexamethasone is administered:
  (i) as a single dose of 10 mg every 6 hours;
  (ii) as a single dose of 20 mg prior to administration of any dose of mosunetuzumab; and/or
  (iii) orally or intravenously;

(c) the corticosteroid is prednisone, and wherein prednisone is administered:
  (i) at a dose of 10-30 mg/day; and/or
  (ii) orally; or
(d) the corticosteroid is methylprednisolone, and wherein methylprednisolone is administered:
  (i) at a dose of 1000 mg/day; and/or
  (ii) intravenously.

41. The method of claim 38, wherein the one or more additional therapeutic agents is:
(a) acetaminophen or paracetamol, wherein acetaminophen or paracetamol is administered:
  (i) as a single dose of 500-1000 mg prior to administration of any dose of polatuzumab vedotin; and/or
  (ii) orally; or
(b) diphenhydramine, wherein diphenhydramine is administered:
  (i) as a single dose of 50-100 mg prior to administration of any dose of polatuzumab vedotin; and/or
  (ii) orally.

42. The method of claim 32, wherein the B cell proliferative disorder is a non-Hodgkin's lymphoma (NHL), a chronic lymphoid leukemia (CLL), or a central nervous system lymphoma (CNSL).

43. The method of claim 42, wherein the NHL is:
(a) a diffuse-large B cell lymphoma (DLBCL), a follicular lymphoma (FL), a high-grade B cell lymphoma (HGBL), a mantle cell lymphoma (MCL), a high-grade B cell lymphoma, a primary mediastinal (thymic) large B cell lymphoma (PMLBCL), a diffuse B cell lymphoma, a small lymphocytic lymphoma, a marginal zone lymphoma (MZL), a Burkitt lymphoma, or a lymphoplasmacytic lymphoma;
(b) a relapsed and/or refractory (R/R) NHL; and/or
(c) an aggressive NHL, wherein the aggressive NHL is a DLBCL, a transformed FL, or a Grade 3b FL.

* * * * *

SEQUENCE LISTING

```
<160> NUMBER OF SEQ ID NOS: 54

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Tyr Thr Phe Thr Ser Tyr Asn Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Ala Ile Tyr Pro Gly Asn Gly Asp Thr Ser Tyr Asn Gln Lys Phe Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Val Val Tyr Tyr Ser Asn Ser Tyr Trp Tyr Phe Asp Val
1               5                   10

<210> SEQ ID NO 4
<211> LENGTH: 10
<212> TYPE: PRT
<213> ORGANISM: Artificial Sequence
<220> FEATURE:
```

```
<223> OTHER INFORMATION: Synthetic Construct

<400> SEQUENCE: 4

Arg Ala Ser Ser Ser Val Ser Tyr Met His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Ala Pro Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Trp Ser Phe Asn Pro Pro Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser
        115                 120

<210> SEQ ID NO 8
<211> LENGTH: 106
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Ser Val Ser Tyr Met
            20                  25                  30

His Trp Tyr Gln Gln Lys Pro Gly Lys Ala Pro Lys Leu Ile Tyr
        35                  40                  45

Ala Pro Ser Asn Leu Ala Ser Gly Val Pro Ser Arg Phe Ser Gly
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys
            100                 105
```

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

```
Asn Tyr Tyr Ile His
1               5
```

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

```
Trp Ile Tyr Pro Gly Asp Gly Asn Thr Lys Tyr Asn Glu Lys Phe Lys
1               5                   10                  15

Gly
```

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

```
Asp Ser Tyr Ser Asn Tyr Phe Asp Tyr
1               5                   10
```

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

```
Lys Ser Ser Gln Ser Leu Leu Asn Ser Arg Thr Arg Lys Asn Tyr Leu
1               5                   10                  15

Ala
```

<210> SEQ ID NO 13
<211> LENGTH: 7
<212> TYPE: PRT

<213> ORGANISM: Artificial Sequence
<220> FEATURE:
<223> OTHER INFORMATION: Synthetic Construct

<400> SEQUENCE: 13

Trp Ala Ser Thr Arg Glu Ser
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Thr Gln Ser Phe Ile Leu Arg Thr
1               5

<210> SEQ ID NO 15
<211> LENGTH: 119
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 16
<211> LENGTH: 112
<212> TYPE: PRT
<213> ORGANISM: Artificial Sequence
<220> FEATURE:
<223> OTHER INFORMATION: Synthetic Construct

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr

```
                65                  70                  75                  80
Ile Ser Ser Leu Gln Ala Glu Asp Val Ala Val Tyr Tyr Cys Thr Gln
                    85                  90                  95

Ser Phe Ile Leu Arg Thr Phe Gly Gln Gly Thr Lys Val Glu Ile Lys
                    100                 105                 110

<210> SEQ ID NO 17
<211> LENGTH: 25
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct

<400> SEQUENCE: 18

Trp Val Arg Gln Ala Pro Gly Lys Gly Leu Glu Trp Val Gly
1               5                   10

<210> SEQ ID NO 19
<211> LENGTH: 32
<212> TYPE: PRT
<213> ORGANISM: Artificial Sequence
<220> FEATURE:
<223> OTHER INFORMATION: Synthetic Construct

<400> SEQUENCE: 19

Arg Phe Thr Ile Ser Val Asp Lys Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Trp Gly Gln Gly Thr Leu Val Thr Val Ser Ser
1               5                   10

<210> SEQ ID NO 21
<211> LENGTH: 23
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
1               5                   10                  15
```

Asp Arg Val Thr Ile Thr Cys
            20

<210> SEQ ID NO 22
<211> LENGTH: 15
<212> TYPE: PRT
<213> ORGANISM: Artificial Sequence
<220> FEATURE:
<223> OTHER INFORMATION: Synthetic Construct

<400> SEQUENCE: 22

Trp Tyr Gln Gln Lys Pro Gly Lys Ala Pro Lys Pro Leu Ile Tyr
1               5                   10                  15

<210> SEQ ID NO 23
<211> LENGTH: 32
<212> TYPE: PRT
<213> ORGANISM: Artificial Sequence
<220> FEATURE:
<223> OTHER INFORMATION: Synthetic Construct

<400> SEQUENCE: 23

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct

<400> SEQUENCE: 24

Phe Gly Gln Gly Thr Lys Val Glu Ile Lys
1               5                   10

<210> SEQ ID NO 25
<211> LENGTH: 30
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 26
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26

Trp Val Arg Gln Ala Pro Gly Gln Gly Leu Glu Trp Ile Gly
1               5                   10

<210> SEQ ID NO 27
<211> LENGTH: 32
<212> TYPE: PRT
<213> ORGANISM: Artificial Sequence
<220> FEATURE:
<223> OTHER INFORMATION: Synthetic Construct

<400> SEQUENCE: 27

Arg Ala Thr Leu Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Trp Gly Gln Gly Thr Leu Val Thr Val Ser Ser
1               5                   10

<210> SEQ ID NO 29
<211> LENGTH: 23
<212> TYPE: PRT
<213> ORGANISM: Artificial Sequence
<220> FEATURE:
<223> OTHER INFORMATION: Synthetic Construct

<400> SEQUENCE: 29

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Trp Tyr Gln Gln Lys Pro Gly Gln Pro Pro Lys Leu Leu Ile Tyr
1               5                   10                  15

<210> SEQ ID NO 31
<211> LENGTH: 32
<212> TYPE: PRT
<213> ORGANISM: Artificial Sequence
<220> FEATURE:
<223> OTHER INFORMATION: Synthetic Construct

<400> SEQUENCE: 31

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Phe Gly Gln Gly Thr Lys Val Glu Ile Lys
1               5                   10

<210> SEQ ID NO 33
<211> LENGTH: 452
<212> TYPE: PRT
<213> ORGANISM: Artificial Sequence
<220> FEATURE:
<223> OTHER INFORMATION: Synthetic Construct

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gly Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

-continued

Val Tyr Thr Leu Pro Pro Ser Arg Glu Glu Met Thr Lys Asn Gln Val
            355                 360                 365

Ser Leu Trp Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 34
<211> LENGTH: 213
<212> TYPE: PRT
<213> ORGANISM: Artificial Sequence
<220> FEATURE:
<223> OTHER INFORMATION: Synthetic Construct

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 35
<211> LENGTH: 449
<212> TYPE: PRT
<213> ORGANISM: Artificial Sequence
<220> FEATURE:

<223> OTHER INFORMATION: Synthetic Construct

<400> SEQUENCE: 35

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

```
Asp Ser Asp Gly Ser Phe Phe Leu Val Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 36
<211> LENGTH: 219
<212> TYPE: PRT
<213> ORGANISM: Artificial Sequence
<220> FEATURE:
<223> OTHER INFORMATION: Synthetic Construct

<400> SEQUENCE: 36

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 37
<211> LENGTH: 10
<212> TYPE: PRT
<213> ORGANISM: Artificial Sequence
<220> FEATURE:
<223> OTHER INFORMATION: Synthetic Construct

<400> SEQUENCE: 37

Gly Tyr Thr Phe Ser Ser Tyr Trp Ile Glu
1               5                   10

<210> SEQ ID NO 38
<211> LENGTH: 18
```

-continued

```
<212> TYPE: PRT
<213> ORGANISM: Artificial Sequence
<220> FEATURE:
<223> OTHER INFORMATION: Synthetic Construct

<400> SEQUENCE: 38

Gly Glu Ile Leu Pro Gly Gly Gly Asp Thr Asn Tyr Asn Glu Ile Phe
1               5                   10                  15

Lys Gly

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct

<400> SEQUENCE: 39

Thr Arg Arg Val Pro Ile Arg Leu Asp Tyr
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Synthetic Construct

<400> SEQUENCE: 40

Lys Ala Ser Gln Ser Val Asp Tyr Glu Gly Asp Ser Phe Leu Asn
1               5                   10                  15

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41

Ala Ala Ser Asn Leu Glu Ser
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

Gln Gln Ser Asn Glu Asp Pro Leu Thr
1               5

<210> SEQ ID NO 43
<211> LENGTH: 117
<212> TYPE: PRT
<213> ORGANISM: Artificial Sequence
<220> FEATURE:
<223> OTHER INFORMATION: Synthetic Construct

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30
```

Trp Ile Glu Trp Val Arg Gln Ala Pro Gly Lys Gly Leu Glu Trp Ile
           35                  40                  45

Gly Glu Ile Leu Pro Gly Gly Asp Thr Asn Tyr Asn Glu Ile Phe
       50                  55                  60

Lys Gly Arg Ala Thr Phe Ser Asp Thr Ser Lys Asn Thr Ala Tyr
65                  70                  75                  80

Leu Gln Met Asn Ser Leu Arg Ala Glu Asp Thr Ala Val Tyr Tyr Cys
               85                  90                  95

Thr Arg Arg Val Pro Ile Arg Leu Asp Tyr Trp Gly Gln Gly Thr Leu
               100                 105                 110

Val Thr Val Ser Ser
        115

<210> SEQ ID NO 44
<211> LENGTH: 112
<212> TYPE: PRT
<213> ORGANISM: Artificial Sequence
<220> FEATURE:
<223> OTHER INFORMATION: Synthetic Construct

<400> SEQUENCE: 44

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

<210> SEQ ID NO 45
<211> LENGTH: 25
<212> TYPE: PRT
<213> ORGANISM: Artificial Sequence
<220> FEATURE:
<223> OTHER INFORMATION: Synthetic Construct

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 46
<211> LENGTH: 13
<212> TYPE: PRT
<213> ORGANISM: Artificial Sequence
<220> FEATURE:
<223> OTHER INFORMATION: Synthetic Construct

<400> SEQUENCE: 46

Trp Val Arg Gln Ala Pro Gly Lys Gly Leu Glu Trp Ile
1               5                   10

<210> SEQ ID NO 47
<211> LENGTH: 30
<212> TYPE: PRT
<213> ORGANISM: Artificial Sequence
<220> FEATURE:
<223> OTHER INFORMATION: Synthetic Construct

<400> SEQUENCE: 47

```
Arg Ala Thr Phe Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30
```

<210> SEQ ID NO 48
<211> LENGTH: 11
<212> TYPE: PRT
<213> ORGANISM: Artificial Sequence
<220> FEATURE:
<223> OTHER INFORMATION: Synthetic Construct

<400> SEQUENCE: 48

```
Trp Gly Gln Gly Thr Leu Val Thr Val Ser Ser
1               5                   10
```

<210> SEQ ID NO 49
<211> LENGTH: 23
<212> TYPE: PRT
<213> ORGANISM: Artificial Sequence
<220> FEATURE:
<223> OTHER INFORMATION: Synthetic Construct

<400> SEQUENCE: 49

```
Asp Ile Gln Leu Thr Gln Ser Pro Ser Ser Leu Ser Ala Ser Val Gly
1               5                   10                  15

Asp Arg Val Thr Ile Thr Cys
            20
```

<210> SEQ ID NO 50
<211> LENGTH: 15
<212> TYPE: PRT
<213> ORGANISM: Artificial Sequence
<220> FEATURE:
<223> OTHER INFORMATION: Synthetic Construct

<400> SEQUENCE: 50

```
Trp Tyr Gln Gln Lys Pro Gly Lys Ala Pro Lys Leu Leu Ile Tyr
1               5                   10                  15
```

<210> SEQ ID NO 51
<211> LENGTH: 32
<212> TYPE: PRT
<213> ORGANISM: Artificial Sequence
<220> FEATURE:
<223> OTHER INFORMATION: Synthetic Construct

<400> SEQUENCE: 51

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 52
<211> LENGTH: 11
<212> TYPE: PRT
<213> ORGANISM: Artificial Sequence

```
<220> FEATURE:
<223> OTHER INFORMATION: Synthetic Construct

<400> SEQUENCE: 52

Phe Gly Gln Gly Thr Lys Val Glu Ile Lys Arg
1               5                   10

<210> SEQ ID NO 53
<211> LENGTH: 447
<212> TYPE: PRT
<213> ORGANISM: Artificial Sequence
<220> FEATURE:
<223> OTHER INFORMATION: Synthetic Construct

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
```

```
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 54
<211> LENGTH: 218
<212> TYPE: PRT
<213> ORGANISM: Artificial Sequence
<220> FEATURE:
<223> OTHER INFORMATION: Synthetic Construct

<400> SEQUENCE: 54

Asp Ile Gln Leu Thr Gln Ser Pro Ser Ser Leu Ser Ala Ser Val Gly
1               5                   10                  15
Asp Arg Val Thr Ile Thr Cys Lys Ala Ser Gln Ser Val Asp Tyr Glu
                20                  25                  30
Gly Asp Ser Phe Leu Asn Trp Tyr Gln Gln Lys Pro Gly Lys Ala Pro
            35                  40                  45
Lys Leu Leu Ile Tyr Ala Ala Ser Asn Leu Glu Ser Gly Val Pro Ser
    50                  55                  60
Arg Phe Ser Gly Ser Gly Ser Gly Thr Asp Phe Thr Leu Thr Ile Ser
65                  70                  75                  80
Ser Leu Gln Pro Glu Asp Phe Ala Thr Tyr Tyr Cys Gln Gln Ser Asn
                85                  90                  95
Glu Asp Pro Leu Thr Phe Gly Gln Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```